(12) United States Patent
Nelsestuen

(10) Patent No.: US 7,479,551 B2
(45) Date of Patent: Jan. 20, 2009

(54) MODIFIED VITAMIN K-DEPENDENT POLYPEPTIDES

(75) Inventor: Gary L Nelsestuen, St. Paul, MN (US)

(73) Assignee: Regents of the University of Minnesota, St. Paul, MN (US)

( * ) Notice: Subject to any disclaimer, the term of this patent is extended or adjusted under 35 U.S.C. 154(b) by 99 days.

(21) Appl. No.: 11/539,439

(22) Filed: Oct. 6, 2006

(65) Prior Publication Data

US 2007/0066531 A1 Mar. 22, 2007

Related U.S. Application Data

(60) Division of application No. 10/298,330, filed on Nov. 18, 2002, now Pat. No. 7,247,708, which is a continuation-in-part of application No. 09/497,591, filed on Feb. 3, 2000, now Pat. No. 6,747,003, which is a continuation-in-part of application No. 09/302,239, filed on Apr. 29, 1999, now Pat. No. 6,693,075, which is a continuation-in-part of application No. 08/955,636, filed on Oct. 23, 1997, now Pat. No. 6,017,882.

(51) Int. Cl.
*C07H 21/04* (2006.01)
*A61K 35/14* (2006.01)
*A61K 35/16* (2006.01)
*A61K 38/16* (2006.01)
*A61K 38/14* (2006.01)

(52) U.S. Cl. ............. 536/23.1; 530/380; 530/384; 514/2; 514/8; 514/12

(58) Field of Classification Search .......... 536/23.1; 530/380, 384; 514/2, 8, 12
See application file for complete search history.

(56) References Cited

U.S. PATENT DOCUMENTS

| | | | |
|---|---|---|---|
| 4,784,950 A | 11/1988 | Hagen et al. | |
| 4,904,584 A | 2/1990 | Shaw | |
| 5,009,889 A | 4/1991 | Taylor, Jr. et al. | |
| 5,041,376 A | 8/1991 | Gething et al. | |
| 5,093,317 A | 3/1992 | Lewis et al. | |
| 5,180,583 A | 1/1993 | Hedner | |
| 5,225,537 A | 7/1993 | Foster | |
| 5,258,288 A | 11/1993 | Wydro et al. | |
| 5,288,629 A | 2/1994 | Berkner | |
| 5,374,617 A | 12/1994 | Morrissey et al. | |
| 5,460,950 A | 10/1995 | Barr et al. | |
| 5,504,064 A | 4/1996 | Morrissey et al. | |
| 5,516,640 A | 5/1996 | Watanabe et al. | |
| 5,580,560 A | 12/1996 | Nicolaisen et al. | |
| 5,648,254 A | 7/1997 | Mulvihill et al. | |
| 5,788,965 A | 8/1998 | Berkner et al. | |
| 5,817,788 A | 10/1998 | Berkner et al. | |
| 5,824,639 A | 10/1998 | Berkner | |
| 5,833,982 A | 11/1998 | Berkner et al. | |
| 5,837,843 A | 11/1998 | Smirnov et al. | |
| 5,847,085 A | 12/1998 | Esmon et al. | |
| 5,861,374 A | 1/1999 | Berkner et al. | |
| 5,891,843 A | 4/1999 | Turecek et al. | |
| 5,965,425 A | 10/1999 | Barr et al. | |
| 5,986,079 A | 11/1999 | Barr et al. | |
| 6,013,620 A | 1/2000 | Turecek et al. | |
| 6,017,882 A | 1/2000 | Nelsestuen | |
| 6,071,514 A | 6/2000 | Grinnell et al. | |
| 6,423,826 B1 | 7/2002 | Nelsestuen et al. | |
| 6,693,075 B1 | 2/2004 | Nelsestuen | |
| 6,747,003 B1 | 6/2004 | Nelsestuen | |
| 6,762,286 B2 | 7/2004 | Nelsestuen | |
| 6,806,063 B2 | 10/2004 | Pedersen et al. | |
| 6,903,069 B2 | 6/2005 | Pingel et al. | |
| 7,160,540 B2 | 1/2007 | Nelsestuen | |
| 7,220,837 B1 | 5/2007 | Nelsestuen | |
| 7,247,708 B2 | 7/2007 | Nelsestuen | |
| 7,294,699 B2 | 11/2007 | Nelsestuen | |
| 7,314,917 B2 | 1/2008 | Nelsestuen | |
| 2003/0100506 A1 | 5/2003 | Nelsestuen | |
| 2003/0100740 A1 | 5/2003 | Persson et al. | |
| 2003/0104978 A1 | 6/2003 | Persson et al. | |
| 2003/0186862 A1 | 10/2003 | Nelsestuen | |
| 2003/0211094 A1 | 11/2003 | Nelsestuen | |
| 2003/0211460 A1 | 11/2003 | Nelsestuen | |

(Continued)

FOREIGN PATENT DOCUMENTS

| | | |
|---|---|---|
| EP | 0 296 413 | 12/1988 |
| EP | 0 354 504 | 2/1990 |
| EP | 0 512 011 | 11/1992 |
| JP | 64-085096 | 3/1989 |
| WO | WO 88/10295 | 12/1988 |
| WO | WO 91/11514 | 8/1991 |
| WO | WO 92/15686 | 9/1992 |
| WO | WO 94/27631 | 12/1994 |
| WO | WO 96/00577 | 1/1996 |
| WO | WO 99/03498 | 1/1999 |
| WO | WO 99/20767 | 4/1999 |
| WO | WO 99/66031 | 12/1999 |
| WO | WO 00/28065 | 5/2000 |
| WO | WO 00/54787 | 9/2000 |
| WO | WO 00/66753 | 11/2000 |

(Continued)

OTHER PUBLICATIONS

Harvey, "Mutagenesis of the γ-Carboxyglutamic Acid Domain of Human Factor VII to Generate Maximum Enhancement of the Membrane Contact Site," *J. Biol. Chem.*, 2003, 278:8363-8369.

(Continued)

*Primary Examiner*—Maryam Monshipouri
*Assistant Examiner*—Marsha M Tsay
(74) *Attorney, Agent, or Firm*—Fish & Richardson P.C.

(57) ABSTRACT

The invention provides vitamin K-dependent polypeptides with enhanced membrane binding affinity. These polypeptides can be used to modulate clot formation in mammals. Methods of modulating clot formation in mammals are also described.

19 Claims, 20 Drawing Sheets

U.S. PATENT DOCUMENTS

| | | |
|---|---|---|
| 2005/0059132 A1 | 3/2005 | Nelsestuen |
| 2006/0264373 A1 | 11/2006 | Nelsestuen |
| 2006/0264616 A1 | 11/2006 | Nelsestuen |
| 2007/0066531 A1 | 3/2007 | Nelsestuen |
| 2007/0087448 A1 | 4/2007 | Nelsestuen |
| 2007/0161561 A1 | 7/2007 | Nelsestuen |
| 2007/0225223 A1 | 9/2007 | Nelsestuen |
| 2007/0225224 A1 | 9/2007 | Nelsestuen |
| 2007/0254840 A1 | 11/2007 | Nelsestuen |
| 2008/0004216 A1 | 1/2008 | Nelsestuen |
| 2008/0004221 A1 | 1/2008 | Nelsestuen |
| 2008/0026994 A1 | 1/2008 | Nelsestuen |

FOREIGN PATENT DOCUMENTS

| | | |
|---|---|---|
| WO | WO 01/58935 | 8/2001 |
| WO | WO 01/83725 | 11/2001 |
| WO | WO 02/02764 | 1/2002 |
| WO | WO 02/03075 | 1/2002 |
| WO | WO 02/22776 | 3/2002 |
| WO | WO 02/29025 | 4/2002 |
| WO | WO 02/38162 | 5/2002 |
| WO | WO02/070681 | 9/2002 |
| WO | WO 02/077218 | 10/2002 |
| WO | WO 03/027147 | 4/2003 |
| WO | WO 03/037932 | 5/2003 |
| WO | WO 03/055512 | 7/2003 |
| WO | WO 03/093465 | 11/2003 |
| WO | WO 2004/029091 | 4/2004 |
| WO | WO 2004/083361 | 9/2004 |

OTHER PUBLICATIONS

Henderson et al., "Response of Factor VIII and IX-Deficient Blood to Wild Type and High Membrane Affinity Mutant Factor VIIa in an In Vitro Whole Blood Clotting Assay: Possible Correlation to Clinical Outcome," *Thromb. Haemost.*, 2002, 88:98-103.

Stone, "Unusual Benefits of Macromolecular Shielding by Polyethylene Glycol for Reactions at the Diffusional Limit: The Case of Factor VIIai and Tissue Factor," *Biochem.*, 2002, 41:15820-15825.

Toomey et al., "Localization of the Human Tissue Factor Recognition Determinant of Human Factor VIIa," *J. Biol. Chem.*, 1991, 266:19198-19202.

"Docking of Tissue Factor and Factor VIIa Initiates Blood Coagulation," at http://www.sdsc.edu.IOTW/week46.96/ (1996).

Bharadwaj et al., "Factor VII central. A novel mutation in the catalytic domain that reduces tissue factor binding, impairs activation by factor Xa, and abolishes amidolytic and coagulant activity," *J. Biol. Chem.* 271:30685-30691.

Bjoern et al., "Human plasma and recombinant factor VII. Characterization of O-glycosylations at serine residues 52 and 60 and effects of site-directed mutagenesis of serine 52 to alanine," *J. Biol. Chem.* 1991, 226(17):11051-11057.

Chang et al., "Engineered recombinant factor VII Q217 variants with altered inhibitor specificities," *Biochemistry* 1999, 38:10940-10948.

Chang et al., "Replacing the first epidermal growth factor-like domain of factor IX with that of factor VII enhances activity in vitro and in canine hemophilia B," *J. Clin. Invest.* 1997, 100(4), 886-892.

Cheung et al., "Localization of a metal-dependent epitope to the amino terminal residues 33-40 of human factor IX," *Thrombosis Res.* 1995, 80(5): 419-427.

EMBL Accession No. AF465270 (Feb. 2, 2003).

UNIPROT Accession No. P22457 (Aug. 1, 1991).

Dickinson et al., "Influence of cofactor binding and active site occupancy on the conformation of the macromolecular substrate exosite of factor VIIa," *J. Mol. Biol.* 1998, 277:959-971.

Dickinson et al., "Identification of surface residues mediating tissue factor binding and catalytic function of the serine protease factor VIIa," *Proc. Natl. Acad. Sci. USA* 1996, 93:14379-14384.

Hedner et al., "NovoSeven as a universal haemostatic agent," *Blood Coagulation & Fibrinolysis* 2000:11:107-111.

Higashi et al., "Molecular mechanism of tissue factor-mediated acceleration of factor VIIa activity," *J. Biol. Chem.* 1996, 271(43):26569-26574.

Huang et al., "Substrate Recognition by Tissue Factor-Factor VIIa. Evidence for interaction of residues Lys165 and Lys166 of tissue factor with the 4-carboxyglutamate-rich domain of factor X" *J. Biol. Chem.* 1996, 271(36):21752-21757.

Iakhiaev et al., "The Role of Catalytic Cleft & Exosite Residues of Factor VIIa for Complex Formation with Tissue Factor Pathway Inhibitor" *Thromobsis & Haemostasis* 2001, 85:458-463.

Iino et al., "Functional consequences of mutations in Ser-52 and Ser-60 in human blood coagulation factor VII," *Archives of Biochemistry and Biophysics* 1998, 352(2):182-192.

Jin et al., "Factor VIIa's first epidermal growth factor-like domain's role in catalytic activity," *Biochemistry* 1999, 38:1185-1192.

Jin et al., "Four loops of the catalytic domain of factor viia mediate the effect of the first EGF-like domain substitution on factor viia catalytic activity," *J. Mol. Biol.* 2001, 307:1503-1517.

Kelly et al., "$Ca^{2+}$ binding to the first epidermal growth factor module of coagulation factor VIIa is important for cofactor interaction and proteolytic function," *J. Biol. Chem.* 1997, 272(28):17467-17472.

Kemball-Cook et al., "Coagulation Factor VII $Gln_{100}$ Arg. Amino acid substitution at the epidermal growth factor 2-protease domain interface results in severely reduced tissue factor binding and procoagulant function," *J. Biol. Chem.* 1998, 273(14):8516-8521.

Leff, "Genetically stripped-down Factor VIII corrects bleeding disorder in homophiliac mice," *BioWorld Today* 1997, 8(209):1,6.

Leonard et al., "Activation and Active Site Occupation Alter Conformation in the Region of the First Epidermal Growth Factor-like Domains of Human Factor VII," *J. Biol. Chem.* 2000, 275(45):34894-34900.

Mayer, "Ultra-early hemostatic therapy for intracerebral hemorrhage," *Stroke* 2003, 34:224-229.

Nelsestuen, "Enhancement of Vitamin-K-Dependent Protein Function by Modification of the γ-Carboxyglutamic Acid Domain: Studies of Protein C and Factor VII," *Trends Cardiovasc. Med.* 1999, 9:162-167.

Nelsestuen et al., "Membrane association with multiple calcium ions: Vitamin-K-dependent proteins, annexins and pentraxins," *Curr. Opin. Struct. Biol.* 1999, 9:433-437.

Nelsestuen et al., "Vitamin K dependent proteins," in *Vitamins and Hormones*, Ed. Litwack, Academic Press, San Diego, CA, 2000, vol. 58, pp. 355-389.

Neuenschwander et al., "Alteration of the substrate and inhibitor specificities of blood coagulation," *Biochemistry* 1995, 34:8701-8707.

Osterlund et al., "Spectroscopic probing of the influence of calcium and the Gla domain on the interaction between the first EGF domain in Factor VII and tissue factor," *Eur. J. Biochem.*, 2000, 267:6204-6211.

Persson et al., "$Ca^{2+}$ binding to the first epidermal growth factor-like domain of factor VIIa increases amidolytic activity and tissue factor affinity," *J. Biol. Chem.* 1997, 272(32):19919-19924.

Persson, "Characterization of the interaction between the light chain of factor VIIa and tissue factor," *FEBS Letters* 1997, 413:359-363.

Petersen et al., "Binding of $Zn^{2+}$ to a $Ca^{2+}$ loop allosterically attenuates the activity of factor VIIa and reduces its affinity for tissue factor," *Protein Science* 2000, 9:859-866.

Petrovan et al., "Role of residue $Phe^{225}$ in the cofactor-mediated, allosteric regulation of the serine protease coagulation factor VIIa," *Biochemistry* 2000, 39:14457-14463.

Petrovan et al., "Residue $Met^{156}$ contributes to the labile enzyme conformation of coagulation factor VIIa," *J. Biol. Chem.* 2001, 276(9):6616-6620.

Shobe et al., "Regulation of the catalytic function of coagulation factor VIIa by a conformational linkage of surface residue Glu 154 to the active site," *Biochemistry* 1999, 38:2745-2751.

Shobe et al., "Macromolecular substrate affinity for the tissue factor-factor VIIa complex is independent of scissile bond docking," *J. Biol. Chem.* 1999, 274(34):24171-24175.

Sridhara et al., "Activation of a recombinant human factor VII structural analogue alters its affinity of binding to tissue factor," *Amer. J. Hemotology* 1996, 53:66-71.

Zhang et al., "Structure of extracellular tissue factor complexed with factor VIIa inhibited with a BPTI mutant," *J. Mol. Biol.* 285(5):2089-2104.

Sakai et al., "The γ-Carboxyglutamic Acid Domain of Human Factor VIIA is Essential for Its Interaction with Cell Surface Tissue Factor," *J. Biol. Chem.*, 1990, 265(4):1890-1894.

Nelsestuen, "Enhancement of vitamin-K-dependent protein function by modification of the γ-carboxyglutamic acid domain: studies of protein C and factor VII," *Trends Cardiovasc. Med.*, 1999, 9:162-167.

Nelsestuen and Ostrowski, "Membrane association with multiple calcium ions: vitamin-K-dependent proteins, annexins and pentraxins," *Curr. Opin. Struct. Biol.*, 1999, 9:433-437.

Nelsestuen et al., "Vitamin K-dependent proteins," *Vitamins and Hormones*, Litwack (ed.), 1999, vol. 58, pp. 355-389, Academic Press.

GenBank Accession No. K02059 1995.

GenBank Accession No. K02435 1993.

GenBank Accession No. M13232 1996.

Arnljots et al., "Prevention of experimental arterial thrombosis by topical administration of active site-inactivated factor VIIa," *J. Vasc. Surg.*, 1997, 25:341-346.

Bauer, "Treatment of Factor VII Deficiency with Recombinatn Factor VIIa," *Haemostasis*, 1996, 26(Suppl. 1):155-158.

Bodner et al., "The Pituitary-Specific Transcription Factor GHF-1 Is a Homeobox-Containing Protein," *Cell*, 1988, 55:505-518.

Bradford, "A Rapid and Sensitive Method for the Quantitation of Microgram Quantities of Protein Utilizing the Principle of Protein-Dye Binding," *Analyt. Biochem.*, 1976, 72:248-254.

Broze et al., "Monoclonal Anti-human Factor VII Antibodies," *J. Clin. Invest.*, 1985, 76:937-946.

Cheung and Stafford, "Localization of an Epitope of a Calcium-Dependent Monoclonal Antibody fo the N-Terminal Region of the GLA Domain of Human Factor VII," *Thromb. Res.*, 1995, 79(2):199-206.

Choudhri et al., "Targeted Inhibition of Intrinsic Coagulation Limits Cerebral Injury in Stroke without Increasing Intracerebral Hemorrhage," *J. Exp. Med.*, 1999, 190(1):91-99.

Christiansen et al., "Hydrophobic Amino Acid Residues of Human Anticoagulation Protein C That Contribute to Its Functional Binding to Phospholipid Vesicles," *Biochemistry*, 1995, 34:10376-10382.

Dackiw et al., "Prevention of Endotoxin-Induced Mortality by Antitissue Factor Immunization," *Arch. Surg.*, 1996, 131:1273-1278.

Dahlbäck, "Inherited Thrombophilia: Resistance to Activated Protein C as a Pathogenic Factor of Venous Thromboembolism," *Blood*, 1995, 85(3):607-614.

Dickinson and Ruf, "Active Site Modification of Factor VIIa Affects Interactions of the Protease Domain with Tissue Factor," *J. Biol. Chem.*, 1997, 272(32):19875-19879.

Esmon et al., "Isolation of a Membrane-bound Cofactor for Thrombin-catalyzed Activation of Protein C," *J. Biol. Chem.*, 1982, 257(2):859-864.

Evans and Nelsestuen, "Inportance of *cis*-Proline 22 in the Membrane-Binding Conformation of Bovine Prothrombin," *Biochemistry*, 1996, 35:8210-8215.

Evans and Nelsestuen, "How Important Are Proline 22 and the 41-45 Helical Stack to Membrane Binding by Bovine Prothrombin?" *Protein Sci.*, 1996, 5(Suppl. 1):163, Abstract No. 606-S.

Felgner et al., "Lipofection: A highly efficient, lipid-mediated DNA-transfection procedure," *Proc. Natl. Acad. Sci. USA*, 1987, 84:7413-7417.

Fiore et al., "The Biochemical Basis for the Apparent Defect of Soluble Mutant Tissue Factor in Enhancing the Proteolytic Activities of Factor VIIa," *J. Biol. Chem.*, 1994, 269(1):143-149.

Freedman et al., "Identification of the Phospholipid Binding Site in the Vitamin K-dependent Blood Coagulation Protein Factor IX," *J. Biol. Chem.*, 1996, 271(27): 16227-16236.

Han et al., "Isolation of a protein Z-dependent plasma protease inhibitor," *Proc. Natl. Acad. Sci. USA*, 1998, 95:9250-9255.

He et al., "Expression and functional characterization of chimeras between human and bovine vitamin-K-dependent protein-S-defining modules important for the species specificity of the activated protein C cofactor activity," *Eur. J. Biochem.*, 1995, 227:433-440.

Hedner et al., "Recombinant Activated Factor VII in the Treatment of Bleeding Episodes in Patients With Inherited and Acquired Bleeding Disorders," *Transfusion Medicine Reviews*, 1993, VII(2):78-83.

Hope et al., "Production of large unilamellar vesicles by a rapid extrusion procedure. Characterization of size distribution, trapped volume and ability to maintain a membrane potential," *Biochim. Biophys. Acta*, 1985, 812:55-65.

Hoskins et al., "Cloning and characterization of human liver cDNA encoding a protein S precursor," *Proc. Natl. Acad. Sci. USA*, 1987, 84:349-353.

Huang, "Studies on Phosphatidylcholine Vesicles, Formation and Physical Characteristics," *Biochemistry*, 1969, 8:344-352.

Humphries et al., "Chemical methods of protein synthesis and modification," *Curr. Opin. Biotechnol.*, 1991, 2:539-543.

Jurlander et al., "Recombinant Activated Factor VII (rFVIIa): Characterization, Manufacturing, and Clinical Development," *Semin. Thromb. Hemos.*, 2001, 27(4):373-383.

Lu and Nelsestuen, "The Prothrombinase Reaction: "Mechanism Switching" between Michaelis-Menten and Non-Michaelis-Menten Behaviors," *Biochemistry*, 1996, 35:8201-8209.

Lu and Nelsestuen, "Dynamic Features of Prothrombin Interaction with Phospholipid Vesicles of Different Size and Composition: Implications for Protein-Membrane Contact," *Biochemstry*, 1996, 35:8193-8200.

Martinez et al., "Underdecarboxlyation of Vitamin K-Dependent Proteins: Occasionally Severe, Possibly Universal," *Proceedings of the 49th ASMS Conference on Mass Spectrometry and Allied Topics*, May 27-31, 2001, Chicago, Illinois, 2 pgs.

Matsubara et al., "A Receptor Tyrosine Kinase, Sky, and Its Ligand Gas 6 Are Expressed in Gonads and Support Primordial Germ Cell Growth or Survival in Culture," *Dev. Biol.*, 1996, 180:499-510.

Mayer et al., "Prothrombin Association with Phospholipid Monolayers," *Biochemistry*, 1983, 22:316-321.

McDonald et al., "Comparison of Naturally Occurring Vitamin K-Dependent Proteins: Correlation of Amino Acid Sequences and Membrane Binding Properties Suggests a Membrane Contact Site," *Biochemistry*, 1997, 36(17):5120-5127.

McDonald et al., "Ionic Properties of Membrane Association by Vitamin K-Dependent Proteins: The Case for Univalency," *Biochemistry*, 1997, 36:15589-15598.

Morrissey et al., "Quantification of Activated Factor VII Levels in Plasma Using a Tissue Factor Mutant Selectively Deficient in Promoting Factor VII Activation," *Blood*, 1993, 81(3):734-744.

Muir and Kent, "The chemical synthesis of proteins," *Curr. Opin. Biotechnol.*, 1993, 4:420-427.

Nakagaki et al., "Initiation of the Extrinsic Pathway of Blood Coagulation: Evidence for the Tissue Factor Dependent Autoactivation of Human Coagulation Factor VII," *Biochemistry*, 1991, 30(45):10819-10824.

Nelsestuen and Suttie, "Properties of Asialo and Aglycoprothrombin," *Biochem. Biophys. Res. Comm.*, 1971, 45(1):198-203.

Nelsestuen and Lim, "Equilibria Involved in Prothrombin- and Blood-Clotting Factor X-Membrane Binding," *Biochemistry*, 1977, 16(19):4164-4171.

Nelsestuen et al., "Elevated Function of Blood Clotting Factor VIIa Mutants That Have Enhanced Affinity for Membranes," *J. Biol. Chem.*, 2001, 276(43):39825-39831.

Nicolaes et al., "A Protrhombinase-based Assay for Detection of Resistance to Activated Protein C," *Thromb. Haemost.*, 76:404-410.

Nicolaisen et al., "Immunological Aspects of Recombinant Factor VIIa (rFVIIa) in Clinical Use," *Thromb. Haemost.*, 1996, 76:200-204.

Perera et al., "*Trans-Cis* Isomerization of Proline 22 in Bovine Prothrombin Fragment 1: A Surprising Result of Structural Characterization," *Biochemistry*, 1998, 37:10920-10927.

Persson and Nielsen, "Site-directed mutagenesis but not γ-carboxylation of Glu-35 in factor VIIa affects the association with tissue factor," *FEBS Lett.*, 1996, 385:241-243.

Petersen et al., "Quenching of the Amidolytic Activity of One-Chain Tissue-Type Plasminogen Activator by Mutation of Lysine-416," *Biochemistry*, 1990, 29:3451-3457.

Ratcliffe et al., "The Importance of Specific γ-Carboxyglutamic Acid Residues in Prothrombin," *J. Biol. Chem.*, 1993, 268(32):24339-24345.

Resnick and Nelsestuen, "Prothrombin-Membrane Interaction. Effects of Ionic Strength, pH, and Temperature," *Biochemistry*, 1980, 19(13):3028-3033.

Rezaie and Esmon, "The Function of Calcium in Protein C Activation by Thrombin and the Thrombin-Thrombomodulin Complex Can Be Distinguished by Mutational Analysis of Protein C Derivatives," *J. Biol. Chem.*, 1992, 267(36):26104-26109.

Ruf et al., "Importance of Factor VIIa Gla-Domain Residue Arg-36 for Recognition of the Macromolecular Substrate Factor X Gla-Domain," *Biochemistry*, 1999, 38:1957-1966.

Schmidel et al., "Organization of the Human Protein S Genes," *Biochemistry*, 1990, 29:7845-7852.

Schulman et al., "Feasiblity of Using Recombinant Factor VIIa in Continuous Infusion," *Thromb. Haemost.*, 1996, 75:432-436.

Schwalbe et al., "Protein Structural Requirements and Properties of Membrane Binding by γ-Carboxyglutamic Acid-containing Plasma Proteins and Peptides," *J. Biol. Chem.*, 1989, 264(34):20288-20296.

Seshadri et al., "Differences in the Metal Ion Structure between Sr- and Ca-Prothrombin Fragment," *Biochemistry*, 1994, 33:1087-1092.

Shah et al., "Manipulation of the membrane binding site of vitamin K-dependent proteins: Enhanced biological function of human factor VII," *Proc. Natl. Acad. Sci. USA*, 1998, 95:4229-4234.

Shen et al., "Enhancing the Activity of Protein C by Mutagenesis To Improve the Membrane-Binding Site: Studies Related to Proline-10," *Biochemistry*, 1997, 36(51):16025-16031.

Shen et al., "Enhancement of Human Protein C Function by Site-directed Mutagenesis of the γ-Carboxyglutamic Acid Domain," *J. Biol. Chem.*, 1998, 273(47):31086-31091.

Smirnov et al., "A Chimeric Protein C Containing the Prothrombin Gla Domain Exhibits Increased Anticoagulant Activity and Altered Phospholipid Specificity," *J. Biol. Chem.*, 1998, 273(15):9031-9040.

Sørensen et al., "Incorporation of an Active Site Inhibitor in Factor VIIa Alters the Affinity for Tissue Factor," *J. Biol. Chem.*, 1997, 272(18):11863-11868.

Thariath and Castellino, "Highly conserved residue arginine-15 is required for the $Ca^{2+}$-dependent properties of the γ-carboxyglutamic acid domain of human antocoagulation Protein C and activated Protein C," *Biochem. J.*, 1997, 322:309-315.

Thim et al., "Amino Acid Sequence and Posttranslational Modification of Human Factor VII, from Plasma and Transfected Baby Hamster Kidney Cells," *Biochemistry*, 1988, 27:7785-7793.

Thomsen et al., "Pharmacokinetics of Recombinant Factor VIIa in the Rat—A Comparison of Bio-, Immuno- and Isotype Assays," *Thromb. Haemost.*, 1993, 70(3):458-464.

Vallette et al., "Construction of mutant and chimeric genes using the polymerase chain reaction," *Nucl. Acids Res.*, 1989, 17(2):723-733.

Vrana et al., "Expression of Tissue Factor in Tumor Stroma Correlates with Progression to Invasive Human Breast Cancer: Paracrine Regulation by Carcinoma Cell-derived Members of the Transforming Growth Factor β Family," *Cancer Res.*, 1996, 56:5063-5070.

Weber et al., "Modifications of Bovine Prothrombin Fragment 1 in the Presence and Absence of Ca(II) Ions," *J. Biol. Chem.*, 1992, 267(7):4564-4569.

Wei et al., "Kinetic and Mechanistic Analysis of Prothrombin-Membrane Binding by Stopped-Flow Light Scattering," *Biochemistry*, 1982, 21:1949-1959.

Welsch et al., "Chemical Modification of Prothrombin Fragment 1: Documentation of Sequential, Two-Stage Loss of Protein Function," *Biochemistry*, 1988, 27:4933-4938.

Welsch and Nelsestuen, "Amino-Terminal Alanine Functions in a Calcium-Specific Process Essential for Membrane Binding by Prothrombin Fragment 1," *Biochemistry*, 1988, 27:4939-4945.

Yan et al., "Characterization and Novel Purification of Recombinant Human Protein C from Three Mammalian Cell Lines," *Bio/Technology*, 1990, 8:655-661.

Zhang et al., "Role of Individual γ-Carboxyglutamic Acid Residues of Activated Human Protein C in Defining its In Vitro Anticoagulant Activity," *Blood*, 1992, 80(4):942-952.

Zhang and Castellino, "The Contributions of Individual γ-Carboxyglutamic Acid Residues in the Calcium-dependent Binding of Recombinant Human Protein C to Acidic Phospholipid Vesicles," *J. Biol. Chem.*, 1993, 268(16):12040-12045.

Zwaal et al., "Lipid-protection interactions in blood coagulation," *Biochim. Biophys. Acta*, 1998, 1376:433-453.

FIG. 14A
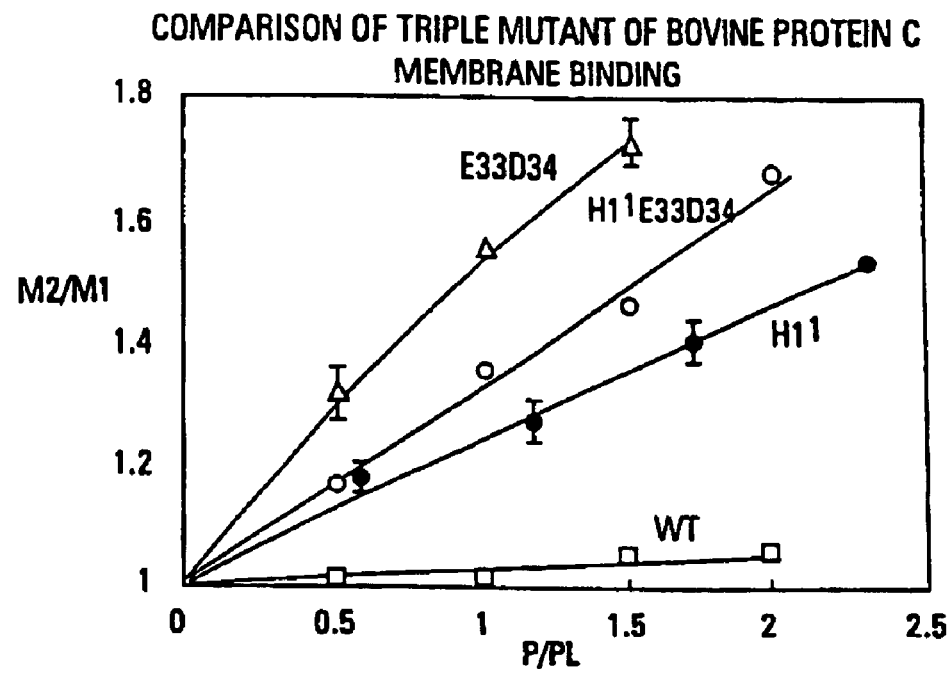
COMPARISON OF TRIPLE MUTANT OF BOVINE PROTEIN C MEMBRANE BINDING
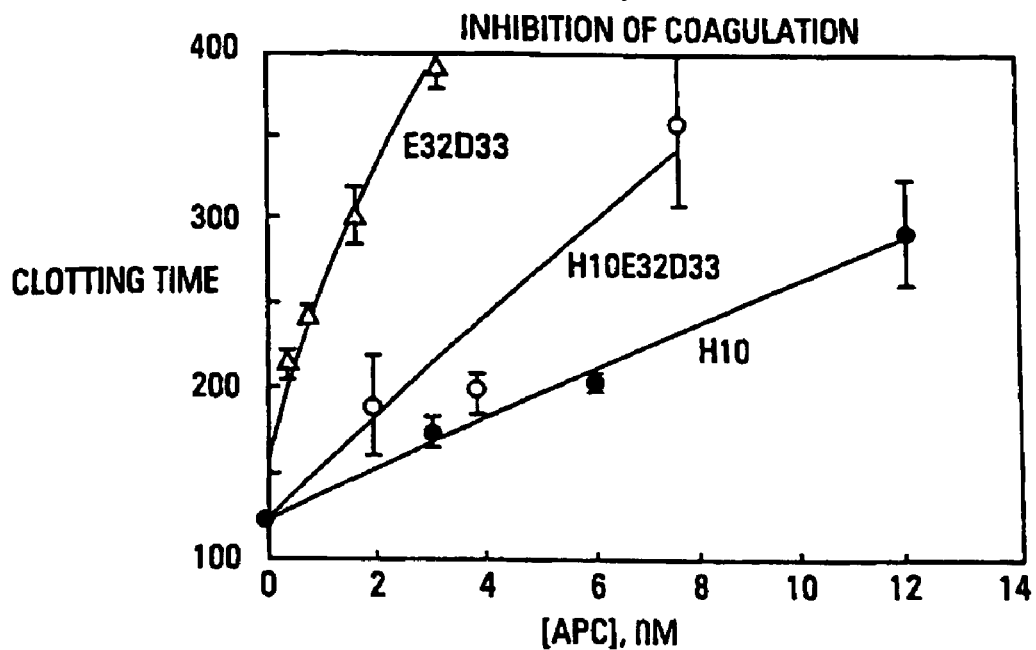
INHIBITION OF COAGULATION
FIG. 14B

SEQUENCE LISTING

```
<160> NUMBER OF SEQ ID NOS: 27

<210> SEQ ID NO 1
<211> LENGTH: 44
<212> TYPE: PRT
<213> ORGANISM: Homo sapiens
<220> FEATURE:
<221> NAME/KEY: VARIANT
<222> LOCATION: 6, 7, 14, 16, 19, 20, 25, 26, 29
<223> OTHER INFORMATION: Xaa = gamma carboxyglutamic or glutamic acid

<400> SEQUENCE: 1

Ala Asn Ser Phe Leu Xaa Xaa Leu Arg His Ser Ser Leu Xaa Arg Xaa
1               5                   10                  15

Cys Ile Xaa Xaa Ile Cys Asp Phe Xaa Xaa Ala Lys Xaa Ile Phe Gln
            20                  25                  30

Asn Val Asp Asp Thr Leu Ala Phe Trp Ser Lys His
        35                  40

<210> SEQ ID NO 2
<211> LENGTH: 44
<212> TYPE: PRT
<213> ORGANISM: Bos taurus
<220> FEATURE:
<221> NAME/KEY: VARIANT
<222> LOCATION: 6, 7, 14, 16, 19, 20, 23, 25, 26, 29, 35
<223> OTHER INFORMATION: Xaa = gamma carboxyglutamic acid or glutamic
      acid

<400> SEQUENCE: 2

Ala Asn Ser Phe Leu Xaa Xaa Leu Arg Pro Gly Asn Val Xaa Arg Xaa
1               5                   10                  15

Cys Ser Xaa Xaa Val Cys Xaa Phe Xaa Xaa Ala Arg Xaa Ile Phe Gln
            20                  25                  30

Asn Thr Xaa Asp Thr Met Ala Phe Trp Ser Phe Tyr
        35                  40
```

<210> SEQ ID NO 3
<211> LENGTH: 44
<212> TYPE: PRT
<213> ORGANISM: Homo sapiens
<220> FEATURE:
<221> NAME/KEY: VARIANT
<222> LOCATION: 6, 7, 14, 16, 19, 20, 25, 26, 29, 35
<223> OTHER INFORMATION: Xaa = gamma carboxyglutamic acid or glutamic acid

<400> SEQUENCE: 3

Ala Asn Ala Phe Leu Xaa Xaa Leu Arg Pro Gly Ser Leu Xaa Arg Xaa
 1               5                  10                  15

Cys Lys Xaa Xaa Gln Cys Ser Phe Xaa Xaa Ala Arg Xaa Ile Phe Lys
                20                  25                  30

Asp Ala Xaa Arg Thr Lys Leu Phe Trp Ile Ser Tyr
            35                  40

<210> SEQ ID NO 4
<211> LENGTH: 44
<212> TYPE: PRT
<213> ORGANISM: Bos taurus
<220> FEATURE:
<221> NAME/KEY: VARIANT
<222> LOCATION: 6, 7, 14, 16, 19, 20, 25, 26, 29, 34, 35
<223> OTHER INFORMATION: Xaa = gamma carboxyglutamic acid or glutamic acid

<400> SEQUENCE: 4

Ala Asn Gly Phe Leu Xaa Xaa Leu Arg Pro Gly Ser Leu Xaa Arg Xaa
 1               5                  10                  15

Cys Arg Xaa Xaa Leu Cys Ser Phe Xaa Xaa Ala His Xaa Ile Phe Arg
                20                  25                  30

Asn Xaa Xaa Arg Thr Arg Gln Phe Trp Val Ser Tyr
            35                  40

<210> SEQ ID NO 5
<211> LENGTH: 45
<212> TYPE: PRT
<213> ORGANISM: Homo sapiens
<220> FEATURE:
<221> NAME/KEY: VARIANT
<222> LOCATION: 7, 8, 15, 17, 20, 21, 26, 27, 30, 33, 36, 40
<223> OTHER INFORMATION: Xaa = gamma carboxyglutamic acid or glutamic acid

<400> SEQUENCE: 5

Tyr Asn Ser Gly Lys Leu Xaa Xaa Phe Val Gln Gly Asn Leu Xaa Arg
 1               5                  10                  15

Xaa Cys Met Xaa Xaa Lys Cys Ser Phe Xaa Xaa Ala Arg Xaa Val Phe
                20                  25                  30

Xaa Asn Thr Xaa Arg Thr Thr Xaa Phe Trp Lys Gln Tyr
            35                  40                  45

<210> SEQ ID NO 6
<211> LENGTH: 46
<212> TYPE: PRT
<213> ORGANISM: Bos taurus
<220> FEATURE:
<221> NAME/KEY: VARIANT
<222> LOCATION: 7, 8, 15, 17, 20, 21, 26, 27, 30, 33, 36, 41
<223> OTHER INFORMATION: Xaa = gamma carboxyglutamic acid or glutamic acid -continued

```
<400> SEQUENCE: 6

Tyr Asn Ser Gly Lys Leu Xaa Xaa Phe Val Gln Gly Asn Leu Xaa Arg
 1               5                   10                  15
Xaa Cys Met Xaa Xaa Lys Cys Ser Phe Xaa Xaa Ala Arg Xaa Val Phe
            20                  25                  30
Xaa Asn Thr Xaa Lys Arg Thr Thr Xaa Phe Trp Lys Gln Tyr
        35                  40                  45

<210> SEQ ID NO 7
<211> LENGTH: 36
<212> TYPE: DNA
<213> ORGANISM: Artificial Sequence
<220> FEATURE:
<223> OTHER INFORMATION: Primer

<400> SEQUENCE: 7
aaattaatac gactcactat agggagaccc aagctt                         36

<210> SEQ ID NO 8
<211> LENGTH: 42
<212> TYPE: DNA
<213> ORGANISM: Artificial Sequence
<220> FEATURE:
<223> OTHER INFORMATION: Primer

<400> SEQUENCE: 8
gcactcccgc tccaggctgc tgggacggag ctcctccagg aa                  42

<210> SEQ ID NO 9
<211> LENGTH: 36
<212> TYPE: DNA
<213> ORGANISM: Artificial Sequence
<220> FEATURE:
<223> OTHER INFORMATION: Primer

<400> SEQUENCE: 9
acgctccacg ttgccgtgcc gcagctcctc taggaa                         36

<210> SEQ ID NO 10
<211> LENGTH: 36
<212> TYPE: DNA
<213> ORGANISM: Artificial Sequence
<220> FEATURE:
<223> OTHER INFORMATION: Primer

<400> SEQUENCE: 10
ttcctagagg agctgcggca cggcaacgtg gagcgt                         36

<210> SEQ ID NO 11
<211> LENGTH: 36
<212> TYPE: DNA
<213> ORGANISM: Artificial Sequence
<220> FEATURE:
<223> OTHER INFORMATION: Primer

<400> SEQUENCE: 11
gcatttaggt gacactatag aatagggccc tctaga                         36

<210> SEQ ID NO 12
<211> LENGTH: 42
<212> TYPE: DNA
<213> ORGANISM: Artificial Sequence
<220> FEATURE:
<223> OTHER INFORMATION: Primer
```

```
<400> SEQUENCE: 12
gaaggccatt gtgtcttccg tgtcttcgaa aatctcccga gc                              42

<210> SEQ ID NO 13
<211> LENGTH: 36
<212> TYPE: DNA
<213> ORGANISM: Artificial Sequence
<220> FEATURE:
<223> OTHER INFORMATION: Primer

<400> SEQUENCE: 13
cagtgtgtca tccacatctt cgaaaatttc cttggc                                    36

<210> SEQ ID NO 14
<211> LENGTH: 36
<212> TYPE: DNA
<213> ORGANISM: Artificial Sequence
<220> FEATURE:
<223> OTHER INFORMATION: Primer

<400> SEQUENCE: 14
gccaaggaaa ttttcgaaga tgtggatgac acactg                                    36

<210> SEQ ID NO 15
<211> LENGTH: 36
<212> TYPE: DNA
<213> ORGANISM: Artificial Sequence
<220> FEATURE:
<223> OTHER INFORMATION: Primer

<400> SEQUENCE: 15
cagtgtgtca tccacatttt cgaaaatttc cttggc                                    36

<210> SEQ ID NO 16
<211> LENGTH: 36
<212> TYPE: DNA
<213> ORGANISM: Artificial Sequence
<220> FEATURE:
<223> OTHER INFORMATION: Primer

<400> SEQUENCE: 16
gccaaggaaa ttttcgaaaa tgtggatgac acactg                                    36

<210> SEQ ID NO 17
<211> LENGTH: 45
<212> TYPE: PRT
<213> ORGANISM: Bos taurus
<220> FEATURE:
<221> NAME/KEY: VARIANT
<222> LOCATION: 7, 8, 15, 17, 20, 21, 26, 27, 30, 33
<223> OTHER INFORMATION: Xaa = gamma carboxyglutamic acid or glutamic
      acid

<400> SEQUENCE: 17

Ala Asn Lys Gly Phe Leu Xaa Xaa Val Arg Lys Gly Asn Leu Xaa Arg
 1               5                  10                  15

Xaa Cys Leu Xaa Xaa Pro Cys Ser Arg Xaa Xaa Ala Phe Xaa Ala Leu
            20                  25                  30

Xaa Ser Leu Ser Ala Thr Asp Ala Phe Trp Ala Lys Tyr
        35                  40                  45

<210> SEQ ID NO 18
<211> LENGTH: 44
<212> TYPE: PRT
<213> ORGANISM: Bos taurus
```

-continued

```
<220> FEATURE:
<221> NAME/KEY: VARIANT
<222> LOCATION: 6, 7, 14, 16, 19, 20, 25, 26, 29, 32, 35, 39
<223> OTHER INFORMATION: Xaa = gamma carboxyglutamic acid or glutamic
      acid

<400> SEQUENCE: 18
```

Ala Asn Ser Phe Leu Xaa Xaa Val Lys Gln Gly Asn Leu Xaa Arg Xaa
1               5                   10                  15

Cys Leu Xaa Xaa Ala Cys Ser Leu Xaa Xaa Ala Arg Xaa Val Phe Xaa
            20                  25                  30

Asp Ala Xaa Gln Thr Asp Xaa Phe Trp Ser Lys Tyr
        35                  40

```
<210> SEQ ID NO 19
<211> LENGTH: 44
<212> TYPE: PRT
<213> ORGANISM: Homo sapiens
<220> FEATURE:
<221> NAME/KEY: VARIANT
<222> LOCATION: 6, 7, 14, 16, 19, 20, 25, 26, 29, 32, 36
<223> OTHER INFORMATION: Xaa = gamma carboxyglutamic acid or glutamic
      acid

<400> SEQUENCE: 19
```

Ala Asn Ser Leu Leu Xaa Xaa Thr Lys Gln Gly Asn Leu Xaa Arg Xaa
1               5                   10                  15

Cys Ile Xaa Xaa Leu Cys Asn Lys Xaa Xaa Ala Arg Xaa Val Phe Xaa
            20                  25                  30

Asn Asp Pro Xaa Thr Asp Tyr Phe Tyr Pro Lys Tyr
        35                  40

```
<210> SEQ ID NO 20
<211> LENGTH: 45
<212> TYPE: PRT
<213> ORGANISM: Homo sapiens
<220> FEATURE:
<221> NAME/KEY: VARIANT
<222> LOCATION: 7, 8, 11, 15, 17, 20, 21, 26, 27, 30, 33, 35, 40
<223> OTHER INFORMATION: Xaa = gamma carboxyglutamic acid or glutamic
      acid

<400> SEQUENCE: 20
```

Ala Gly Ser Tyr Leu Leu Xaa Xaa Leu Phe Xaa Gly Asn Leu Xaa Lys
1               5                   10                  15

Xaa Cys Tyr Xaa Xaa Ile Cys Val Tyr Xaa Xaa Ala Arg Xaa Val Phe
            20                  25                  30

Xaa Asn Xaa Val Val Thr Asp Xaa Phe Trp Arg Arg Tyr
        35                  40                  45

```
<210> SEQ ID NO 21
<211> LENGTH: 45
<212> TYPE: PRT
<213> ORGANISM: Bos taurus
<220> FEATURE:
<221> NAME/KEY: VARIANT
<222> LOCATION: 7, 8, 11, 15, 20, 21, 26, 27, 30, 33, 36, 40
<223> OTHER INFORMATION: Xaa = gamma carboxyglutamic acid or glutamic
      acid

<400> SEQUENCE: 21
```

Ala Gly Ser Tyr Leu Leu Xaa Xaa Leu Phe Xaa Gly His Leu Xaa Lys
1               5                   10                  15

```
Lys Cys Trp Xaa Xaa Ile Cys Val Tyr Xaa Xaa Ala Arg Xaa Val Phe
            20                  25                  30

Xaa Asp Asp Xaa Thr Thr Asp Xaa Phe Trp Arg Thr Tyr
            35                  40                  45

<210> SEQ ID NO 22
<211> LENGTH: 40
<212> TYPE: PRT
<213> ORGANISM: Homo sapiens
<220> FEATURE:
<221> NAME/KEY: MOD_RES
<222> LOCATION: 6, 7, 14, 16, 19, 20, 25, 26, 29, 35
<223> OTHER INFORMATION: Xaa = gamma carboxyglutamic acid

<400> SEQUENCE: 22

Ala Asn Ala Phe Leu Xaa Xaa Leu Arg Pro Gly Ser Leu Xaa Arg Xaa
1               5                   10                  15

Cys Lys Xaa Xaa Gln Cys Ser Phe Xaa Xaa Ala Arg Xaa Ile Phe Lys
            20                  25                  30

Asp Ala Xaa Arg Thr Lys Leu Phe
            35                  40

<210> SEQ ID NO 23
<211> LENGTH: 40
<212> TYPE: PRT
<213> ORGANISM: Artificial Sequence
<220> FEATURE:
<221> NAME/KEY: MOD_RES
<222> LOCATION: 6, 7, 14, 16, 19, 20, 25, 26, 29, 35
<223> OTHER INFORMATION: Xaa = gamma carboxyglutamic acid

<400> SEQUENCE: 23

Ala Asn Ala Phe Leu Xaa Xaa Leu Arg Gln Gly Ser Leu Xaa Arg Xaa
1               5                   10                  15

Cys Lys Xaa Xaa Gln Cys Ser Phe Xaa Xaa Ala Arg Xaa Ile Phe Lys
            20                  25                  30

Asp Ala Xaa Arg Thr Lys Leu Phe
            35                  40

<210> SEQ ID NO 24
<211> LENGTH: 40
<212> TYPE: PRT
<213> ORGANISM: Artificial Sequence
<220> FEATURE:
<221> NAME/KEY: MOD_RES
<222> LOCATION: 6, 7, 14, 16, 19, 20, 25, 26, 29, 32, 35
<223> OTHER INFORMATION: Xaa = gamma carboxyglutamic acid

<400> SEQUENCE: 24

Ala Asn Ala Phe Leu Xaa Xaa Leu Arg Pro Gly Ser Leu Xaa Arg Xaa
1               5                   10                  15

Cys Lys Xaa Xaa Gln Cys Ser Phe Xaa Xaa Ala Arg Xaa Ile Phe Xaa
            20                  25                  30

Asp Ala Xaa Arg Thr Lys Leu Phe
            35                  40

<210> SEQ ID NO 25
<211> LENGTH: 40
<212> TYPE: PRT
<213> ORGANISM: Artificial Sequence
<220> FEATURE:
<221> NAME/KEY: MOD_RES
<222> LOCATION: 6, 7, 14, 16, 19, 20, 25, 26, 29, 32, 35
<223> OTHER INFORMATION: Xaa = gamma carboxyglutamic acid
```

```
-continued

<400> SEQUENCE: 25

Ala Asn Ala Phe Leu Xaa Xaa Leu Arg Gln Gly Ser Leu Xaa Arg Xaa
 1               5                  10                  15

Cys Lys Xaa Xaa Gln Cys Ser Phe Xaa Xaa Ala Arg Xaa Ile Phe Xaa
            20                  25                  30

Asp Ala Xaa Arg Thr Lys Leu Phe
        35                  40

<210> SEQ ID NO 26
<211> LENGTH: 40
<212> TYPE: PRT
<213> ORGANISM: Artificial Sequence
<220> FEATURE:
<221> NAME/KEY: MOD_RES
<222> LOCATION: 6, 7, 14, 16, 19, 20, 25, 26, 29, 33, 35
<223> OTHER INFORMATION: Xaa = gamma carboxyglutamic acid

<400> SEQUENCE: 26

Ala Asn Ala Phe Leu Xaa Xaa Leu Arg Gln Gly Ser Leu Xaa Arg Xaa
 1               5                  10                  15

Cys Lys Xaa Xaa Gln Cys Ser Phe Xaa Xaa Ala Arg Xaa Ile Phe Lys
            20                  25                  30

Xaa Ala Xaa Arg Thr Lys Leu Phe
        35                  40

<210> SEQ ID NO 27
<211> LENGTH: 41
<212> TYPE: PRT
<213> ORGANISM: Artificial Sequence
<220> FEATURE:
<221> NAME/KEY: MOD_RES
<222> LOCATION: 7, 8, 15, 17, 20, 21, 26, 27, 30, 33, 35, 36
<223> OTHER INFORMATION: Xaa = gamma carboxyglutamic acid

<400> SEQUENCE: 27

Ala Asn Ala Tyr Phe Leu Xaa Xaa Leu Arg Gln Gly Ser Leu Xaa Arg
 1               5                  10                  15

Xaa Cys Lys Xaa Xaa Gln Cys Ser Phe Xaa Xaa Ala Arg Xaa Ile Phe
            20                  25                  30

Xaa Phe Xaa Xaa Arg Thr Lys Leu Phe
        35                  40
```

MODIFIED VITAMIN K-DEPENDENT POLYPEPTIDES

CROSS-REFERENCE TO RELATED APPLICATIONS

This application is a divisional of U.S. Ser. No. 10/298,330, filed Nov. 18, 2002, now U.S. Pat. No. 7,247,708, which is a continuation-in-part of U.S. Ser. No. 09/497,591, filed Feb. 3, 2000, now U.S. Pat. No. 6,747,003, which is a continuation-in-part of U.S. Ser. No. 09/302,239, filed on Apr. 29, 1999, now U.S. Pat. No. 6,693,075, which is a continuation-in-part of U.S. Ser. No. 08/955,636, filed on Oct. 23, 1997, now U.S. Pat. No. 6,017,882.

STATEMENT AS TO FEDERALLY-SPONSORED RESEARCH

Funding for work described herein was provided by the National Institutes of Health, grant no. HL15728. The federal government, has certain rights in the invention.

BACKGROUND OF THE INVENTION

Vitamin K-dependent proteins contain 9 to 13 gamma-carboxyglutamic acid residues (Gla) in their amino terminal 45 residues. The Gla residues are produced by enzymes in the liver that utilize vitamin K to carboxylate the side chains of glutamic acid residues in protein precursors. Vitamin K-dependent proteins are involved in a number of biological processes, of which the most well described is blood coagulation (reviewed in Furie and Furie, 1988, *Cell*, 53:505-518). Vitamin K-dependent proteins include protein Z, protein S, prothrombin, factor X, factor IX, protein C, factor VII, and Gas6. The latter protein functions in cell growth regulation. Matsubara et al., 1996, *Dev. Biol.*, 180:499-510. The Gla residues are needed for proper calcium binding and membrane interaction by these proteins. The membrane contact site of factor X is thought to reside within amino acid residues 1-37. Evans and Nelsestuen, 1996, *Protein Sci.*, 5:suppl. 1, 163 Abs. Although the Gla-containing regions of the plasma proteins show a high degree of sequence homology, they have at least a 1000-fold range in membrane affinity. McDonald et al., 1997, *Biochemistry*, 36:5120-5137.

Factor VII functions in the initial stage of blood clotting and may be a key element in forming blood clots. The inactive precursor, or zymogen, has low enzyme activity that is greatly increased by proteolytic cleavage at the R152I153 bond to form factor VIIa. This activation can be catalyzed by factor Xa as well as by VIIa-tissue factor, an integral membrane protein found in a number of cell types. Fiore et al., 1994, *J. Biol. Chem.*, 269:143-149. Activation by VIIa-tissue factor is referred to as autoactivation. It is implicated in both the activation (formation of factor VIIa from factor VII) and the subsequent activity of factor VIIa. The most important pathway for activation in vivo is not known. Factor VIIa can activate blood-clotting factors IX and X.

Tissue factor is expressed at high levels on the surface of some tumor cells. A role for tissue factor, and for factor VIIa, in tumor development and invasion of tissues is possible. Vrana et al., *Cancer Res.*, 56:5063-5070. Cell expression and action of tissue factor is also a major factor in toxic response to endotoxic shock. Dackiw et al., 1996, *Arch. Sure.*, 131: 1273-1278.

Protein C is activated by thrombin in the presence of thrombomodulin, an integral membrane protein of endothelial cells. Esmon et al., 1982, *J. Biol. Chem.*, 257:859-864. Activated protein C (APC) degrades factors Va and VIIIa in combination with its cofactor, protein S. Resistance to APC is the most common form of inherited thrombosis disease. Dahlback, 1995, *Blood,* 85:607-614. Vitamin K inhibitors are commonly administered as a prophylaxis for thrombosis disease.

Vitamin K-dependent proteins are used to treat certain types of hemophilia. Hemophilia A is characterized by the absence of active factor VIII, factor VIIa, or the presence of inhibitors to factor VIII. Hemophilia B is characterized by the absence of active factor IX, factor IXa. Factor VII deficiency, although rare, responds well to factor VII administration. Bauer, 1996, *Haemostasis,* 26:155-158, suppl. 1. Factor VIII replacement therapy is limited due to development of high-titer inhibitory factor VIII antibodies in some patients. Alternatively, factor VIIa can be used in the treatment of hemophilia A and B. Factor IXa and factor VIIIa activate factor X. Factor VIIa eliminates the need for factors IX and VIII by activating factor X directly, and can overcome the problems of factor IX and VIII deficiencies with few immunological consequences. Hedner et al., 1993, *Transfus. Medi. Rev.,* 7:78-83; Nicolaisen et al., 1996, *Thromb. Haemost.,* 76:200-204. Effective levels of factor VIIa administration are often high (45 to 90 µg/kg of body weight) and administration may need to be repeated every few hours. Shulmav et al., 1996, *Thromb. Haemost.,* 75:432-436.

A soluble form of tissue factor (soluble tissue factor or sTF) that does not contain the membrane contact region has been found to be efficacious in treatment of hemophilia when co-administered with factor VIIa. See, for example, U.S. Pat. No. 5,504,064. In dogs, sTF was shown to reduce the amount of factor VIIa needed to treat hemophilia Membrane association by sTF-VIIa is entirely dependent on the membrane contact site of factor VII. This contrasts to normal tissue-factor VIIa complex, which is bound to the membrane through both tissue factor and VII (a).

SUMMARY OF THE INVENTION

It has been discovered that modifications within the γ-carboxyglutamic acid (GLA) domain of vitamin K-dependent polypeptides enhance their membrane binding affinities. Vitamin K-dependent polypeptides modified in such a manner have enhanced activity and may be used as anti-coagulants, pro-coagulants, or for other functions that utilize vitamin K-dependent proteins. For example, an improved factor VII molecule may provide several benefits by lowering the dosage of VIIa needed, reducing the relative frequency of administration and/or by providing qualitative changes that allow more effective treatment of deficiency states.

The invention features vitamin K-dependent polypeptides that include a modified GLA domain that enhances membrane-binding affinity of the polypeptide relative to a corresponding native vitamin K-dependent polypeptide. In some embodiments, activity of the vitamin K-dependent polypeptide also is enhanced. The modified GLA domain can be from about amino acid 1 to about amino acid 45 and can include at least one amino acid substitution. For example, the amino acid substitution can be at amino acid 2, 5, 9, 11, 12, 29, 33, 34, 35, or 36, and combinations thereof. In particular, the substitution can be at amino acid 34, amino acids 11, 12, 29, 33, or 34, amino acids 2, 5, or 9, amino acids 11 or 12, amino acids 29 or 33, or amino acids 34, 35, or 36. The modified GLA domain may include an amino acid sequence, which, in the calcium saturated state, forms a tertiary structure having a cationic core with a halo of electronegative charge.

The vitamin K-dependent polypeptide may be, for example, protein C, activated protein C, factor IX, factor IXa or active site modified factor IXa, factor VII, factor VIIa or active site modified factor VIIa, protein S, protein Z, or factor Xa or active site modified Xa. The modified GLA domain of protein C or activated protein C may include substitution of a glycine residue at amino acid 12. Further substitutions in the GLA domain of protein C or activated protein C can include a glutamic acid residue at amino acid 33 and an aspartic acid or glutamic acid residue at amino acid 34, a glutamine or glutamic acid residue at amino acid 11, a phenylalanine residue at amino acid 29, an aspartic or glutamic acid residue at amino acid 35, or a glutamic acid residue at amino acid 36. The modified GLA domain of factor VII, factor VIIa, and active site modified factor VIIa may contain a substitution at amino acid 34, a substitution at amino acid 35, or a substitution at amino acids 11 and 33. For example, a modified GLA domain can include a glutamic acid residue at amino acid 34, or an aspartic acid or glutamic acid residue at amino acid 35. In another example, a glutamine residue at amino acid 11 and a glutamic acid residue at amino acid 33 may be substituted.

The modified GLA domain of protein S can include a substitution of an isoleucine, leucine, valine, or phenylalanine residue at amino acid 9. Further substitutions can include an aspartic acid or glutamic acid residue at amino acid 34 or 35. The modified GLA domain also can contain a phenylalanine residue at amino acid 5, and further can include a substitution in the thrombin-sensitive loop, such as at amino acid 49, 60, or 70. The modified GLA domain of active site modified Factor IXa can include a phenylalanine residue at amino acid 29, a phenylalanine, leucine, or isoleucine residue at amino acid 5, or an aspartic acid or glutamic acid residue at amino acids 34 or 35, and combination thereof.

The modified GLA domain of active site modified Factor Xa can include a glutamine at amino acid 11, a glutamic acid residue at amino acid 34, or an aspartic acid or glutamic acid residue at amino acid 35. The modified GLA domain of protein Z can include an asparagine or glutamine residue at amino acid 2 or an aspartic acid or glutamic acid residue at amino acid 34, 35, or 36.

The modified GLA domain of vitamin K-dependent polypeptides further can include an inactivated cleavage site. For example, factor VII can include an inactivated cleavage site, such as a substitution of an alanine residue at amino acid 152.

In another aspect, the invention features a vitamin K-dependent polypeptide that includes a modified GLA domain that enhances membrane binding affinity and activity of the polypeptide. The modified GLA domain of such a polypeptide includes at least one amino acid insertion at amino acid 4. The polypeptide can be factor VII or VIIa, protein C or activated protein C, factor X or Xa, or protein S. For example, the polypeptide can be factor VII or IIa, and can include the insertion of a tyrosine or glycine residue.

The invention also features a mammalian host cell that includes a vitamin K-dependent polypeptide. The polypeptide includes a modified GLA domain that enhances membrane-binding affinity of the polypeptide relative to a corresponding native vitamin K-dependent polypeptide. The modified GLA domain includes at least one amino acid substitution as described above (e.g., a glutamic acid residue substituted at position 34). The vitamin K-dependent polypeptide may be, for example, factor VII or factor VIIa.

The invention also relates to a pharmaceutical composition that includes a pharmaceutically acceptable carrier and an amount of a vitamin K-dependent polypeptide effective to inhibit clot formation in a mammal. The vitamin K-dependent polypeptide includes a modified GLA domain that enhances membrane-binding affinity of the polypeptide relative to a corresponding native vitamin K-dependent polypeptide. In some embodiments, activity of the polypeptide also is enhanced. The modified GLA domain includes at least one amino acid substitution (e.g., a glutamic acid residue substituted at position 34). The vitamin K-dependent polypeptide may be, for example, protein C, activated protein C or active site modified factor VIIa, protein S, or active site modified factor IXa. The composition can include an anticoagulant agent (e.g. aspirin).

The invention also features a pharmaceutical composition that includes a pharmaceutically acceptable carrier and an amount of a vitamin K-dependent polypeptide effective to increase clot formation in a mammal. The vitamin K-dependent polypeptide includes a modified GLA domain that enhances membrane-binding affinity of the polypeptide relative to a corresponding native vitamin K-dependent polypeptide. The modified GLA domain includes at least one amino acid substitution (e.g., a glutamic acid residue substituted at position 34). The vitamin K-dependent polypeptide may be, for example, factor VII, factor VIIa, factor IX or factor IXa. The pharmaceutical composition may also include soluble tissue factor.

A method of decreasing clot formation in a mammal is also described. The method includes administering an amount of a vitamin K-dependent polypeptide effective to decrease clot formation in the mammal. The vitamin K-dependent polypeptide includes a modified GLA domain that enhances membrane-binding affinity of the polypeptide relative to a corresponding native vitamin K-dependent polypeptide. In some embodiments, activity of the polypeptide also is enhanced. The modified GLA domain includes at least one amino acid substitution (e.g., a glutamic acid substituted at position 34). The vitamin K-dependent polypeptide may be, for example, protein C, activated protein C or active site modified factor VIIa or factor IXa, or protein S.

The invention also features a method of increasing clot formation in a mammal. The method includes administering an amount of a vitamin K-dependent polypeptide effective to increase clot formation in the mammal. The vitamin K-dependent polypeptide includes a modified GLA domain that enhances membrane-binding affinity of the polypeptide relative to a corresponding native vitamin K-dependent polypeptide. The modified GLA domain includes at least one amino acid substitution (e.g., a glutamic acid residue substituted at position 34). The vitamin K-dependent polypeptide may be, for example, factor VII, factor VIIa, factor IX or factor IXa.

In another aspect, the invention features a method for identifying a vitamin K-dependent polypeptide having enhanced membrane binding affinity and activity. The method includes modifying the GLA domain of the polypeptide, wherein modifying includes substituting at least one amino acid in the GLA domain; monitoring membrane binding affinity and activity of the polypeptide having the modified GLA domain; and identifying the modified vitamin K-dependent polypeptide as having enhanced membrane binding affinity and activity if membrane binding affinity activity of the modified polypeptide is enhanced relative to a corresponding native vitamin K-dependent polypeptide. Suitable substitutions are described above. The polypeptide can increase clot formation or inhibit clot formation.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following drawings and detailed description, and from the claims.

BRIEF DESCRIPTION OF THE DRAWINGS

FIG. 14 compares membrane binding (Panel A) and coagulation inhibition (Panel B) with wild-type (open squares), H111 (filled circles), E33D34 (open triangles) and the triple H11E33D34 mutant (open circles) of bovine protein C.

FIG. 19 is a dot plot comparing the activation of factor X by FVIIa variants. Filled circles, E33-VIIa; open circles, Q11E33-VIIa; open triangles, Q11E34-VIIa; filled squares, (Y4)Q11E33F34E35-VIIa.

DETAILED DESCRIPTION

Figure 1A:
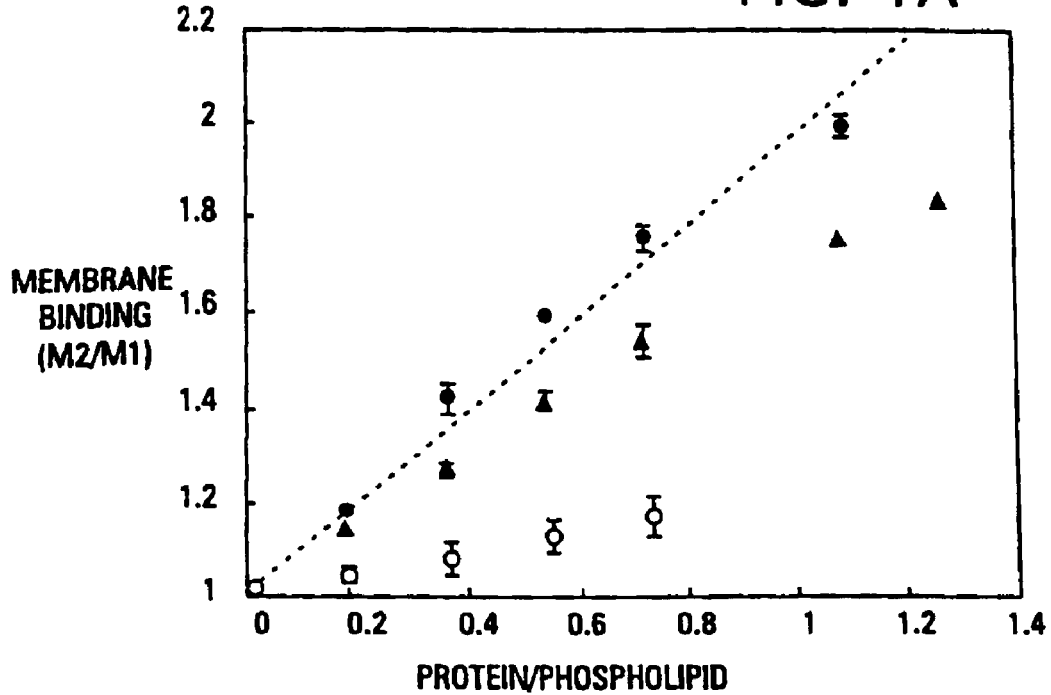
FIG. 1 depicts the binding, with standard deviations, of wild type VIIa (open circles), VIIQ11E33 (filled circles), and bovine factor X (filled triangles) to membranes.

In one aspect, the invention features a vitamin K-dependent polypeptide including a modified GLA domain with enhanced membrane binding affinity relative to a corresponding native vitamin K-dependent polypeptide. Activity of the vitamin K-dependent polypeptide also can be enhanced. Vitamin K-dependent polypeptides are a group of proteins that utilize vitamin K in their biosynthetic pathway to carboxylate the side chains of glutamic acid residues in protein precursors. The GLA domain contains 9-13 γ-carboxyglutamic acid residues in the N-terminal region of the polypeptide, typically from amino acid 1 to about amino acid 45. Protein Z, protein S, factor X, factor II (prothrombin), factor IX, protein C, factor VII and Gas6 are examples of vitamin K-dependent polypeptides. Amino acid positions of the polypeptides discussed herein are numbered according to factor IX. Protein S, protein C, factor X, factor VII, and human prothrombin all have one less amino acid (position 4) and must be adjusted accordingly. For example, actual position 10 of bovine protein C is a proline, but is numbered herein as amino acid 11 for ease of comparison throughout. As used herein, the term "polypeptide" is any chain of amino acids, regardless of length or post-translational modification. Amino acids have been designated herein by standard three letter and one-letter abbreviations.

Modifications of the GLA domain include at least one amino acid substitution (e.g., one to 10 substitutions). The substitutions may be conservative or non-conservative. Conservative amino acid substitutions replace an amino acid with an amino acid of the same class, whereas non-conservative amino acid substitutions replace an amino acid with an amino acid of a different class. Non-conservative substitutions may result in a substantial change in the hydrophobicity of the polypeptide or in the bulk of a residue side chain. In addition, non-conservative substitutions may make a substantial change in the charge of the polypeptide, such as reducing electropositive charges or introducing electronegative charges. Examples of non-conservative substitutions include a basic amino acid for a non-polar amino acid, or a polar amino acid for an acidic amino acid. The amino acid substitution may be at amino acid 2, 5, 9, 11, 12, 29, 33, 34, 35, or 36, and combinations thereof. The modified GLA domain may include an amino acid sequence, which, in the calcium-saturated state, contributes to formation of a tertiary structure having a cationic core with a halo of electronegative charge. The highest affinity proteins show an electronegative charge extending to amino acids 35 and 36. Without being bound by a particular theory, enhanced membrane affinity may result from a particular electrostatic pattern consisting of an electropositive core completely surrounded by an electronegative surface.

In addition, modifications of the GLA domain can include an insertion of a residue at position four of a vitamin K-dependent polypeptide. Suitable polypeptides lack an amino acid at this position (protein S, protein C, factor X, factor VII, and human prothrombin), based on sequence alignments of vitamin K-dependent polypeptides.

Many vitamin K-dependent polypeptides are substrates for membrane-bound enzymes. Since no vitamin K-dependent polypeptides display the maximum potential membrane-binding affinity of a GLA domain, all must contain amino acids whose purpose is to reduce binding affinity. Consequently, many vitamin K-dependent polypeptides contain amino acids that are non-optimal from the standpoint of maximum membrane-binding affinity. These residues effectively disrupt the binding site to provide a more rapid turnover for an enzymatic reaction.

Lowered-membrane affinity may serve several purposes. High affinity is accompanied by slow exchange, which may limit reaction rates. For example, when the prothrombinase enzyme is assembled on membranes with high affinity for substrate, protein exchange from the membrane, rather than enzyme catalysis, is the limiting step. Lu and Nelsestuen, 1996, *Biochemistry*, 35:8201-8209. Alternatively, adjustment of membrane affinity by substitution with non-optimum amino acids may balance the competing processes of procoagulation (factor X, IX, VII, and prothrombin) and anticoagulation (protein C, S). Although membrane affinities of native proteins may be optimal for normal states, enhancement of membrane affinity can produce proteins that are useful for in vitro study as well as improved therapeutics for regulating blood clotting in pathological conditions in vivo.

Various examples of GLA domain modified vitamin K-dependent polypeptides are described below.

The vitamin K-dependent polypeptide may be protein C or activated protein C (APC). Amino acid sequences of the wild-type human (hC, SEQ ID NO:1) and bovine (bC, SEQ ID NO:2) protein C GLA domains are shown in Table 1. X is a Gla or Glu residue. In general, a protein with neutral (e.g., Q) or anionic residues (e.g., D, E) at positions 11, 33, 34, 35, and 36 will have higher membrane affinity.

TABLE 1 hC:
ANS-FLXXLRH$_{11}$SSLXRXCIXX$_{21}$ICDFXXAKXI$_{31}$FQNVDDTLAF$_{41}$WSKH bC:
ANS-FLXXLRP$_{11}$GNVXRXCSXX$_{21}$VCXFXXARXI$_{31}$FQNTXDTMAF$_{41}$WSFY

The GLA domain of protein C or APC can contain a substitution at amino acids 11, 12, 29, 33, 34, 35, or 36, and combinations thereof. For example, the modified GLA domain may include a substitution at amino acid 12 of a glycine residue for serine, and further may include a glutamic acid residue at amino acid 33 and an aspartic acid or glutamic acid residue at amino acid 34. The glutamic acid at position 33 may be further modified to γ-carboxyglutamic acid in vivo. For optimum activity, the modified GLA domain may include an additional substitution at amino acid 11. For example, a glutamine residue may be substituted at amino acid 11 or alternatively, a glutamic acid or an aspartic acid residue may be substituted. A histidine residue also may be substituted at amino acid 11 in bovine protein C. Replacement of amino acid 29 by phenylalanine, the amino acid found in prothrombin, is another useful modification. Glutamic acid or aspartic acid residues also can be substituted at amino acid 35. The GLA domain of protein C or activated protein C also can contain a glutamic acid substitution for asparagine at position 34, in the presence or absence of other substitutions. Modified protein C with enhanced membrane binding affinity may be used in place of, or in combination with, other injectable anticoagulants such as heparin. Heparin is typically used in most types of surgery, but suffers from a low efficacy/toxicity ratio. In addition, modified protein C with enhanced membrane affinity may be used in place of, or in combination with, oral anticoagulants, including aspirin and anticoagulants in the coumarin family, such as warfarin.

These modifications also can be made with active site modified APC. The active site of APC may be inactivated chemically, for example by N-dansyl-glutamyl glycylarginylchloromethylketone (DEGR), phenylalanyl-phenylalanyl arginylchloromethylketone (FFR), or by site-directed mutagenesis of the active site. Sorensen et al., 1997, *J. Biol. Chem.*, 272:11863-11868. Active site modified APC functions as an inhibitor of the prothrombinase complex. Enhanced membrane affinity of active site modified APC may result in a more therapeutically effective polypeptide.

The vitamin K-dependent polypeptide may be factor VII or the active form of factor VII, factor VIIa Native or naturally occurring factor VII polypeptide has low affinity for membranes. Amino acid sequences of the wild-type human (VII, SEQ ID NO: 3) and bovine (bVII, SEQ ID NO: 4) factor VII GLA domains are shown in Table 2.

TABLE 2 hVII:
ANA-FLXXLRP$_{11}$GSLXRXCKXX$_{21}$QCSFXXARXI$_{31}$FKDAXRTKLF$_{41}$WISY bVII:
ANG-FLXXLRP$_{11}$GSLXRXCRXX$_{21}$LCSFXXAHXI$_{31}$FRNXXRTRQF$_{41}$WVSY

The GLA domain of factor VII or VIIa can contain a substitution, for example at amino acid 11, 29, 33, 34, or 35, and combinations thereof. The modified GLA domain of factor VII or factor VIIa may include, for example, a glutamic acid, a glutamine, an asparagine, or an aspartic acid residue at amino acid 11, a phenylalanine or a glutamic acid residue at amino acid 29, or an aspartic acid or a glutamic acid residue at amino acid 33 or 35. Other neutral residues also may be substituted at these positions. The modified GLA domain can include combinations of such substitutions at amino acid residues 11 and 29, at residues 11 and 33, at residues 11 and 35, at residues 11, 33, and 35, at residues 11, 29, and 33, at residues 11, 29, 33, and 35, at residues 29 and 33, at residues 29 and 35, or at residues 29, 33, and 35. For example, the GLA domain of factor VII or factor VIIa may include a glutamine residue at amino acid 11 and a glutamic acid residue at amino acid 33, or a glutamine residue at amino acid 11 and a phenylalanine residue at amino acid 29. The modified GLA domain also may include a substitution at amino acid 34, either alone or in combination with one or more substitutions at positions 11, 29, 33, and 35. For example, a glutamic acid or a phenylalanine residue can be substituted at amino acid 34. In addition, the modified GLA domain can include an insertion at position 4 alone (e.g, a tyrosine or glycine residue) or in combination with substitutions described above.

Factor VII or VIIa modified in these manners has a much higher affinity for membranes than the native or wild type polypeptide. It also has a much higher activity in autoactivation, in factor Xa generation, and in several blood clotting assays. Activity is particularly enhanced at marginal coagulation conditions, such as low levels of tissue factor and/or phospholipid. For example, modified factor VII is about 4 times as effective as native VIIa at optimum thromboplastin levels, but is about 20-fold as effective at 1% of optimum thromboplastin levels. Marginal pro-coagulation signals are probably most predominant in vivo. Presently available clotting assays that use optimum levels of thromboplastin cannot detect clotting time differences between normal plasma and those from hemophilia patients. Clotting differences between such samples are only detected when non-optimal levels of thromboplastin or dilute thromboplastin are used in clotting assays.

A benefit of a mutant containing a glutamic acid at position 34 (mutant E34) as compared to a mutant containing a glutamic acid at position 33 (mutant B33) is lowered antigenicity. Changing the cationic lysine at position 33 to Gla alters the charge from +1 to −2, a change that could elicit antibody production in an individual (e.g., an individual having hemophilia) who must be treated frequently with the mutant protein. A mutation from aspartic acid to glutamic acid at position 34, on the other hand, converts the site from a −1 state to a −2 state, maintaining charge of the same sign and altering the total protein only very slightly.

Another example of a vitamin K-dependent polypeptide is active site modified factor VIIa. The active site of factor VIIa may be modified chemically, for example by DEGR, FFR, or by site-directed mutagenesis of the active site. DEGR-modified factor VII is an effective inhibitor of coagulation by several routes of administration. Amljots et al., 1997, *J. Vasc. Surg.*, 25:341-346. Modifications of the GLA domain may make active site modified Factor VIIa more efficacious. Suitable substitutions or insertions are described above.

The vitamin K-dependent polypeptide may also be factor IX or the active form of factor IX, factor IXa. As with active site modified factor VIIa, active site modified IXa may be an inhibitor of coagulation. Active site modified factor IXa can bind its cofactor, factor VIII, but will not form blood clots. Active site modified factor IXa (wild-type) prevents coagulation without increase of bleeding in an animal model of stroke. See, for example, Choudhri et al., *J. Exp. Med.* 1999, 190:91-99.

Amino acid sequences of the wild-type human (hIX, SEQ ID NO:5) and bovine (bIX, SEQ ID NO:6) factor IX GLA domains are shown in Table 3. For example, a valine, leucine, phenylalanine, or isoleucine residue may be substituted at amino acid 5, an aspartic acid or glutamic acid residue may be substituted at amino acid 11, a phenylalanine residue at amino acid 29, or an aspartic acid or glutamic acid residue at amino acids 34 or 35, and combinations thereof.

TABLE 3 hIX:
YNSGKLXXFVQ$_{11}$GNLXRXCMXX$_{21}$KCSFXXARXV$_{31}$FXNTXRTTXF$_{41}$WKQY bIX:
YNSGKLXXFVQ$_{11}$GNLXRXCMXX$_{21}$KCSFXXARXV$_{31}$FXNTXKRTTXF$_{41}$WKQY

A further example of a vitamin K-dependent polypeptide is protein S. The amino acid sequence of human protein S (hPS, SEQ ID NO:19) is shown in Table 4. The modified GLA domain of Protein S can have, for example, a substitution at amino acid 5, 9, 34, or 35, and combinations thereof. For example, a phenylalanine can be substituted at amino acid 5, an isoleucine, leucine, valine, or phenylalanine residue at amino acid 9, or an aspartic acid or glutamic acid residue at amino acid 34 or 35. In addition to the at least one substitution in the GLA domain, protein S further can include a substitution in the thrombin sensitive loop. In particular, residues 49, 60, or 70 of the thrombin sensitive loop, which each are arginine residues, can be replaced with, for example, alanine residues.

TABLE 4 hPS:
ANS-LLXXTKQ$_{11}$GNLXRXCIXX$_{21}$LCNKXXARXV$_{31}$FXNDPXTDYF$_{41}$YPKY

The vitamin K-dependent polypeptides of the invention also can include an inactivated cleavage site such that the polypeptides are not converted to an active form. For example, factor VII containing an inactivated cleavage site would not be converted to factor VIIa, but would still be able to bind tissue factor. In general, an arginine residue is found at the cleavage site of vitamin K-dependent polypeptides. Any residue can be substituted for the arginine at this position to inactivate the cleavage site. In particular, an alanine residue could be substituted at amino acid 152 of factor VII. Vitamin K-dependent polypeptides of the invention that further contain an inactivated cleavage site act as inhibitors.

In another aspect, the invention features a mammalian host cell including a vitamin K-dependent polypeptide having a modified GLA domain that enhances membrane-binding affinity of the polypeptide relative to a corresponding native vitamin K-dependent polypeptide. Activity of the vitamin K-dependent polypeptides can be enhanced in some embodiments. Suitable vitamin K-dependent polypeptides and modifications of the GLA domain are discussed above. The mammalian host cell may include, for example, modified factor VII or modified factor VIIa. The GLA domain of modified factor VII or modified factor VIIa may contain an amino acid substitution at amino acid 11 and at amino acid 33. Preferably, the amino acid substitution includes a glutamine residue at amino acid 11 and a glutamic acid residue at amino acid 33 of factor VII or VIIa. Alternatively, the GLA domain can contain an amino acid substitution at amino acid 34 (e.g., a glutamic acid residue at position 34). Suitable mammalian host cells are able to modify vitamin K-dependent polypeptide glutamate residues to γ-carboxyglutamate. Mammalian cells derived from kidney and liver are especially useful as host cells.

Nucleic Acids Encoding Modified Vitamin K-Dependent Polypeptides

Isolated nucleic acid molecules encoding modified vitamin K-dependent polypeptides of the invention can be produced by standard techniques. As used herein, "isolated" refers to a sequence corresponding to part or all of a gene encoding a modified vitamin K-dependent polypeptide, but free of sequences that normally flank one or both sides of the wild-type gene in a mammalian genome. An isolated polynucleotide can be, for example, a recombinant DNA molecule, provided one of the nucleic acid sequences normally found immediately flanking that recombinant DNA molecule in a naturally-occurring genome is removed or absent. Thus, isolated polynucleotides include, without limitation, a DNA that exists as a separate molecule (e.g., a cDNA or genomic DNA fragment produced by PCR or restriction endonuclease treatment) independent of other sequences as well as recombinant DNA that is incorporated into a vector, an autonomously replicating plasmid, a virus (e.g., a retrovirus, adenovirus, or herpes virus), or into the genomic DNA of a prokaryote or eukaryote. In addition, an isolated polynucleotide can include a recombinant DNA molecule that is part of a hybrid or fusion polynucleotide.

It will be apparent to those of skill in the art that a polynucleotide existing among hundreds to millions of other polynucleotides within, for example, cDNA or genomic libraries, or gel slices containing a genomic DNA restriction digest, is not to be considered an isolated polynucleotide.

Isolated nucleic acid molecules are at least about 14 nucleotides in length. For example, the nucleic acid molecule can be about 14 to 20, 20-50, 50-100, or greater than 150 nucleotides in length. In some embodiments, the isolated nucleic acid molecules encode a full-length modified vitamin K-dependent polypeptide. Nucleic acid molecules can be DNA or RNA, linear or circular, and in sense or antisense orientation.

Specific point changes can be introduced into the nucleic acid sequence encoding wild-type vitamin K-dependent polypeptides by, for example, oligonucleotide-directed mutagenesis. In this method, a desired change is incorporated into an oligonucleotide, which then is hybridized to the wild-type nucleic acid. The oligonucleotide is extended with a DNA polymerase, creating a heteroduplex that contains a mismatch at the introduced point change, and a single-stranded nick at the 5' end, which is sealed by a DNA ligase. The mismatch is repaired upon transformation of *E. coli* or other appropriate organism, and the gene encoding the modified vitamin K-dependent polypeptide can be re-isolated from *E. coli* or other appropriate organism. Kits for introducing site-directed mutations can be purchased commercially. For example, Muta-Gene7 in-vitro mutagenesis kits can be purchased from Bio-Rad Laboratories, Inc. (Hercules, Calif.).

Polymerase chain reaction (PCR) techniques also can be used to introduce mutations. See, for example, Vallette et al., 1989, *Nucleic Acids Res.*, 17(2):723-733. PCR refers to a procedure or technique in which target nucleic acids are amplified. Sequence information from the ends of the region of interest or beyond typically is employed to design oligonucleotide primers that are identical in sequence to opposite strands of the template to be amplified, whereas for introduction of mutations, oligonucleotides that incorporate the desired change are used to amplify the nucleic acid sequence of interest. PCR can be used to amplify specific sequences from DNA as well as RNA, including sequences from total genomic DNA or total cellular RNA. Primers are typically 14 to 40 nucleotides in length, but can range from 10 nucleotides to hundreds of nucleotides in length. General PCR techniques are described, for example in *PCR Primer: A Laboratory Manual*, ed. by Dieffenbach and Dveksler, Cold Spring Harbor Laboratory Press, 1995.

Nucleic acids encoding modified vitamin K-dependent polypeptides also can be produced by chemical synthesis, either as a single nucleic acid molecule or as a series of oligonucleotides. For example, one or more pairs of long oligonucleotides (e.g., >100 nucleotides) can be synthesized that contain the desired sequence, with each pair containing a short segment of complementarity (e.g., about 15 nucleotides) such that a duplex is formed when the oligonucleotide pair is annealed. DNA polymerase is used to extend the oligonucleotides, resulting in a double-stranded nucleic acid molecule per oligonucleotide pair, which then can be ligated into a vector.

Production of Modified Vitamin K-Dependent Polypeptides

Modified vitamin K-dependent polypeptides of the invention can be produced by ligating a nucleic acid sequence encoding the polypeptide into a nucleic acid construct such as an expression vector, and transforming a bacterial or eukaryotic host cell with the expression vector. In general, nucleic acid constructs include a regulatory sequence operably linked to a nucleic acid sequence encoding a vitamin K-dependent polypeptide. Regulatory sequences do not typically encode a gene product, but instead affect the expression of the nucleic acid sequence. As used herein, "operably linked" refers to connection of the regulatory sequences to the nucleic acid sequence in such a way as to permit expression of the nucleic acid sequence. Regulatory elements can include, for example, promoter sequences, enhancer sequences, response elements, or inducible elements.

In bacterial systems, a strain of *E. coli* such as BL-21 can be used. Suitable *E. coli* vectors include, without limitation, the pGEX series of vectors that produce fusion proteins with glutathione S-transferase (GST). Transformed *E. coli* typically are grown exponentially then stimulated with isopropylthiogalactopyranoside (IPTG) prior to harvesting. In general, such fusion proteins are soluble and can be purified easily from lysed cells by adsorption to glutathione-agarose beads followed by elution in the presence of free glutathione. The pGEX vectors are designed to include thrombin or factor Xa protease cleavage sites such that the cloned target gene product can be released from the GST moiety.

In eukaryotic host cells, a number of viral-based expression systems can be utilized to express modified vitamin K-dependent polypeptides. A nucleic acid encoding vitamin K-dependent polypeptide can be cloned into, for example, a baculoviral vector such as pBlueBac (Invitrogen, Carlsbad, Calif.) and then used to co-transfect insect cells such as *Spodoptera frugiperda* (Sf9) cells with wild-type DNA from *Autographa californica* multiply enveloped nuclear polyhedrosis virus (AcMNPV). Recombinant viruses producing the modified vitamin K-dependent polypeptides can be identified by standard methodology. Alternatively, a nucleic acid encoding a vitamin K-dependent polypeptide can be introduced into a SV40, retroviral, or vaccinia based viral vector and used to infect suitable host cells.

Mammalian cell lines that stably express modified vitamin K-dependent polypeptides can be produced by using expression vectors with the appropriate control elements and a selectable marker. For example, the eukaryotic expression vector pCDNA.3.1+ (Invitrogen) is suitable for expression of modified vitamin K-dependent polypeptides in, for example, COS cells, HEK293 cells, or baby hamster kidney cells. Following introduction of the expression vector by electroporation, DEAE dextran-, calcium phosphate-, liposome-mediated transfection, or other suitable method, stable cell lines can be selected. Alternatively, transiently transfected cell lines are used to produce modified vitamin K-dependent polypeptides. Modified vitamin K-dependent polypeptides also can be transcribed and translated in vitro using wheat germ extract or rabbit reticulocyte lysate.

Modified vitamin K-dependent polypeptides can be purified from conditioned cell medium by applying the medium to an immunoaffinity column. For example, an antibody having specific binding affinity for Factor VII can be used to purify modified Factor VII. Alternatively, concanavalin A (Con A) chromatography and anion-exchange chromatography (e.g., DEAE) can be used in conjunction with affinity chromatography to purify factor VII. Calcium dependent or independent monoclonal antibodies that have specific binding affinity for factor VII can be used in the purification of Factor VII.

Modified vitamin K-dependent polypeptides such as modified protein C can be purified by anion-exchange chromatography, followed by immunoaffinity chromatography using an antibody having specific binding affinity for protein C.

Modified vitamin K-dependent polypeptides also can be chemically synthesized using standard techniques. See, Muir and Kent, 1993, *Curr. Opin. Biotechnol.*, 4(4):420-427, for a review of protein synthesis techniques.

Pharmaceutical Compositions

The invention also features a pharmaceutical composition including a pharmaceutically acceptable carrier and an amount of a vitamin K-dependent polypeptide effective to inhibit clot formation in a mammal. The vitamin K-dependent polypeptide includes a modified GLA domain with at least one amino acid substitution or insertion that enhances membrane-binding affinity of the polypeptide relative to a corresponding native vitamin K-dependent polypeptide. In some embodiments, activity of the vitamin K-dependent polypeptide also is enhanced. Useful modified vitamin K-dependent polypeptides of the pharmaceutical compositions can include, without limitation, protein C or APC, active site modified APC, active site modified factor VIIa, active site modified factor IXa, active site modified factor Xa, or Protein S, as discussed above. Pharmaceutical compositions also can include an anticoagulant agent such as aspirin, warfarin, or heparin.

The concentration of a vitamin K-dependent polypeptide effective to inhibit clot formation in a mammal may vary, depending on a number of factors, including the preferred dosage of the compound to be administered, the chemical characteristics of the compounds employed, the formulation of the compound excipients and the route of administration. The optimal dosage of a pharmaceutical composition to be administered may also depend on such variables as the overall health status of the particular patient and the relative biological efficacy of the compound selected. These pharmaceutical compositions may be used to regulate coagulation in vivo. For example, the compositions may be used generally for the treatment of thrombosis. Altering only a few amino acid residues of the polypeptide as described above, generally does not significantly affect the antigenicity of the mutant polypeptides.

Vitamin K-dependent polypeptides that include modified GLA domains may be formulated into pharmaceutical compositions by admixture with pharmaceutically acceptable non-toxic excipients or carriers. Such compounds and compositions may be prepared for parenteral administration, particularly in the form of liquid solutions or suspensions in aqueous physiological buffer solutions; for oral administration, particularly in the form of tablets or capsules; or for intranasal administration, particularly in the form of powders, nasal drops, or aerosols. Compositions for other routes of administration may be prepared as desired using standard methods.

Formulations for parenteral administration may contain as common excipients sterile water or saline, polyalkylene glycols such as polyethylene glycol, oils of vegetable origin, hydrogenated naphthalenes, and the like. In particular, biocompatible, biodegradable lactide polymer, lactide/glycolide copolymer, or polyoxethylene-polyoxypropylene copolymers are examples of excipients for controlling the release of a compound of the invention in vivo. Other suitable parenteral delivery systems include ethylene-vinyl acetate copolymer particles, osmotic pumps, implantable infusion systems, and liposomes. Formulations for inhalation administration may contain excipients such as lactose, if desired. Inhalation formulations may be aqueous solutions containing, for example, polyoxyethylene-9-lauryl ether, glycocholate and deoxycholate, or they may be oily solutions for administration in the form of nasal drops. If desired, the compounds can be formulated as gels to be applied intranasally. Formulations for parenteral administration may also include glycocholate for buccal administration.

In an alternative embodiment, the invention also features a pharmaceutical composition including a pharmaceutically acceptable carrier and an amount of a vitamin K-dependent polypeptide effective to increase clot formation in a mammal. The vitamin K-dependent polypeptide includes a modified GLA domain with at least one amino acid substitution that enhances membrane binding affinity of the polypeptide relative to a corresponding native vitamin K-dependent polypeptide. These pharmaceutical compositions may be useful for the treatment of clotting disorders such as hemophilia A, hemophilia B and liver disease.

In this embodiment, useful vitamin K-dependent polypeptides of the pharmaceutical compositions can include, without limitations, factor VII or the active form of factor VII, factor VIIa. The modified GLA domain of factor VII or factor VIIa may include substitutions at amino acid 11 and amino acid 33, for example, a glutamine residue at amino acid 11 and a glutamic acid residue at amino acid 33. The modified GLA domain can include a substitution at amino acid 34, e.g., a glutamic acid residue at amino acid 34. The pharmaceutical composition may further comprise soluble tissue factor. Factor VII is especially critical to blood coagulation because of its location at the initiation of the clotting cascade, and its ability to activate two proteins, factors IX and X. Direct activation of factor X by factor VIIa is important for possible treatment of the major forms of hemophilia, types A and B, since the steps involving factors IX and VIII are bypassed entirely. Administration of factor VII to patients has been found to be efficacious for treatment of some forms of hemophilia. Improvement of the membrane affinity of factor VII or VIIa by modification of the GLA domain provides the potential to make the polypeptide more responsive to many coagulation conditions, to lower the dosages of VII/VIIa needed, to extend the intervals at which factor VII/VIIa must be administered, and to provide additional qualitative changes that result in more effective treatment. Overall, improvement of the membrane contact site of factor VII may increase both its activation rate as well as improve the activity of factor VIIa on factor X or IX. These steps may have a multiplicative effect on overall blood clotting rates in vivo, resulting in a very potent factor VIIa for superior treatment of several blood clotting disorders.

Other useful vitamin K-dependent polypeptides for increasing clot formation include factor IX, factor IXa, factor X, and factor Xa.

In another aspect, methods for decreasing clot formation in a mammal are described. The method includes administering an amount of vitamin K-dependent polypeptide effective to decrease clot formation in the mammal. The vitamin K-dependent polypeptide includes a modified GLA domain that enhances membrane-binding affinity of the polypeptide relative to a corresponding native vitamin K-dependent polypeptide. In some embodiments, activity also is enhanced. The modified GLA domain includes at least one amino acid substitution. Modified protein C or APC, protein S, or active site modified factors VIIa, IXa, and Xa containing substitutions in the GLA domain may be used for this method. The method further can include administering an anticoagulant agent.

In another aspect, the invention also features methods for increasing clot formation in a mammal that includes administering an amount of vitamin K-dependent polypeptide effective to increase clot formation in the mammal. The vitamin K-dependent polypeptide includes a modified GLA domain that enhances membrane-binding affinity of the polypeptide relative to a corresponding native vitamin K-dependent polypeptide. The modified GLA domain includes at least one amino acid substitution. Modified factor VII or VIIa and modified factor IX or IXa may be used in this method.

The invention will be further described in the following examples, which do not limit the scope of the invention described in the claims.

EXAMPLES

Example 1

Factor VII with Enhanced Membrane Affinity and Activity

It has been found that the membrane binding affinity of human blood clotting factor VII can be increased by site-directed mutagenesis. The properties of a P11Q,K33E mutant (referred to herein as Factor VIIQ11E33 or mutant factor VII) have been characterized. Membrane affinity was increased over wild type protein by about 20-fold. Autoactivation by the mutant was increased by at least 100-fold over that of wild type factor VII. The activated form of VIIQ11E33 (referred to as VIIaQ11E33) displayed about 10-fold higher activity toward factor X. The coagulation activity of VIIaQ11E33 with soluble tissue factor in normal plasma was about 10-fold higher than that of wild type VIIa. Coagulation activity of the zymogen, VIIQ11E33, with normal tissue factor (supplied as a 1:100 dilution of thromboplastin-HS), was 20-fold higher than wild type Factor VII. The degree to which activity was enhanced was dependent on conditions, with VIIQ11E33 being especially active under conditions of low coagulation stimuli.

In general, protein concentrations were determined by the Bradford assay using bovine serum albumin as the standard. Bradford, 1976, *Analyt. Biochem.* 248-254. Molar concentrations were obtained from the molecular weights of 50,000 for factor VII and 55,000 for factor X. Unless indicated, all activity measurements were conducted in standard buffer (0.05 M Tris, pH 7.5, 100 mM NaCl).

Production of Mutant Factor VII: Mutant factor VII was generated from wild type factor VII cDNA (GenBank Accession number M13232, NID g182799). Petersen et al., 1990, *Biochemistry* 29:3451-3457. The P11Q mutation (change of amino acid 11 from a proline residue to a glutamine residue) and the K33E mutation (change of amino acid 33 from a lysine residue to a glutamic acid residue) were introduced into the wild type factor VII cDNA by a polymerase chain reaction strategy essentially as described by Vallette et al., 1989, *Nucleic Acids Res.* 17:723-733. During this process, a mutation-diagnostic XmaIII restriction enzyme site was eliminated. Four PCR primers were designed to prime synthesis of two mutant fragments of M13232, one from MluI to BglII, positions 221 to 301, and the other from BglII to SstII, positions 302 to 787. These primers were used under standard PCR cycling conditions (GENEAMP, Perkin Elmer) to prime fragment synthesis using 1 ng of the wild-type factor VII cDNA as template. The resulting fragments were gel purified and digested with MluI and BglII or BglII and SstII. The two purified fragments were then ligated into the factor VIII cDNA in the expression vector Zem219b from which the corresponding wild-type sequence had been removed as a MluI-SstII fragment. Petersen et al., 1990 supra. The mutated fragments were sequenced in their entirety to confirm the P11Q and K33E substitutions, as well as to eliminate the possibility of other PCR-induced sequence changes.

Transfection, Selection and Purification: Baby hamster kidney (BHK) cells were grown in Dulbecco's modified Eagles medium supplemented with 10% fetal calf serum and penicillin-streptomycin. Subconfluent cells were transfected with the factor VII expression plasmid using lipofectAMINE (Gibco BRL) according to the manufacturer's recommendations. Two days post-transfection, cells were trypsinized and diluted to selective medium containing 1 µM methotrexate (MTX). Stably transfected BHK cells were subsequently cultured in serum-free Dulbecco's modified Eagles medium supplemented with penicillin-streptomycin, 5 µg/mL vitamin $K_1$ and 1 µM MTX, and conditioned medium was collected. The conditioned medium was applied twice to an immunoaffinity column composed of a calcium-dependent monoclonal antibody (CaFVII22) coupled to Afi-Gel 10. Nakagaki et al., 1991, *Biochemistry*, 30:10819-10824. The final purified Factor VIIQ11E33 ran as a single band on SDS polyacrylamide gel electrophoresis, with no evidence of factor VIIa in the preparation The pure VII(P11Q,K33E) mutant showed 1400-2800 factor VII units/mg.

Activation of Factor VII: Activated Factor VIIaQ11E33 was formed by bovine factor Xa cleavage of VIIQ11E33 (1:100 weight ratio, incubation for 1 hour at 37° C.). Alternatively, Factor VIIaQ11E33 was obtained by autoactivation (37° C., 20 minutes) in a mixture containing 7 µM VIIQ11E33, 0.7 µM sTF and phospholipid (phosphatidylserine/phosphatidylcholine (PS/PC), 25/75, 0.1 g/g protein).

Wild-type factor VIIa was a homogeneous, recombinant protein (NOVO Nordisk). Two preparations consisted of a commercial, lyophilized product and non-lyophilized product. The latter protein was further purified on FPLC mono-Q and showed a specific activity of 80,000 units/mg, calibrated with a George King NPP standard.

Enhanced membrane interaction by Factor VIIQ11E33: Phospholipid preparation, assay, and measurement of protein-membrane binding were conducted by the methods described by Nelsestuen and Lim, 1977, *Biochemistry*, 16:4164-4170. Large unilamellar vesicles (LUVs) and small unilamellar vesicles (SUVs) were prepared by methods described previously. See, Hope et al., *Biochem. Biophys. Acta.*, 812:55-65; and Huang, 1969, *Biochemistry*, 8:344-352. Highly pure phosphatidylserine (bovine brain) and egg phosphatidylcholine (Sigma Chemical Co.) were mixed in chloroform. The solvent was removed by a stream of nitrogen gas. The dried phospholipids were suspended in buffer. SUVs were formed by sonication and gel filtration while LUVs were formed by freeze-thaw and extrusion. Phospholipid concentrations were determined by organic phosphate assay assuming a phosphorous:phospholipid weight ratio of 25.

STVS of either PS/PC (25/75) or PS/PC (10/90) were prepared. Protein was added to phospholipid at the weight ratios shown in FIG. 1. Protein-membrane binding was assayed by light scattering at 90° by the method of Nelsestuen and Lim, 1977, supra. Briefly, the light scattering intensity of phospholipid vesicles alone ($I_1$) and after addition of protein ($I_2$) were measured and corrected for background from buffer and unbound protein. The molecular weight ratio of the protein-vesicle complex ($M_2$) to that of the vesicles alone (M1), can be estimated from the relationship in equation 1, where ∂n/∂c is the refractive index of the respective species.

$$I_2/I_1 = (M_2/M_1)^2 (\partial n/\partial c)^2 \quad \text{(eq. 1)}$$

If phospholipid and protein concentrations are known, the concentration of bound [P*PL] and free protein [P] can be estimated. These values, together with the maximum protein binding capacity [P*PL$_{max}$] of the vesicles (assumed to be 1.0 g/g for all proteins) can be used to obtain the equilibrium constant for protein-membrane interaction by the relationship in equation 2, where all concentrations are expressed as molar protein or protein binding sites.

$$K_D = [P][P*PL_{max} - P*PL]/[P*PL] \quad \text{(eq. 2)}$$

Binding was assessed at 5 mM calcium and is expressed as the ratio, M2/M1.

Figure 1B:
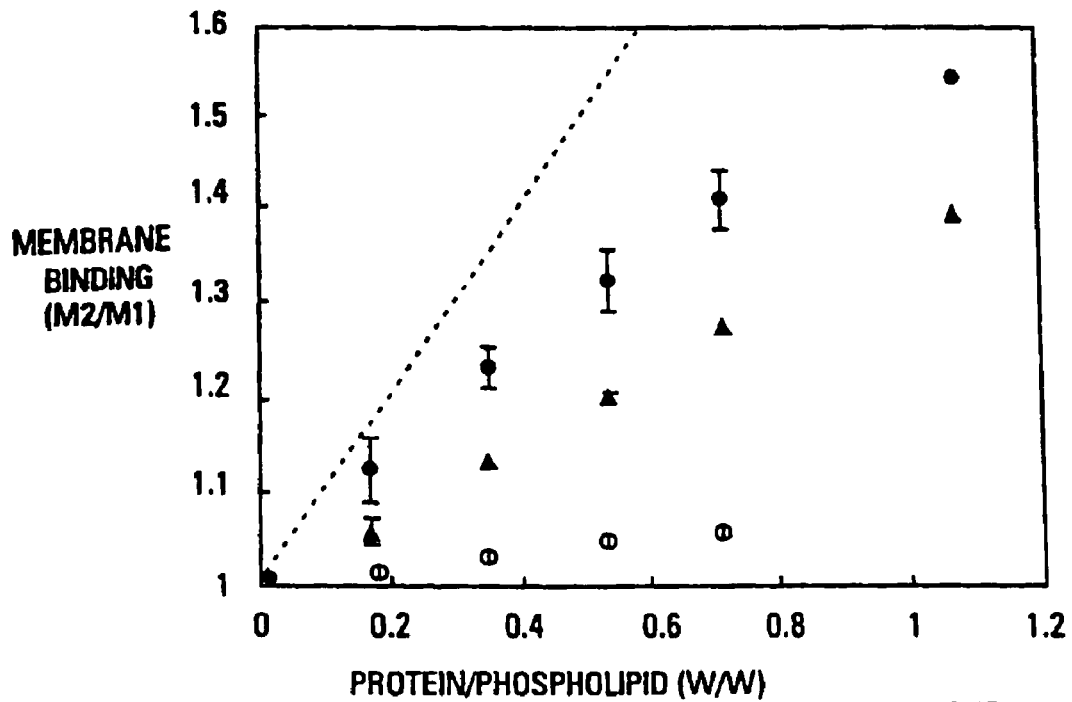

FIG. 1 shows the binding of wild type VIIa (open circles) and factor VIIQ11E33 (filled circles) to membranes of either PS/PC=25/75, 25 µg/ml (FIG. 1A) or PS/PC=10/90, 25 µg/ml (FIG. 1B). VIIQ11E33 had much higher affinity than wild type protein. Binding to PS/PC (25/75) was at the quantitative level so that [Protein$_{free}$] was essentially zero. Consequently, Kd values could not be estimated from this data. Membrane binding of bovine factor X (filled triangles) is shown in FIG. 1 as a reference. Bovine factor X is one of the highest affinity proteins in this family, giving a Kd for PS/PC (20/80) at 2 mM calcium of 40 nM. McDonald et al., 1997, *Biochemistry*, 36:5120-5127. The Kd for bovine factor X, obtained from the result at a protein/phospholipid ratio of 0.55 (FIG. 1), was 0.025 µM.

Binding of wild-type and mutant Factor VII to membranes of PS/PC (10/90) was also determined (FIG. 1B). The VIIQ11E33 bound at less than the quantitative level, which allowed a binding constant to be estimated from the relationship in equation 3.

$$Kd = [Protein_{free}][Binding\ sites_{free}]/[Protein_{bound}] \quad \text{(eq. 3)}$$

[Binding sites$_{free}$] were estimated from equation 4, assuming a maximum M2/M1 of 1.0 (i.e., [Binding sites$_{total}$]= [Phospholipid$_{weight\ conc}$/Protein$_{MW}$]). This is a common value observed for several proteins of this family. See McDonald et al., 1997, supra.

$$[Binding\ sites_{free}] = [Binding\ site_{total}] - [Protein_{bound}] \quad \text{(eq. 4)}$$

Using these assumptions and the data at a protein to phospholipid ratio of 0.37, Kd values were 0.7 µM for bovine factor X, 5.5 µM for wild type factor VII and 0.23 µM for VIIQ11E33. Thus, it was clear that factor VIIQ11E33 was greatly improved in membrane binding affinity over wild type factor VII and had one of the highest membrane-binding affinities among the vitamin K-dependent proteins.

It also has been observed that the difference between wild-type VIIa and VIIa-Q11E33 varied somewhat with the composition of the phospholipid vesicles that were used. For example, membranes containing PS/PE/PC (20/40/40) produced a 33-fold higher activity for VIIaQ11E33, while certain preparations of PS/PC (20/80 to 25/75) showed a 10 to 19 fold higher activity for VIIaQ11E33.

Enhanced activation of factor VIIQ11E33: The first step in coagulation involves the activation of factor VII. Autoactivation of VII was conducted in a solution containing 100 nM sTF (highly purified recombinant product from Dr. Walter Kisiel, Fiore et al., 1994, *J. Biol. Chem.*, 269:143-149), 36 nM VIIQ1 E33 and PS/PC (25/75, 22 µg/mL). Activity of VIIaQ11E33 was estimated at various time intervals by addition of 0.15 mm substrate S-2288 (Kabi) and assessing the rate of p-nitrophenylphosphate product release by absorbance change at 405 nm. Initial activity of the VIIQ11E33 preparation was less than 4% that of fully active VIIaQ11E33.

Figure 2:
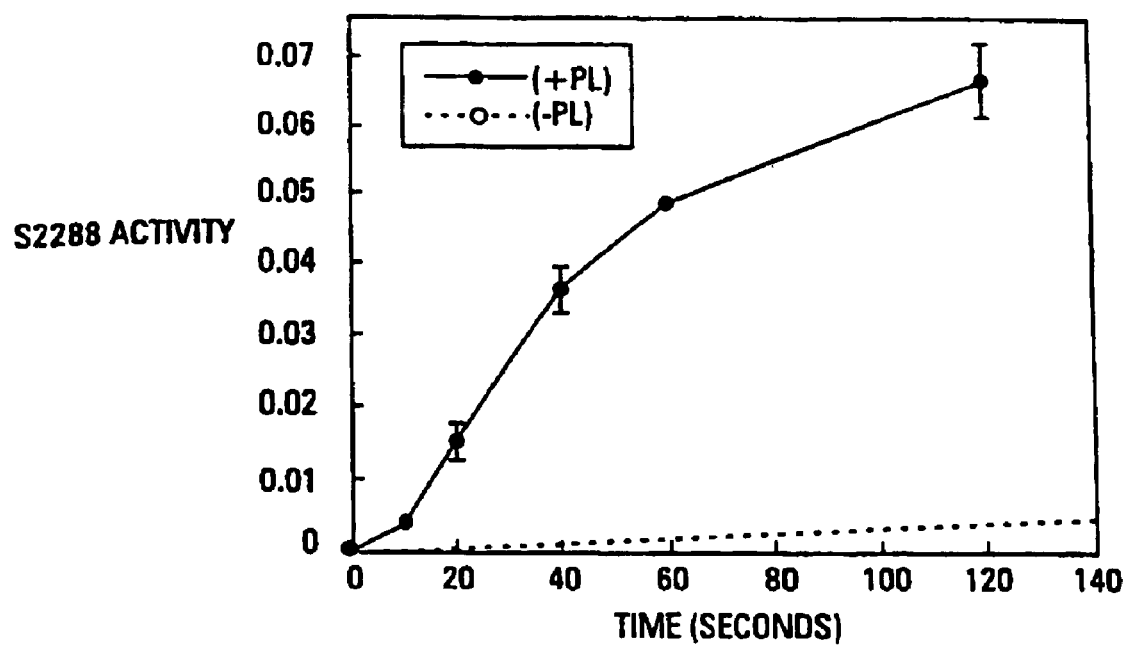
FIG. 2 depicts the autoactivation of VIIQ11E33. The dashed line shows activity in the absence of phospholipid.

VIIQ11E33 was found to be a much better substrate for activation than wild-type factor VII. FIG. 2 shows autoactivation of factor VIIQ11E33. The data were analyzed by the relationship in equation 5 (equation 7 of Fiore et al., 1994, supra).

$$\ln[VIIa]_t = \ln[VIIa]_0 + kcat*y*t \quad \text{(eq. 5)}$$

ln[VIIa]$_t$ is the factor VIIa concentration at time t, kcat is the catalytic rate constant for factor VIIa acting on VII and y is the fractional saturation of VIIa sites. For wild-type factor VIIa, this relationship and 1 µM sTF gave a kcat of 0.0045/s and a kcat/Km ratio of $7*10^3$ $M^{-1}s^{-1}$. See, Fiore et al., 1994, supra. For the VIIQ11E33 enzyme, autoactivation was rapid (FIG. 2) and it was only possible to estimate a lower limit for kcat. This was obtained from the VIIa doubling time of about 25 seconds (kcat=(ln2)/t$_{1/2}$). The resulting value (kcat$_{min}$= 0.03/s), along with the substrate concentration of this reaction ($3.6*10^{-8}$ M) and the assumption that y=1.0, gave a value for kcat/[S]=$8*10^5$ $M^{-1}s^{-1}$. This should be far below the true kcat/Km for VIIaQ11E33, but was about 100-times greater than the value of kcat/Km for wild type factor VIIa/sTF estimated by Fiore et al., 1994, supra. Thus, the combination of VIIaQ11E33 enzyme and Factor VIIQ11E33 substrate was superior to wild type proteins in the activation step of coagulation. This suggested that VIIQ11E33 was superior to wild type enzyme when coagulation conditions were minimal.

Enhanced activity of VIIaQ11E33: Once generated, factor VIIa activates either factor X or factor IX. Activation of bovine factor X (0.1 µM) by factor VIIa was carried out in 50 mM Tris-HCl buffer, pH 7.5 containing 100 mM NaCl, 5 mM calcium, various amounts of phospholipid (PS/PC, 25/75) and 1 mg/mL bovine serum albumin at 22.5° C. Factor VIIa (0.06 nM of VIIaQ11E33 or 0.6 nM wild type VIIa) was added at zero time and Xa activity at 1, 3 and 5 minute time points was determined. Aliquots of the reaction mixture (0.2 mL) were mixed with buffer (0.2 mL) containing 10 mM EDTA and 0.4 mM S-2222 (Kabi), a chromogenic substrate for factor Xa. Absorbance change at 405 nm was determined in a Beckman DU8 spectrophotometer. The amount of factor Xa generated was calculated from the extinction coefficient ($1*10^4 M^{-1}cm^{-1}$) of the p-nitrophenylphosphate reaction product and a velocity of 33/sec for substrate hydrolysis by purified bovine Xa under the conditions of this assay.

Figure 3:
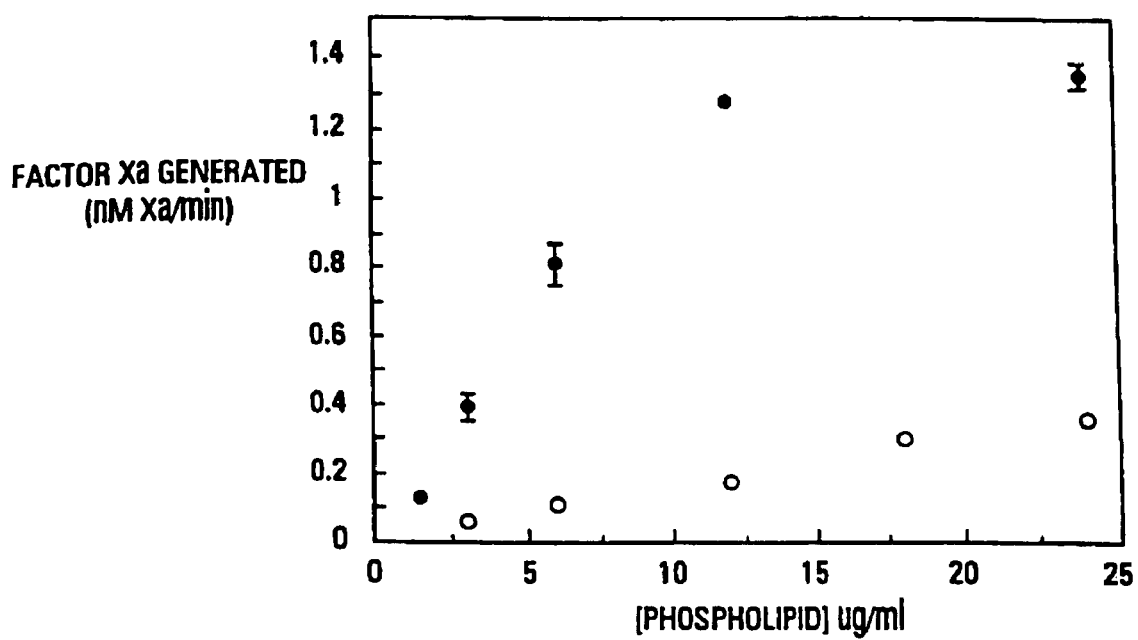
FIG. 3 depicts the activation of factor X by factor VIIa. Results for wild type factor VIIa (open circles) and VIIaQ11E33 (filled circles) are given for a concentration of 0.06 nM.

FIG. 3 compares the ability of wild type factor VIIa (open circles) and VIIaQ11E33 (closed circles) to activate factor X in a purified system. Again, VIIaQ11E33 was far superior to wild type factor VIIa in this reaction. The difference was greatest at low phospholipid concentrations and diminished to 2-fold at 200 µg phospholipid per mL. This was expected from the fact that high membrane concentrations cause a greater portion of wild type VIIa to bind to the membrane. Once again, the increased function of VIIaQ11E33 was greatest under conditions of low phospholipid exposure.

Superior coagulation of VIIaQ11E33: Blood clotting assays were conducted at 37° C. using the hand tilt method to detect clot formation. Human plasma (0.1 mL) was allowed to equilibrate at 37° C. for 1 minute. Various reagents were added in a volume of 0.1 mL of standard buffer. Soluble tissue factor (50 nM) and phospholipid (PS/PC, 10/90, 75 µg/mL) were added to the plasma, along with the factor VIIa concentration shown in FIG. 4 (0.1-32 nM). Finally, 0.1 mL of 25 mM CaCl$_2$ was added to start the reaction. Time to form a clot was measured. In most cases, the average and standard deviations of replicate samples was reported.

Figure 4:
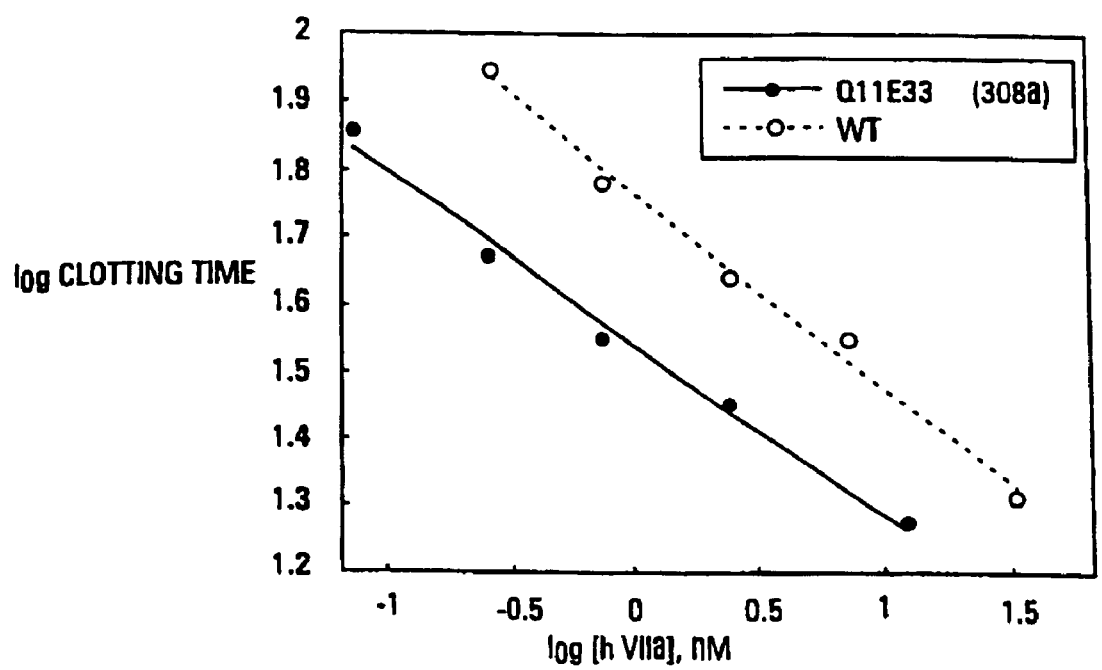
FIG. 4 depicts the coagulation of human plasma by VIIa and VIIaQ11E33 with soluble tissue factor.

FIG. 4 shows the coagulation times of wild type VIIa versus VIIaQ11E33 in normal human plasma. Coagulation was supported by sTF and added phospholipid vesicles. Endogenous wild type factor VII is approximately 10 nM in concentration, and had virtually no impact on coagulation times. The background coagulation was 120 seconds, with or without sTF. Factor VIIaQ11E33 showed approximately 8-fold higher activity than the wild type VIIa under these assay conditions. Similar results were obtained with factor VIII-deficient plasma, suggesting that the major pathway for blood clotting in this system involved direct activation of factor X by factor VIIa. Overall, factor VIIaQ11E33 was superior to wild type VIIa in procoagulant activity supported by membrane vesicles and soluble tissue factor. Wild type zymogen had virtually no activity under these conditions, as indicated by similar background clotting times of 2 minutes, whether or not sTF was added.

Procoagulant activity with normal tissue factor: Coagulation supported by normal tissue factor was assayed with standard rabbit brain thromboplastin-HS(HS=high sensitivity) containing calcium (Sigma Chemical Co.). This mixture contains both phospholipids and membrane-bound tissue factor. Rabbit brain thromboplastin-HS was diluted 1:100 in buffer and used in the assay of VII (added in the form of normal human plasma, which contains 10 nM factor VII) and VIIQ11E33 (added as the pure protein). The thromboplastin (0.2 mL) was added to plasma (0.1 mL) to start the reaction and the time required to form a blood clot was measured. Assays were also conducted with full strength thromboplastin, as described by the manufacturer.

At optimum levels of human thromboplastin, wild type VII showed a normal level of activity, about 1500 units per mg. This is approximately 25-fold less than the activity of wild type factor VIIa (80,000 units per mg). The VIIQ11E33 gave approximately 1500-3000 units per mg under the standard assay conditions, only 2-fold greater than wild type VII.

Figure 5:
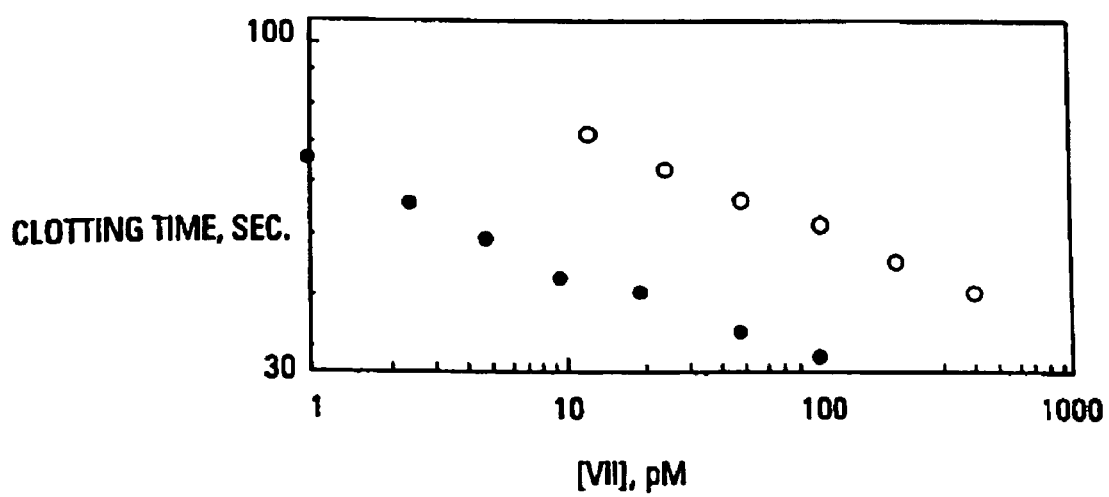
FIG. 5 depicts the coagulation of plasma by factor VII zymogens and normal tissue factor.

The difference between wild type VII and VIIQ11E33 was much greater when the coagulation conditions were suboptimal. FIG. 5 shows the clotting times and zymogen concentrations in assays that contained 0.01-times the normal thromboplastin level. Under these conditions, VIIQ11E33 was approximately 20-fold more active than wild type factor VII. Thus, greater efficacy of the VIIQ11E33 mutant was especially evident when coagulation conditions were limited, which is relevant to many situations in vivo.

Figure 6:
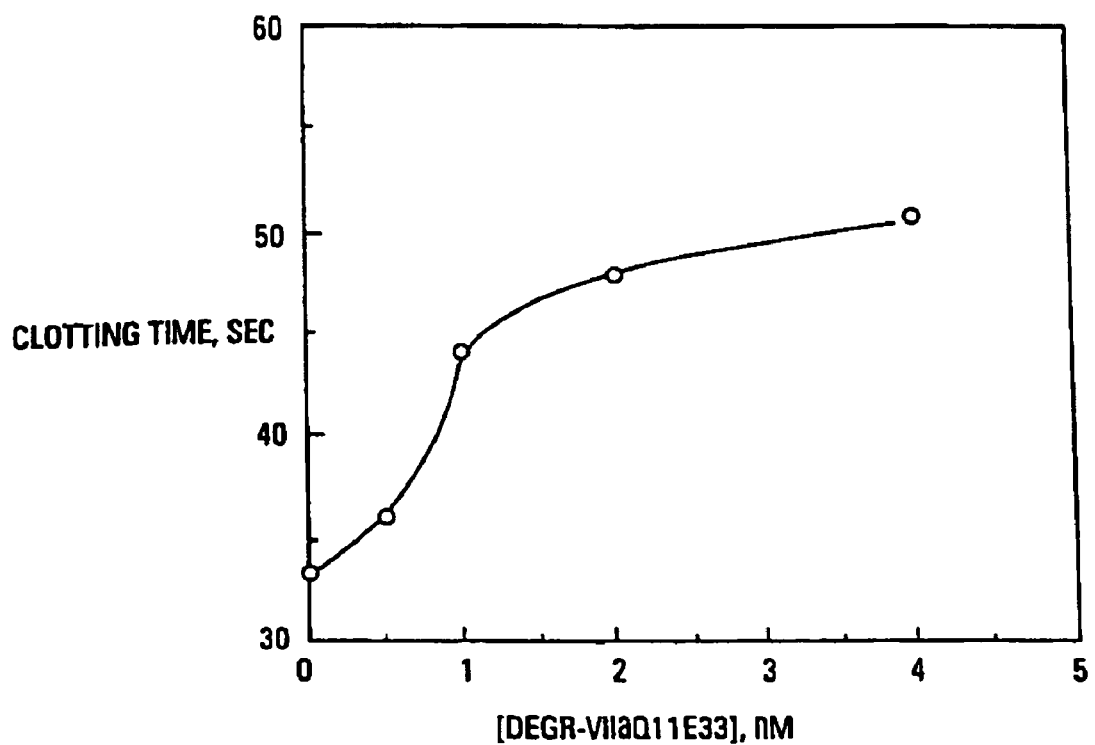
FIG. 6 depicts the inhibition of clot formation by active site modified factor VIIaQ11E33 (DEGR-VIIaQ11E33).

Anticoagulant Activities of DEGR-VIIaQ11E33: Standard coagulation assays were performed with normal human serum and human thromboplastin that was diluted 1:10 with buffer. The active site of factor VIIaQ11E33 was modified by DEGR as described by Sorenson, B. B. et al., 1997, supra. FIG. 6 shows the clotting time of DEGR-VIIaQ11E33 (0-4 nM) incubated with thromboplastin, in calcium buffer, for 15 seconds before addition of the plasma. The time to form a clot was determined with the hand tilt method. Clotting time was approximately 45 seconds with about 1 nM of DEGR-VIIaQ11E33. Active site modified Factor VIIaQ11E33 had enhanced anticoagulation activity.

Example 2

Purification of Factor VII

Factor VII (wild-type or mutant) was purified by Concanavalin A (Con A), DEAE, and affinity chromatography. Crude media of transfected 293 cells were incubated with Con A resin (Pharmacia) for four hours at 4° C. The resin then was washed with a solution containing 50 mM Tris, pH 7.5, 10 mM benzamidine, 1 mM $CaCl_2$, and 1 mM $MgCl_2$, and factor VII was eluted with 0.2 M D-methyl mannoside, 0.5 M NaCl in 50 mM Tris buffer, pH 7.5. Factor VII was dialyzed against 50 mM Tris, pH 8.0, 50 mM NaCl, 10 mM benzamidine, and 25 mM D-methyl mannoside overnight.

Dialyzed factor VII then was incubated with DEAE resin (Pharmacia) for one hour and the mixture was packed into a column. The DEAE column was washed with 50 mM Tris, pH 8.0, 10 mM Benzamidine, and 50 mM NaCl, and factor VII was eluted with a gradient from 50 mM to 500 mM NaCl in 50 mM Tris buffer, pH 8.0 at a flow rate of 2 mL/min. Fractions containing factor VII activity were pooled and dialyzed against 50 mM Tris, pH 8.0, 50 mM NaCl, and 5 mM $CaCl_2$ overnight. The Con A and DEAE partially purified factor VII was activated by bovine factor Xa (weight ratio 1:10, Enzyme Research Laboratory) at 37° C. for one hour.

Activated factor VII was purified further by affinity chromatography. A calcium-independent monoclonal antibody for factor VII (Sigma) was coupled to affigel-10 (Bio-Rad Laboratory) as described by Broze et al., *J. Clin. Invest.*, 1985, 76:937-946, and was incubated with the affinity column overnight at 4° C. The column was washed with 50 mM Tris, pH 7.5, 0.1 M NaCl, and factor VIIa was eluted with 50 mM Tris, pH 7.5, 3 M NaSCN at a flow rate of 0.2 mL/min. The eluted fractions were immediately diluted five fold into 50 mM Tris, pH 7.5, 0.1 M NaCl. Fractions containing factor VIIa activity were pooled, concentrated, and dialyzed against 50 mM Tris, pH 7.5, 0.1 M NaCl overnight.

The protein concentration of factor VIIa was determined with a Bio-Rad protein assay kit, using BSA as the standard. The purity of factor VIIa was assayed by Coomassie gel and Western Blotting under reduced and denatured conditions. Proteolytic activity of factor VIIa was measured using a synthetic peptide substrate spectrozyme-FVIIa (American Diagnostica) in the presence of thromboplastin (Sigma). Purified factor VIIa was stored in 0.1 mg/ml BSA, 0.1 M NaCl, 50 mM Tris, pH 7.5 at −80° C.

Procoagulant effectiveness of factor VIIa mutants was assessed using standard in vitro clotting assays (and modifications thereof); specifically, the prothrombin time (PT) assay and the activated partial thromboplastin (aPTT) assay. Various concentrations of Factor VIIa mutants were evaluated in pooled normal human donor plasma and in coagulation factor-deficient Factor VIII, Factor IX, Factor VII) human plasmas (Sigma). Clotting times were determined at 37° C. using both a FibroSystem fibrometer (BBL) with a 0.3 mL probe and a Sysmex CA-6000 Automated Coagulation Analyzer (Dade Behring).

Platelet poor plasma (PPP) was prepared from pooled normal human donor blood. Blood (4.5 mL) was drawn from each healthy donor into citrated (0.5 mLs of 3.2% buffered sodium citrate) Vacutainer tubes. Plasma was obtained after centrifugation at 2,000 g for ten minutes and was kept on ice prior to use. Purchased factor-deficient plasmas were reconstituted according to the manufacturer's instructions. Serial dilutions from each stock of Factor VIIa mutant were all prepared in plasma. All plasmas (with or without Factor VIIa mutants) were kept on ice prior to use. In all cases, the time to form a clot was measured. The average and standard deviation of replicate samples was reported.

The prothrombin time (PT) assay was performed in plasmas (with or without serial dilutions of added FVIIa mutants) using either of the following PT reagents: Thromboplastin C-Plus (Dade), Innovin (Dade), Thromboplastin With Calcium (Sigma), or Thromboplastin HS With Calcium (Sigma). Assays were conducted according to manufacturer's instructions. In addition to using PT reagents at the manufactured full-strength concentration, the PT assay also was performed using various dilutions of PT reagent. In all cases, the time to form a clot was measured. The average and standard deviation of replicate samples was reported.

The activated partial thromboplastin (aPTT) assay was performed in plasmas (with or without serial dilutions of added Factor VIIa mutants) using either Actin FS (Dade) or APTT reagent (Sigma). Clotting was initiated using 0.025M $CaCl_2$ (Dade) for Actin FS (Dade) or 0.02M $CaCl_2$ (Sigma) for APTT reagent (Sigma). Assays were conducted according to Manufacturer's instructions. In addition to using aPTT reagents at the manufactured full-strength concentration, the aPTT assay also was performed using various dilutions of aPTT reagent. In all cases, the time to form a clot was measured. The average and standard deviation of replicate samples was reported.

Clotting assays also were conducted at 37° C. in which different concentrations of phospholipid vesicles [at varying ratios of PS/PC or PS/PC/PE (PE=phosphatidylethanolamine)] were added to plasmas (with or without serial dilutions of added FVIIa mutants). Clotting was initiated by the addition of 20 mM $CaCl_2$. Various reagents were added in standard buffer. In all cases, the time to form a clot was measured. The average and standard deviation of replicate samples was reported.

Specific Factor VIIa clotting activity was assessed in plasmas (with or without added Factor VIIa mutants) using the STACLOT VIIa-rTF kit (Diagnostica Stago), as per the manufacturer's instructions. This kit is based on the quantitative clotting assay for activated FVII (Morrissey et al., 1993, *Blood*, 81(3):734-744). Clotting times were determined using both a FibroSystem fibrometer (BBL) with a 0.3 mL probe and a Sysmex CA-6000 Automated Coagulation Analyzer (Dade Behring).

Example 3

Circulatory Time of Factor VIIQ11E33 in the Rat

Figure 7:
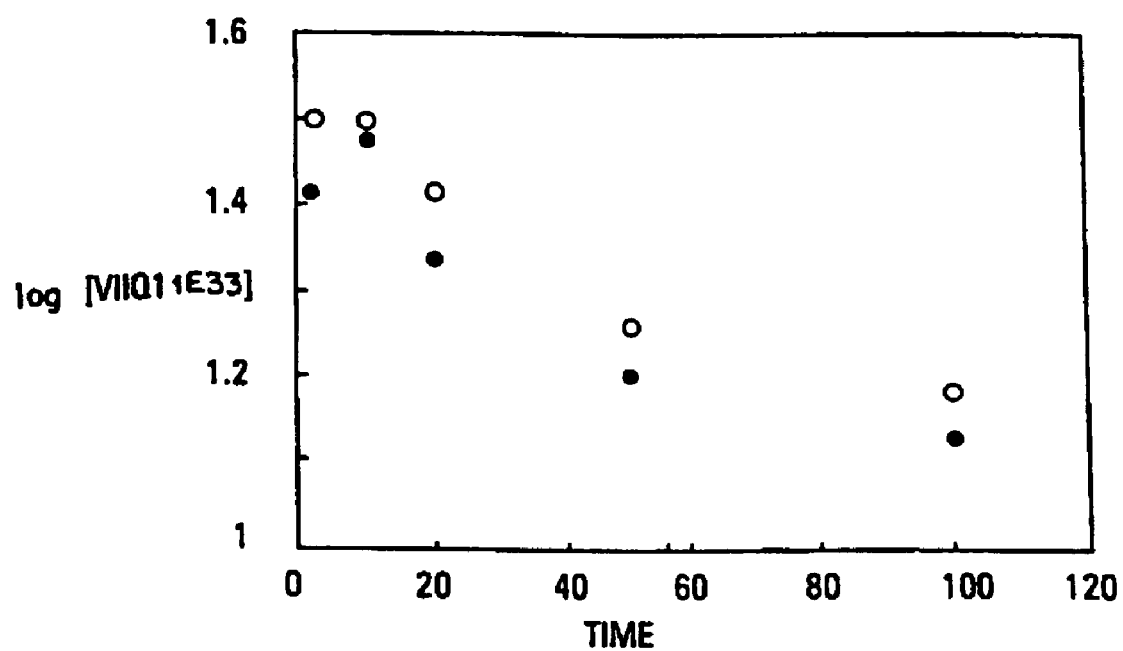
FIG. 7 depicts the circulatory time of factor VIIQ11E33 in rats.

Two anesthetized (sodium nembutol) Sprague Dawley rats (325-350 g) were injected with 36 µg of factor VIIQ11E33 at time zero. Injection was through the juggler vein, into which a cannula had been placed. At the times shown in FIG. 7, blood was withdrawn from the carotid artery, into which a cannula had been inserted by surgery. The amount of factor VIIQ11E33 in the circulation was estimated from the clotting time of human factor VII-deficient plasma, to which 1 µL of a 1:10 dilution of the rat plasma was added. A 1:100 dilution of rabbit brain thromboplastin-HS (Sigma Chemical Co.) was used. Coagulation was assessed by the manual tube tilt method as described in Example 1. The amount of factor VII activity in the plasma before injection of VIIQ11E33 was determined and was subtracted as a blank. The concentration of factor VIIQ11E33 in the circulation is given as log nM. A sham experiment in which a third animal received the operation and cannulation but no factor VIIQ11E33 was conducted. The amount of factor VIE activity in that animal did not change over the time of the experiment (100 minutes). At the end of the experiment, the animals were euthanized by excess sodium nembutol.

The rats appeared normal throughout the experiment with no evidence of coagulation. Therefore, the factor VIIQ11E33 did not cause indiscriminate coagulation, even in the post-operative rat. The circulation life-time of the VIIQ11E33 was normal (FIG. 7), with approximately 40% of the protein being cleared in about 60 minutes and an even slower disappearance of the remaining protein. This was similar to the rate of clearance of bovine prothrombin from the rat. Nelsestuen and Suttie, 1971, *Biochem. Biophys. Res. Commun.*, 45:198-203. This is superior to wild-type recombinant factor VIIa that gave a circulation half-time for functional assays of 2045 minutes. Thomsen et al., 1993, *Thromb. Haemost.*, 70:458-464. This indicated that factor VIIQ11E33 was not recognized as an abnormal protein and that it was not rapidly destroyed by coagulation activity. It appeared as a normal protein and should have a standard circulation lifetime in the animal.

Example 4

Enhancement of the membrane site and activity of protein C

Bovine and human protein C show a high degree of homology in the amino acids of their GLA domains (amino terminal 44 residues), despite about 10-fold higher membrane affinity of the human protein. Bovine protein C contains a proline at position 11 versus a histidine at position 11 of human protein C. The impact of replacing proline-11 in bovine protein C with histidine, and the reverse change in human protein C, was examined. In both cases, the protein containing proline-11 showed lower membrane affinity, about 10-fold for bovine protein C and 5-fold for human protein C. Activated human protein C (hAPC) containing proline at position 11 showed 2.4 to 3.5-fold lower activity than wild type hAPC, depending on the assay used. Bovine APC containing histidine-11 displayed up to 15-fold higher activity than wild type bAPC. This demonstrated the ability to improve both membrane contact and activity by mutation.

Mutagenesis of Protein C: A full-length human protein C cDNA clone was provided by Dr. Johan Stenflo (Dept. of Clinical Chemistry, University Hospital, Malmö, Sweden). The bovine protein C cDNA clone was provided by Dr. Donald Foster (ZymoGenetics, Inc., USA). The GenBank accession number for the nucleotide sequence of bovine protein C is KO2435, NID g163486 and is K02059, NID g190322 for the nucleotide sequence of human protein C.

Site-directed mutagenesis was performed by a PCR method. For human protein C mutagenesis of histidine-11 to proline, the following oligonucleotides were synthesized: A, 5'-AAA TTA ATA CGA CTC ACT ATA GGG AGA CCC AAG CTT-3' (corresponding to nucleotides 860-895 in the vector pRc/CMV, SEQ ID NO:7) to create a Hind III site between pRc/CMV and protein C. B, 5'-GCA CTC CCG CTC CAG GCT GCT <u>GGG</u> ACG GAG CTC CTC CAG GAA-3' (corresponding to the amino acid residues 4-17 in human protein C, the 8th residue in this sequence was mutated from that for human protein C to that of bovine protein C, as indicated by the underline, SEQ ID NO:8).

For bovine protein C mutagenesis of proline-11 to histidine, the following oligonucleotides were synthesized: A, (as described above); C, 5'-ACG CTC CAC GTT GCC <u>GTG</u> CCG CAG CTC CTC TAG GAA-3' (corresponding to amino acid residues 4-15 in bovine protein C, the 6th amino acid was mutated from that for bovine protein C to that of human protein C as marked with underline SEQ ID NO:9); D, 5'-TTC CTA GAG GAG CTG CGG <u>CAC</u> GGC AAC GTG GAG CGT-3' (corresponding to amino acid residues 4-15 in bovine protein C, the 7th amino acid was mutated from that for bovine protein C to that of human protein C; mutated nucleotides are underlined, SEQ ID NO:10); E, 5'-GCA TTT AGG TGA CAC TAT AGA ATA GGG CCC TCT AGA-3'

(corresponding to nucleotides 984-1019 in the vector pRc/CMV), creating a Xba I site between pRc/CMV and protein C, SEQ ID NO:11).

Both human and bovine protein C cDNAs were cloned into the Hind III and Xba I sites of the expression vector pRc/CMV. Human protein C cDNA containing the 5' terminus to amino acid-17 was PCR amplified with intact human protein C cDNA and primers A and B. The volume for the PCR reaction was 100 μl and contained 0.25 μg of template DNA, 200 μM each of the four deoxyribonucleoside triphosphates, 0.5 mM of each primer and 2.5 U of Pwo-DNA polymerase (Boehringer Mannheim) in Tris-HCl buffer (10 mM Tris, 25 mM KCl, 5 mM $(NH_4)_2SO_4$, and 2 mM $MgSO_4$, pH 8.85). Samples were subjected to 30 cycles of PCR consisting of a 2 minute, 94° C. denaturation period, a 2 minute, 55° C. annealing period, and a 2 minute, 72° C. elongation period. After amplification, the DNA was electrophoresed through an 0.8% agarose gel in 40 mM Tris-acetate buffer containing 1 mM EDTA. PCR products were purified with JET Plasmid Miniprep-Kit (Saveen Biotech AB, Sweden). Human protein C cDNA containing respective mutations was cleaved by Hind III and Bsr BI, and then cloned into pRc/CMV vector that was cleaved by Hind III/Xba I and that contained human protein C fragment from Bsr Br to the 3' terminus to produce a human protein C full length cDNA with the mutation.

Bovine protein C cDNA, containing the 5' terminus through amino acid-11, was PCR amplified with intact human protein C cDNA and primers A and C. Bovine protein C cDNA from amino acid 11 to the 3' terminus was amplified with intact human protein C cDNA and primers D and E. These two cDNA fragments were used as templates to amplify full length bovine protein C cDNA containing mutated amino acids with primers A and E. PCR reaction conditions were identical to those used for hAPC. The bovine protein C cDNA containing the respective mutations was cleaved by Hind III and Bsu 36I, and the Hind III/Bsu36I fragment was cloned into pRc/CMV vector containing intact bovine protein C fragments from the Bsu 36I to the 3' terminus to produce full-length bovine protein C cDNA containing the mutation. All mutations were confirmed by DNA sequencing prior to transfection.

Cell Culture and Expression: The adenovirus-transfected human kidney cell line 293 was grown in DMEM medium supplemented with 10% fetal calf serum, 2 mM L-glutamine, 100 U/ml of penicillin, 100 U/ml streptomycin and 10 μg/ml vitamin $K_1$. Transfection was performed using the lipofectin method. Feigner et al., 1987, *Proc. Natl. Acad. Sci. USA*, 84:7413-7417. Two μg of DNA was diluted to 0.1 mL with DMEM containing 2 mM of L-glutamine medium. Ten μL of Lipofectin (1 mg/ml) was added to 100 μL of DMEM containing 2 mM L-glutamine medium. DNA and lipofectin were mixed and left at room temperature for 10-15 min. Cell monolayers (25-50% confluence in 5-cm petri-dishes) were washed twice in DMEM with 2 mM L-glutamine medium. The DNA/lipid mixture was diluted to 1.8 mL in DMEM containing 2 mM L-glutamine medium, added to the cells and incubated for 16 hours. The cells were fed with 2 mL of complete medium containing 10% calf serum, left to recover for another 48-72 hours and then trypsinized and seeded into 10-cm dishes with selection medium (DMEM containing 10% serum and 400 μg/mL of Geneticin) at 1:5. See, Yan et al., 1990, *Bio/Technology* 655-661. Geneticin-resistant colonies were obtained after 3-5 weeks of selection. Twenty four colonies from each DNA transfection were picked, grown to confluence and the media screened for protein C expression with a dot-blot assay using monoclonal antibody HPC4 (for human protein C) and monoclonal antibody BPC5 (for bovine protein C). Clones producing high amounts of protein were isolated and grown until confluence in the presence of 10 μg/mL of vitamin $K_1$.

The purification of bovine recombinant protein C and its mutant were based on the method described previously with some modifications. Rezair and Esmon, 1992, *J. Biol. Chem.*, 267:26104-26109. Conditioned serum-free medium from stably transfected cells was centrifuged at 5000 rpm at 4° C. for 10 minutes. The supernatant was filtered through 0.45 μm of cellulose nitrate membranes (Micro Filtration Systems, Japan). EDTA (5 mM, final concentration) and PPACK (0.2 μM, final concentration) were added to the conditioned medium from 293 cells, then passed through a Pharmacia FFQ anion-exchange column at room temperature using Millipore Con Sep LC100 (Millipore, USA). The protein was eluted with a $CaCl_2$ gradient (starting solution, 20 mM Tris-HCl/150 mM NaCl, pH 7.4; limiting solution, 20 mM Tris-HC/150 mM NaCl/30 mM $CaCl_2$, pH 7.4). After removal of the $CaCl_2$ by dialysis and Chelex 100 treatment, the protein was reabsorbed to a second FFQ column, then eluted with an NaCl gradient (starting solution 20. mM Tris-HC/150 mM NaCl, pH 7.4; limiting solution, 20 mM Tris-HCl/500 mM NaCl, pH 7.4). At this point in the purification, wild-type and the mutant recombinant bovine protein C were homogeneous as determined by SDS-PAGE.

The first column used for purification of wild-type and mutant recombinant human protein C was the same as that described for bovine protein C. The chromatographic method described by Rezair and Esmon was employed with some modifications described for the method of protein S purification. Rezair and Esmon, 1992, supra; He et al., 1995, *Eur. J. Biochem.*, 227:433-440. Fractions containing protein C from anion-exchange chromatography were identified by dot-blot. Positive fractions were pooled and applied to an affinity column containing the $Ca^{2+}$-dependent antibody HPC4. The column was equilibrated with 20 mM Tris-HCl, 150 mM NaCl, pH 7.4, containing 5 mM Benzamidine-HCl and 2 mM $CaCl_2$. After application, the column was washed with the same buffer containing 1 M NaCl. Protein C was then eluted with 20 mM Tris-HCl, 150 mM NaCl and 5 mM EDTA, pH 7.4, containing 5 mM Benzamidine-HCl. After purification, the purity of all human and bovine recombinant protein C preparations was estimated by SDS-PAGE followed by silver staining. Proteins were concentrated using YM 10 filters (Amicon), then dialyzed against buffer (50 mM Tris-HCl and 150 mM NaCl, pH 7.4) for 12 hours and stored at −70° C. The concentrations of proteins were measured by absorbance at 280 nm.

Association of normal and mutant protein C molecules with membranes: LUVs and SUVs were prepared by methods described in Example 1. Light scattering at 90° to the incident light was used to quantitate protein-membrane binding as described above for Factor VII (25 μg/mL of PS/PC, (25/75) at 5 mM calcium (0.05 M Tris buffer-0.1 M NaCl, pH 7.5).

Figure 8A:
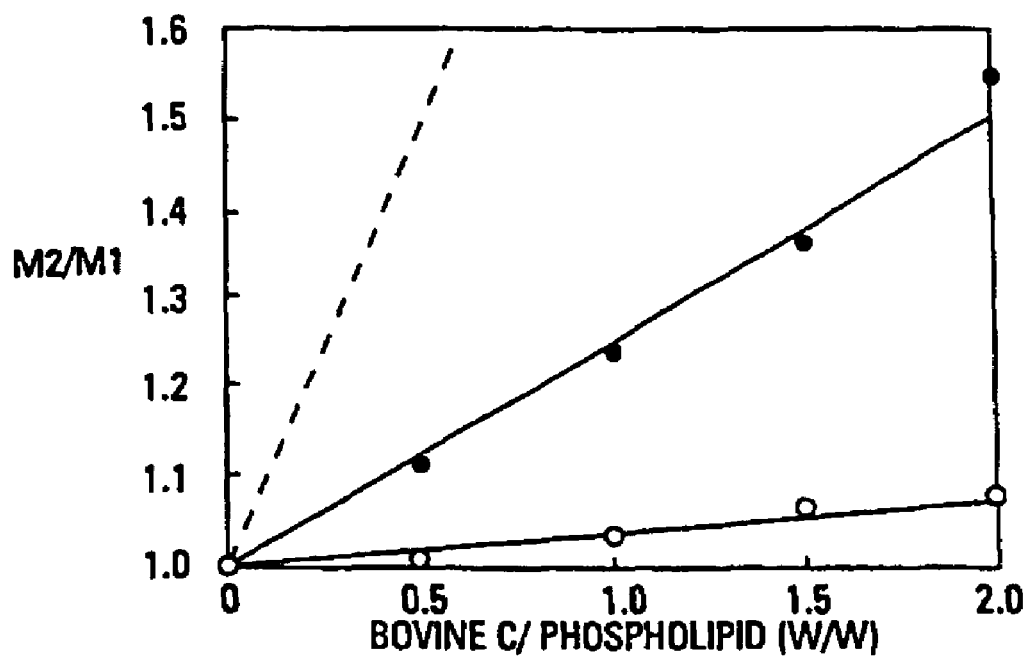
FIG. 8 depicts the membrane interaction by normal and modified proteins. Panel A shows the interaction of wild type bovine protein C (open circles) and bovine protein C-H11 (filled circles) with vesicles. Panel B shows the interaction of wild type human protein C (open circles) and human protein C-P11 (filled circles) with membranes. In both cases, the dashed line indicates the result if all of the added protein were bound to the membrane.

Bovine protein C containing histidine at position 11 interacted with membranes with about 10-fold higher affinity than wild type protein. When fit to equation 2, the data gave $K_D$ values of 930±80 nM for protein C-H11 and 9200±950 nM for wild type protein C FIG. 8A). The difference in affinity corresponded to about 1.4 kcal/mol at 25° C. In fact, membrane affinity of bovine protein C-H11 was almost identical to that of native human protein C (660 nM, FIG. 8B). This suggested that proline 11 formed a major basis for differences between the membrane binding site of human and bovine proteins.

Figure 8B:
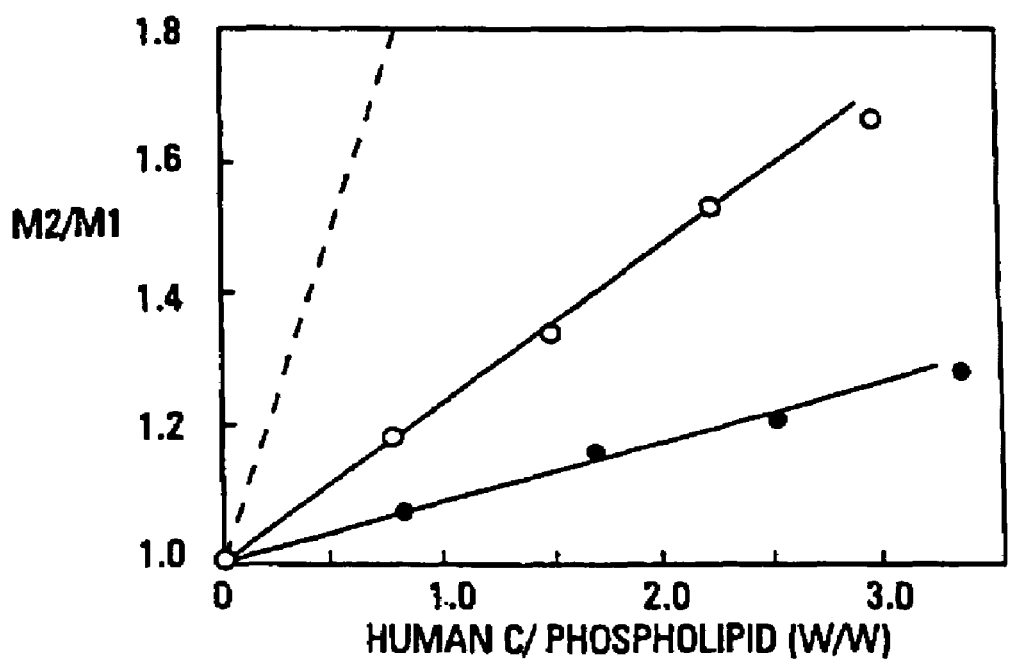

The reverse substitution, replacement of His-11 of human protein C by proline, decreased membrane affinity (FIG. 8B).

When fit to equation 2, these data gave $K_D$ values of 660±90 nM for wild type human protein C and 3350±110 nM for human protein C-P11. The impact of proline introduction was only slightly less than that of proline in the bovine proteins.

Impact of proline-11 on activity of activated protein C: Activated protein C was generated by thrombin cleavage, using identical conditions for both the wild type and mutant proteins. Approximately 150 μg of the various protein C preparations (1 mg/mL) were mixed with bovine thrombin (3 μg) and incubated at 37° C. for 5 hours. The reaction product was diluted to 0.025 M Tris buffer-0.05 M NaCl and applied to a one mL column of SP-Sephadex C-50. The column was washed with one mL of the same buffer and the flow-through was pooled as activated protein C. Approximately 65-80% of the protein applied to the column was recovered. APC activity was determined by proteolysis of S2366 (0.1 mM) at 25° C. The preparations were compared to standard preparations obtained on larger scale. Standard human APC was provided by Dr. Walter Kisiel. For bovine proteins, the standard was a large-scale preparation of thrombin-activated APC. The activity of bovine APC was consistent for all preparations of normal and mutant proteins (±5%). Two preparations of bovine APC were used for comparisons. Human APC generated from thrombin was 55 to 60% as active as the standard. The concentrations reported in this study were based on activity toward S2366, relative to that of the standard.

Standard APTT test used bovine or human plasma and standard APTT reagent (Sigma Chemical Co.) according to manufacturers instructions. Alternatively, phospholipid was provided in the form of vesicles formed from highly purified phospholipids. In this assay, bovine plasma (0.1 mL) was incubated with either kaolin (0.1 mL of 5 mg/mL in 0.05 M Tris buffer, 0.1 M NaCl, pH 7.5) or ellagic acid (0.1 mM in buffer) for 5 minutes at 35° C. Coagulation was started by adding 0.1 mL of buffer containing phospholipid and the amounts of APC shown, followed by 0.1 mL of 25 mM calcium chloride. All reagents were in standard buffer containing 0.05 M Tris buffer, 0.1 M NaCl, pH 7.5. An average of a 14-fold higher concentration of wild type bAPC was needed to duplicate the impact of the H11 mutant. Coagulation time at 10 nM bAPC-H11 was greater than 120 minutes. Standard APTT reagent (Sigma Chemical Co.) gave a clotting time of about 61 seconds at 35° C. with this plasma. Time required to form a clot was recorded by manual technique. The amount of phospholipid was designed to be the limiting component in the assay and to give the clotting times shown. The phospholipids used were SUVs (45 μg/0.4 mL in the final assay, PS/PC, 10/90) or LUVs (120 μg/0.4 mL in the final assay, PS/PC, 25/75).

Figure 9A:
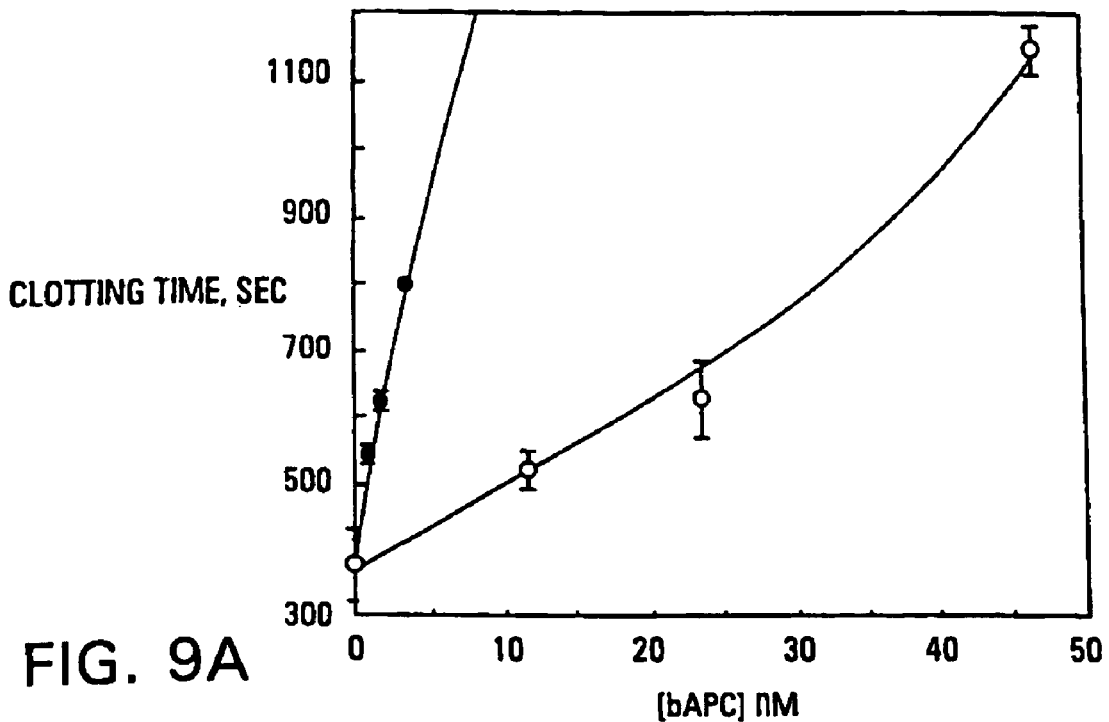
FIG. 9 depicts the influence of activated protein C on clotting times. In panel A, the average and standard deviation for three determinations of clotting times for bovine plasma are shown for wild type bovine APC (open circles) and for bAPC-H11 (filled circles). In panel B, the average and standard deviation of three replicates of human plasma coagulation for the wild type human (open circles) and human APC-P11 (filled circles) is shown.

The anticoagulant activity of activated protein C was tested in several assays. FIG. 9 shows the impact on the APTT assay, conducted with limiting phospholipid. Under the conditions of this assay, coagulation times decreased in a nearly linear, inverse relationship with phospholipid concentration. Approximately 14 times as much wild type bovine APC was needed to equal the effect of bovine APC-H11.

Parts of the study in FIG. 9 were repeated for membranes of PS/PC (25/75, LUV). Again, activity was limited by phospholipid, and its concentration was adjusted to give a control clotting time of 360 seconds (120 μg of 25% PS in the 0.4 mL assay). Approximately 15-fold more wild type enzyme was needed to equal the impact of the H11 mutant. Finally, standard APTT reagent (Sigma Chemical Co., standard clotting time 50±2 seconds) was used. Approximately 10.0±0.7 nM of wild type enzyme was needed to double the coagulation time to 102±5 seconds. The same impact was produced by 2.2±0.1 nM bovine APC-H11. Phospholipid was not rate limiting in the standard assay so a smaller impact on membrane affinity may be expected.

Figure 9B:
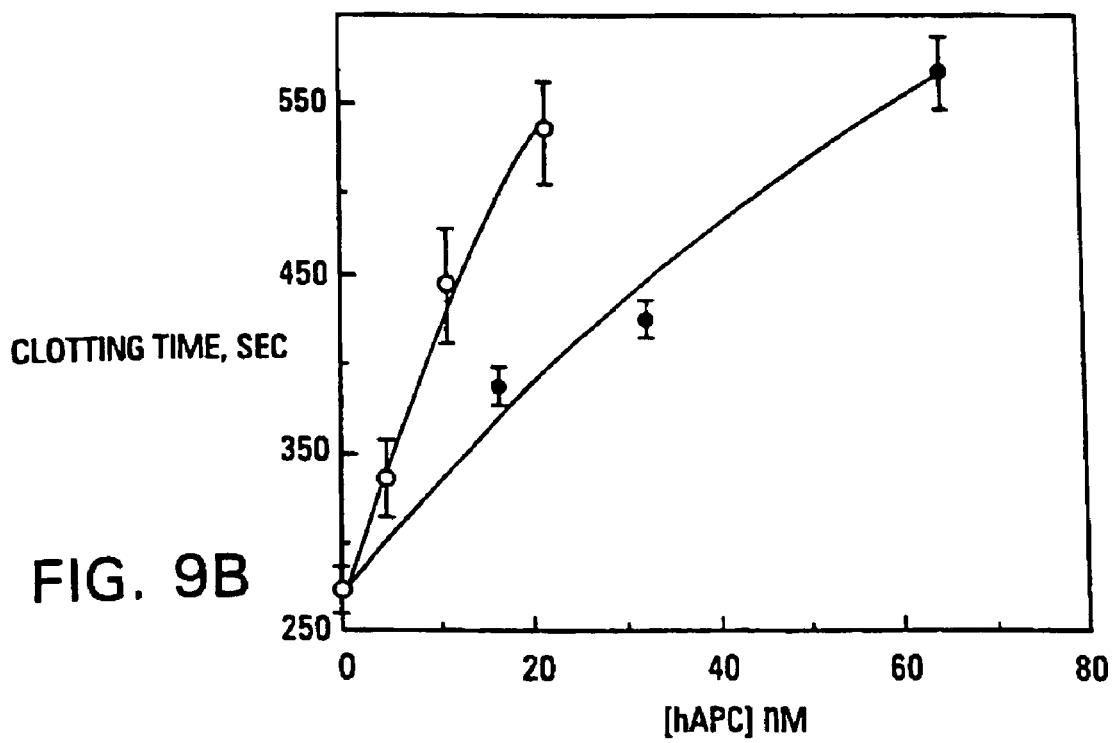

Results for human proteins are shown in FIG. 8B. About 2.5 times as much human APC containing proline-11 was required to prolong coagulation to the extent of wild type APC. A lower impact of proline-11 introduction may reflect the smaller differences in membrane affinity of the human proteins (FIG. 9B).

Inactivation of factor Va: Factor Va inactivation was assayed by the method of Nicolaes et al., 1996, *Thrombosis and Haemostasis*, 76:404-410. Briefly, for bovine proteins, bovine plasma was diluted 1000-fold by 0.05 M Tris, 0.1 M NaCl, 1 mg/mL bovine serum albumin and 5 mM calcium at pH 7.5. Phospholipid vesicles (5 μg/0.24 mL assay) and 5 μL of 190 nM thrombin were added to activate factor V. After a 10-minute incubation at 37° C., APC was added and the incubation was continued for 6 minutes. Bovine prothrombin (to 10 μM final concentration) and factor Xa (0.3 nM final concentration) were added and the reaction was incubated for one minute at 37° C. A 20 μL sample of this activation reaction was added to 0.38 mL of buffer (0.05 M Tris, 0.1 M NaCl, 5 mM EDTA, pH 7.5) containing S2288 substrate (60 μM). The amount of thrombin was determined by the change in absorbance at 405 nM ($\epsilon=1.0*10^4$ $M^{-1}s^{-1}$, $k_{cat}$ for thrombin=100/s). For human proteins, human protein S-deficient plasma (Biopool Canada, Inc.) was diluted 100-fold, factor Va was activated by human thrombin and the factor Va produced was assayed with the reagents used for the bovine proteins.

Figure 10A:
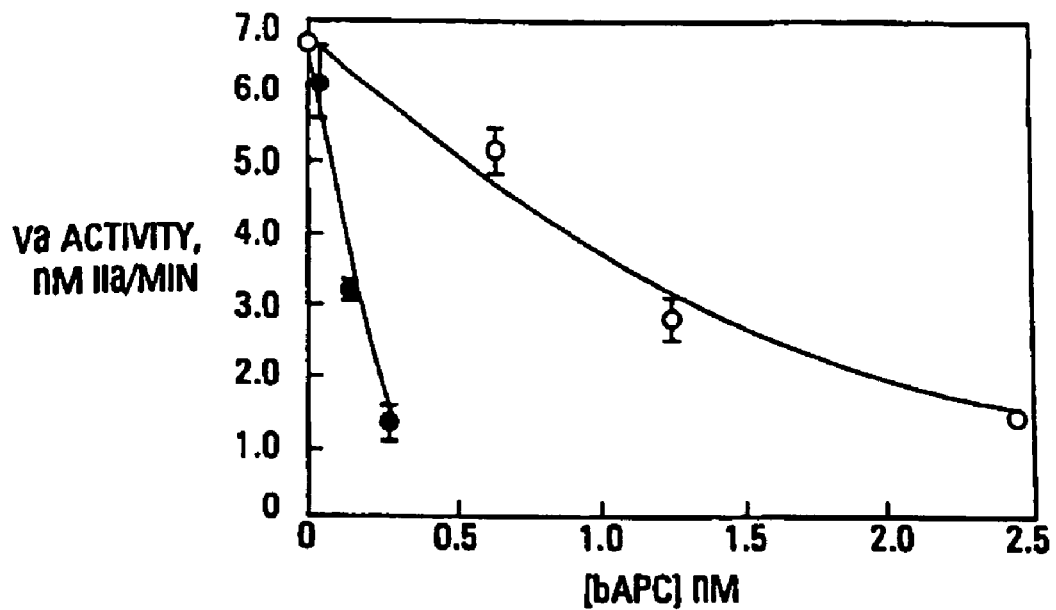
FIG. 10 depicts the inactivation of factor Va by bovine and human APC. Panel A depicts the inactivation of factor Va by wild type bovine APC (open circles) and bovine APC-H11 (filled circles). Panel B depicts the inactivation of human factor Va in protein S-deficient plasma by either wild type human APC (open circles) and human APC-H11 (filled circles).
Figure 10B:
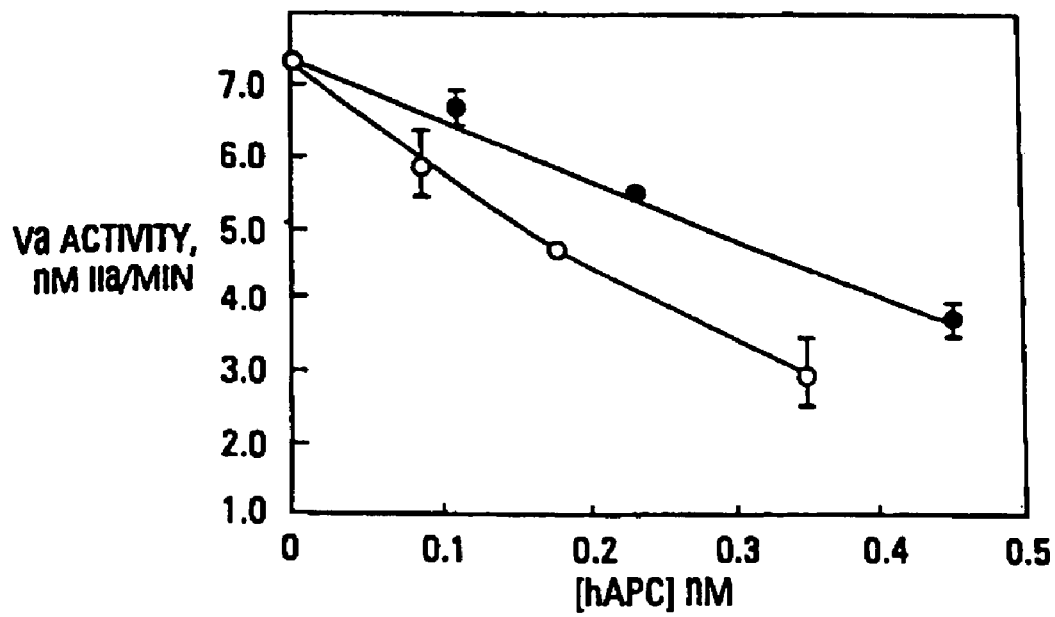

Bovine APC-H11 was 9.2-fold more active than wild type (FIG. 10A) in inactivating factor Va. As for membrane binding (above), the impact of proline-11 was less with the human proteins, with an average of 2.4-fold difference between the curves drawn for wild type and P-11 mutant (FIG. 10B). Similar results were obtained with normal human plasma.

Example 5

Identification of an Archetype Membrane Affinity for the Membrane Contact Site of Vitamin K-dependent Proteins Comparison of various human and bovine protein C mutants and other vitamin K-dependent polypeptides led to a proposed membrane contact site archetype. The electrostatic archetype consists of an electropositive core on one surface of the protein, created by bound calcium ions, surrounded by a halo of electronegative charge from amino acids of the protein. The closer a member of this protein family approaches this electrostatic pattern, the higher its affinity for membranes.

Phospholipid vesicles, wild type bovine protein C, protein-membrane interaction studies, activation and quantitation of protein C, and activity analysis were as described in Example 4.

Recombinant, mutant protein C was generated by the following procedures. Site-directed mutagenesis was performed by a PCR method. The following oligonucleotides were synthesized: A, as described in Example 4; F, 5'-GCA TTT AGG TGA CAC TAT AGA ATA GGG CCC TCT AGA-3' (corresponding to nucleotides 9841019 in the vector pRc/CMV, SEQ ID NO:11), creating a Xba I site between pRc/CMV and protein C; G, 5'-GAA GGC CAT TGT GTC TTC CGT GTC TTC GAA AAT CTC CCG AGC-3' (corresponding to amino acid residues 40-27 in bovine protein C, the 8th and 9th amino acids were mutated from QN to ED as marked with underline, SEQ ID NO:12); H, 5'-CAG TGT GTC ATC CAC ATC TTC GAA AAT TTC CTT GGC-3' (corresponding to amino acid residues 38-27 in human protein C, the 6th and 7th amino acids in this sequence were mutated from QN to ED as indicated with the underline, SEQ ID NO:13); I, 5'-GCC AAG GAA ATT TTC GAA GAT GTG GAT GAC ACA CTG-3' (corresponding to amino acid residues 27-38 in human protein C, the 6th and 7th amino acids in this sequence were mutated from QN to ED as indicated with underline, SEQ ID NO:14); J, 5'-CAG TGT GTC ATC CAC ATT TTC GAA AAT TTC CTT GGC-3 (corresponding to amino acid residues 38-27 in human protein C, the 7th amino acids in this sequence were mutated from Q to E as indicated with underline, SEQ ID NO:15); K, 5'-GCC AAG GAA ATT TTC GAA AAT GTG GAT GAC ACA CTG-3' (corresponding to amino acid residues 27-38 in human protein C, the 6th amino acid in this sequence was mutated from Q to E as indicated with underline, SEQ ID NO:16);

Both bovine and human protein C full length cDNAs were cloned into the Hind III and Xba I site of the vector pRc/CMV. To obtain bovine protein C mutant E33D34, PCR amplification of the target DNA was performed as follows. Bovine protein C cDNA containing the 5' terminus to the amino acid at position 40, was amplified with intact bovine protein C cDNA and primers A and C. The PCR reaction conditions were as described in Example 3. The sample was subjected to 30 cycles of PCR consisting of a 2 min denaturation period at 94° C., a 2 min annealing period at 55° C. and a 2 min elongation period at 72° C. After amplification, the DNA was electrophoresed through an 0.8% agarose gel in 40 mM Tris-acetate buffer containing 1 mM EDTA. The PCR products were purified with The Geneclean III kit (BIO 101, Inc. USA), and the PCR fragment of bovine protein C cDNA containing the respective mutations was cleaved by Hind III and Bbs I. The Hind III/Bbs I fragment and the human protein C fragment (Bbs I-3' terminus) were cloned into the Hind III and Xba I sites of pRc/CMV vector to produce a full-length bovine protein C cDNA with the mutations. Bovine protein C mutant H11 E33 D34 was created in the same way, but used bovine protein C mutant H11 as a template in the PCR reaction.

Human protein C cDNA containing the 5' terminus to amino acid-38 was PCR amplified with intact human protein C cDNA and primers A and D. Human protein C cDNA from amino acid 27 to the 3' terminus was amplified with intact human protein C cDNA and primers B and E. These two cDNA fragments were used as templates to amplify full length bovine protein C cDNA containing mutated amino acids (E33 D34) with primers A and B. Human protein C mutant E33 was obtained by the following steps: human protein C cDNA containing the 5' terminus to amino acid 38 was amplified with intact human protein C cDNA and primers A and F. Human protein C cDNA from amino acid 27 to the 3' terminus was amplified with intact human protein C cDNA and primers B and G. These two cDNA fragments were used as templates to amplify full length bovine protein C cDNA containing mutated amino acids (E33) with primers A and B. The PCR mixture and program were described above. The human protein C PCR products containing respective mutations were cleaved by Hind III and Sal I, and then the fragment (Hind III-Sal I) together with intact human protein C fragment (Sal I-3' terminus) were cloned into the Hind III and Xba I sites of pRc/CMV vector to produce the full length human protein C cDNA with the respective mutations. Human protein C containing a glycine residue at position 12, in conjunction with the E33D34 mutations also was made. All mutations were confirmed by DNA sequencing prior to transfection.

The adenovirus-transfected human kidney cell line 293 was cultured and transfected as described in Example 4. Bovine and human recombinant protein C and mutants were purified as described in Example 4.

The vitamin K-dependent proteins were classified into four groups on the basis of their affinities for a standard membrane (Table 5). Sequences of the amino terminal residues of some relevant proteins including human protein C (hC, SEQ ID NO:1), bovine protein C (bC, SEQ ID NO:2), bovine prothrombin (bPT, SEQ ID NO:17), bovine factor X (bX, SEQ ID NO:18), human factor VII (hVII, SEQ ID NO:3), human protein Z (hZ, SEQ ID NO:20), and bovine protein Z (bZ, SEQ ID NO:21) are given for reference, where X is Gla (γ-carboxyglutamic acid) or Glu.

bPT:
ANKGFLXXVRK$_{11}$GNLXRXCLXX$_{21}$PCSRXXAFXA$_{31}$LXSLSATDAF$_{41}$WAKY bX:
ANS-FLXXVKQ$_{11}$GNLXRXCLXX$_{21}$ACSLXXARXV$_{31}$FXDAXQTDXF$_{41}$WSKY hC:
ANS-FLXXLRH$_{11}$SSLXRXCIXX$_{21}$ICDFXXAKXI$_{31}$FQNVDDTLAF$_{41}$WSKH bC:
ANS-FLXXLRP$_{11}$GNVXRXCSXX$_{21}$VCXFXXARXI$_{31}$FQNTXDTMAF$_{41}$WSFY hVII:
ANA-FLXXLRP$_{11}$GSLXRXCKXX$_{21}$QCSFXXARXI$_{31}$FKDAXRTKLF$_{41}$WISY hZ:
AGSYLLXXLFX$_{11}$GNLXKXCYXX$_{21}$ICVYXXARXV$_{31}$FXNXVVTDXF$_{41}$WRRY bZ:
AGSYLLXXLFX$_{11}$GHLXKKCWXX$_{21}$ICVYXXARXV$_{31}$FXDDXTTDXF$_{41}$WRTY

TABLE 5

Charges and Affinity

| | Residue | | | | | | |
|---|---|---|---|---|---|---|---|
| | 11 | + | 29 | + 33 | + 34 | = Sum | Total | $K_D$ (nM) |
| Class I | | | | | | | | |
| bZ | −2 | + | −2 | −1 | −4 | −6 | 0.2$^a$ − 32 |
| hZ | −2 | + | −2 | | −3 | −5 | 2.0$^a$ − 170 |
| Class II | | | | | | | | |
| bPT-TNBS | | | −2 | | −2 | −1 | <10 |
| hVII-Q11E33 | | + | −2 | −1 | −2 | −2 | 10 |
| hS | | | −2 | −1 | −2 | −2 | 40 |
| Bx | | + | −2 | −1 | −2 | −3 | 40 |
| bC-E33D34 | P | + | −2 | −1 | −2 | −4 | 125 |
| hX | + | + | −2 | −1 | −1 | −2 | 160 |
| bPT | + | | −2 | | −1 | 0 | 100 |
| hPT | | | −2 | | −1 | −1 | — |
| bS | + | + | −2 | | 0 | 0 | 120 |
| Class III | | | | | | | | |
| bIX | | + | −2 | | −1 | −1 | 1000 |
| hIX | | + | −2 | | −1 | −1 | 1000 |
| hC | | + | | | +1 | −2 | 660 |
| bC-H11 | | + | | | +1 | −1 | 930 |

TABLE 5-continued

Charges and Affinity

| | Residue | | | | | | |
|---|---|---|---|---|---|---|---|
| | | 11 | + 29 | + 33 | + 34 = Sum | Total | $K_D$ (nM) |
| Class IV | | | | | | | |
| hC | | P | + | | | +1 | −2 | 3300 |
| hVII | | P | + | + | −1 | +1 | +1 | 4000 |
| bC | | P | + | | | +1 | −1 | 9200 |
| bVII | | P | + | + | | +1 | 0 | 15000 |

[a]Higher affinity value equals $k_{dissociation}/1 * 10^7 \, M^{-1}S^{-1}$; the denominator is a typical $k_{association}$ for other proteins.

In Table 5, vitamin K-dependent polypeptide mutants are in bold. The total charge (residues 1-34) includes 7 calcium ions (+14) and the amino terminus (+1).

Protein Z was assigned to class I on the basis of its dissociation rate constant, which was 100 to 1000 times slower than that of other proteins. If protein Z displayed a normal association rate constant (about $10^7 \, M^{-1}s^{-1}$) the $K_D$ would be about $10^{-10}$ M. Wei et al., 1982, *Biochemistry*, 21:1949-1959. The latter affinity may be the maximum possible for the vitamin K proteins. Protein Z is a candidate for anticoagulation therapy as a cofactor for inhibition of factor Xa by the protein Z-dependent protease inhibitor (ZPI). Incubation of protein Z and ZPI with factor Xa reduces the procoagulant activity of factor Xa. See, for example, Han et al., *Proc. Natl. Acad. Sci. USA*, 1998, 95:9250-9255. Enhancement of association kinetics would speed inhibition rates and increase binding affinity at equilibrium. Protein Z contains gly-2, which is thought to abolish interaction of asn-2 with bound calcium in other proteins. The presence of a glycine residue at position 2 may destabilize protein folding and lower association kinetics. In addition, the lower affinity of protein Z relative to that of bovine protein Z may arise from fewer anionic charges in positions 34-36 (Table 5).

Class IV proteins differed from class III in the presence of proline-11, which may alter affinity by non-electrostatic means.

Figure 11:
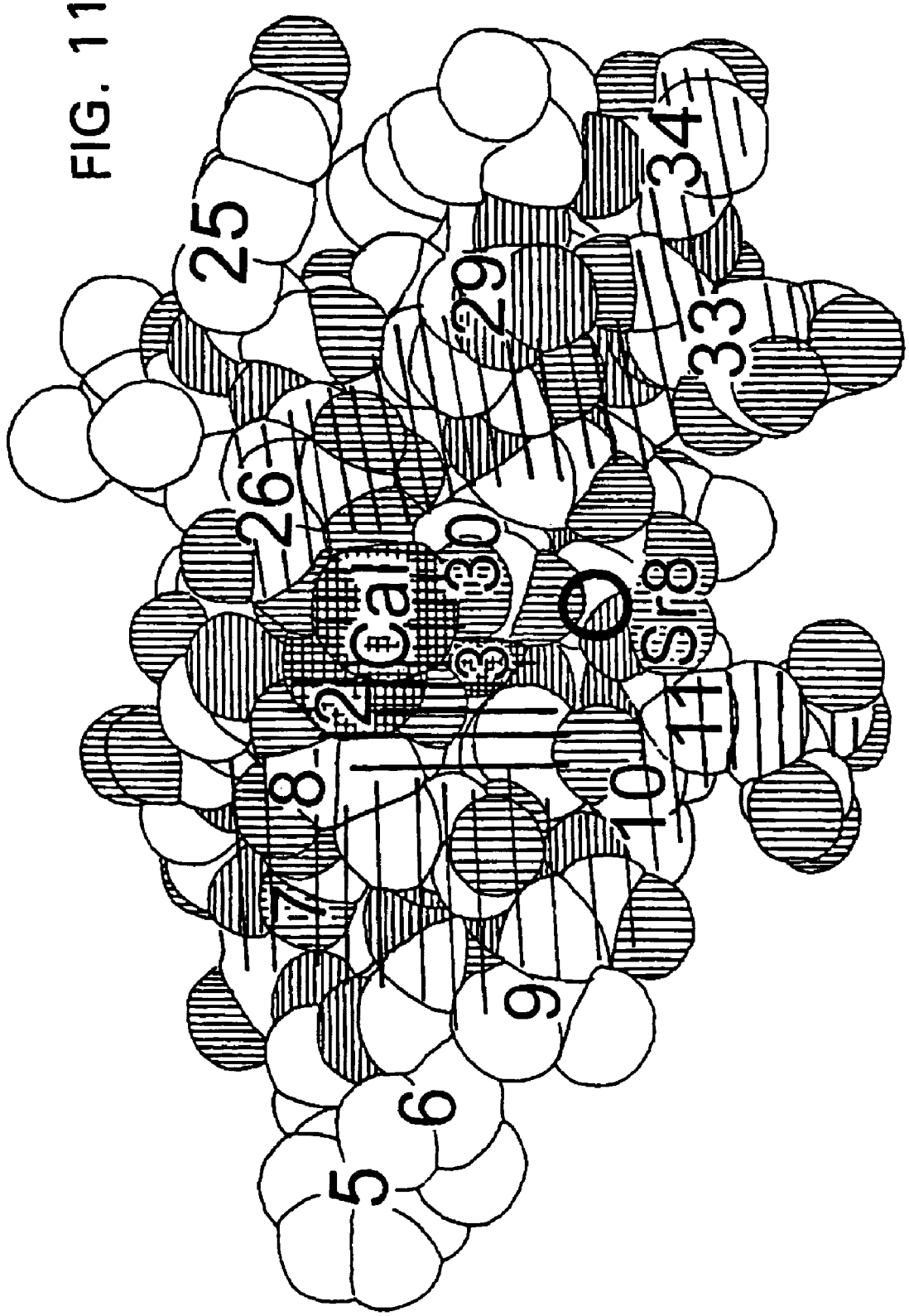
FIG. 11 depicts the electrostatic distribution of protein Z. Vertical lines denote electropositive regions and horizontal lines denote electronegative regions

While a relatively weak correlation existed between membrane affinity and net negative charge on residues 1-34, an excellent correlation was found when only residues 5, 11, 29, 33 and 34 were considered (Table 5). The latter amino acids are located on the surface of the protein. A number of proteins were modeled by amino acid substitution into the prothrombin structure and their electrostatic potentials were estimated by the program DelPhi. A sketch patterned after the electrostatic potential of bovine protein Z is shown in FIG. 11. Electronegative sites at 7, 8, 26, 30, 33, 34 and 11 produce a halo of electronegative charge surrounding a cationic core produced by the calcium-lined pore (FIG. 11). The closer a protein structure approaches this structure, the higher its affinity for the membrane. The highest affinity proteins show an electronegative charge extending to amino acids 35 and 36. This correlation is apparent from the wild-type proteins, the mutants and chemically modified proteins.

The pattern for other structures can be extrapolated from examination of the charge groups that are absent in other proteins. For example, Lys-11 and Arg-10 of bovine prothrombin generate high electropositive regions in their vicinity, the lack of Gla-33 in protein C and Factor VII create less electronegativity in those protein regions. In all cases, highest affinity corresponded to a structure with an electropositive core that was completely surrounded by electronegative protein surface, as shown for protein Z. The exceptions to this pattern are the proteins with Pro-11, which may lower affinity by a structural impact and ser-12 (human protein C), which is a unique uncharged residue.

Figure 12A:
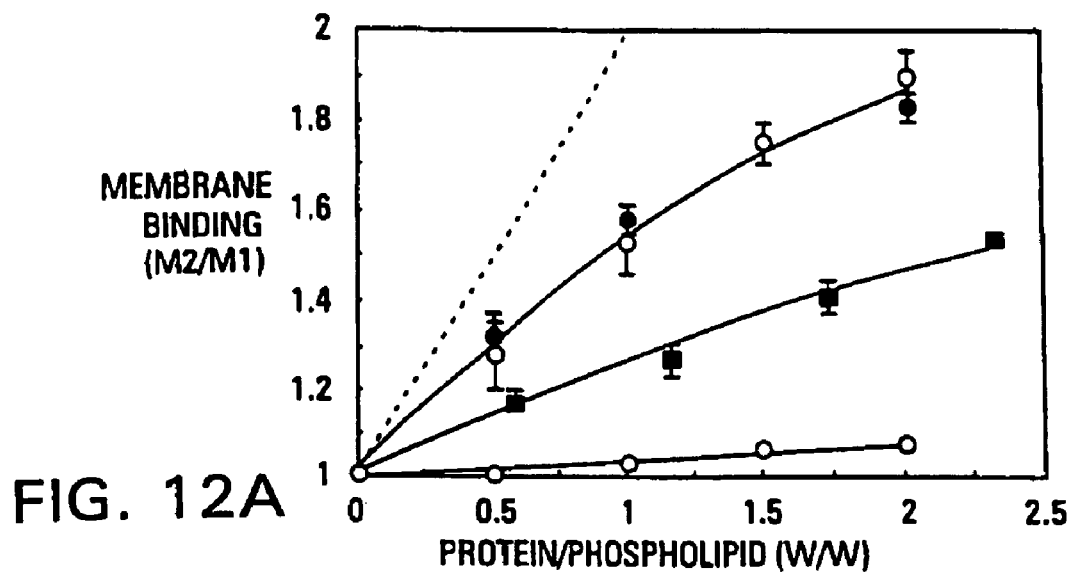
FIG. 12 depicts the membrane binding and activity of various protein Cs. Panel A shows membrane binding by wild type protein C (open circles), the P11H mutant of protein C (filled squares), Q33E, N34D mutant (filled circles) and bovine prothrombin (open squares). Panel B shows inhibition of blood coagulation by these mutants. Panel C shows the inactivation of factor Va.

To further test the hypothesis of an archetype for electrostatic distribution, site-directed mutagenesis was used to replace Gln33Asn34 of bovine and human protein C with Glu33Asp34. Glu33 should be further modified to Gla during protein processing. These changes altered the electrostatic potential of bovine protein C to that of bovine factor X. The membrane affinity of the mutant protein was expected to be lower than that of factor X due to the presence of proline-11. Indeed, the bovine protein C mutant gave a membrane affinity similar to that of bovine prothrombin (FIG. 12A), and slightly less than that of bovine factor X (Table 5).

Figure 12B:
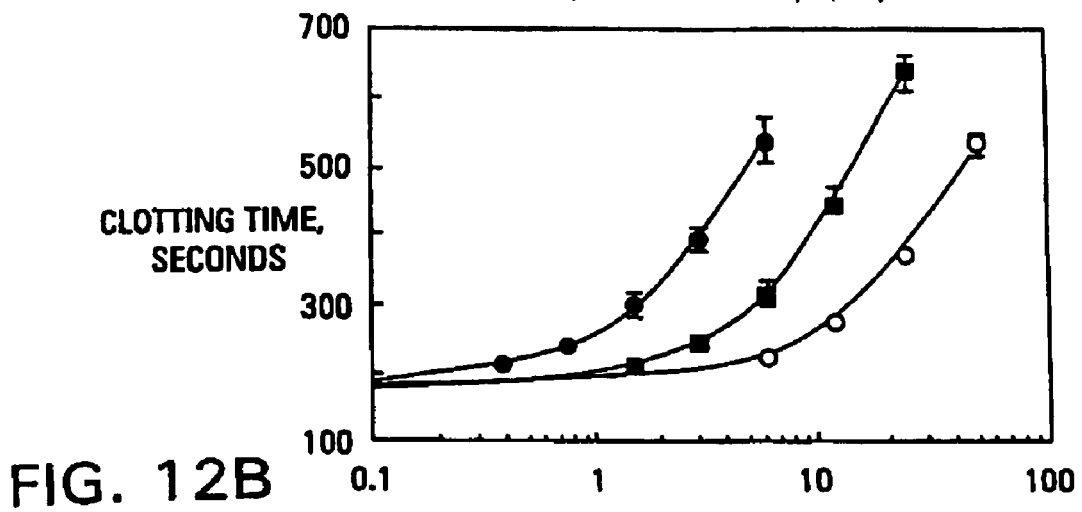
Figure 12C:
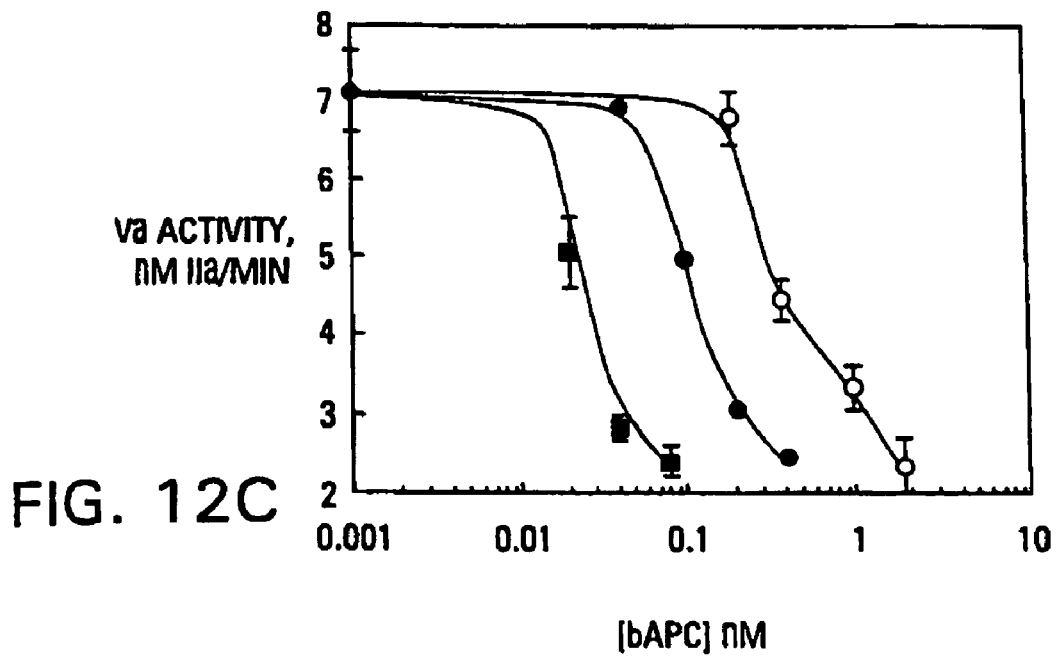

More interesting was that clot inhibition by APC was greater for the mutant than for the wild type enzyme (FIGS. 12B and 12C). Inclusion of results for the P11H mutant of bovine protein C from Example 3 showed that a family of proteins could be produced, each with different membrane affinity and activity, by varying the amino acid substitutions at positions 11, 33 and 34.

Figure 13A:
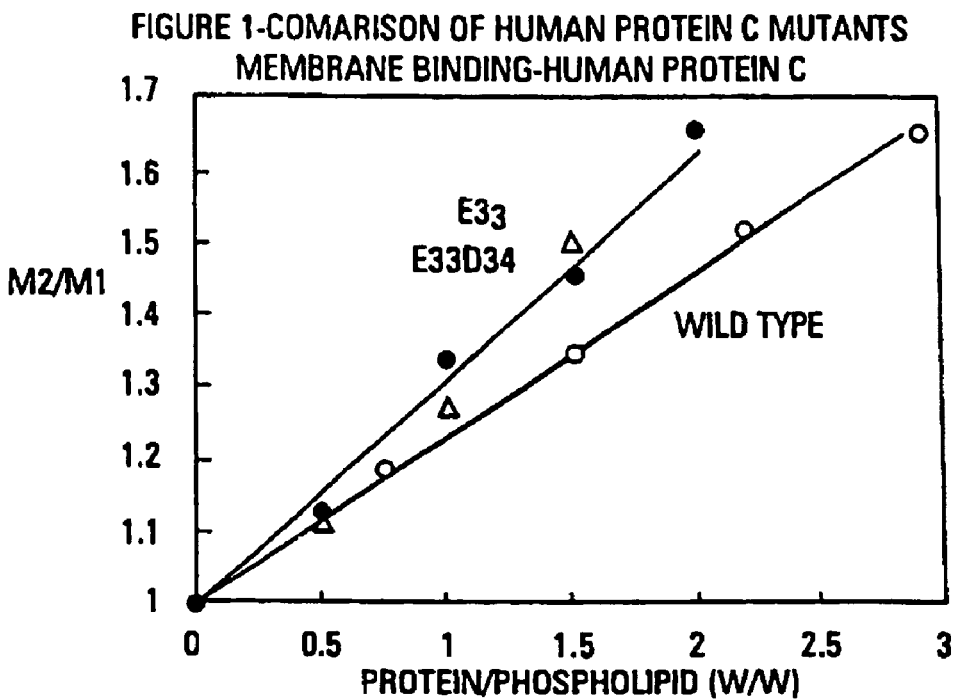
FIG. 13 compares membrane binding and activity of human protein C mutants. Panel A compares the membrane binding of wild-type (open circles), E33 (open triangles) and E33D34 (filled circles). Panel B compares the coagulation times using wild-type (open triangles), E33 (open circles) and E33D34 (filled circles).
Figure 13B:
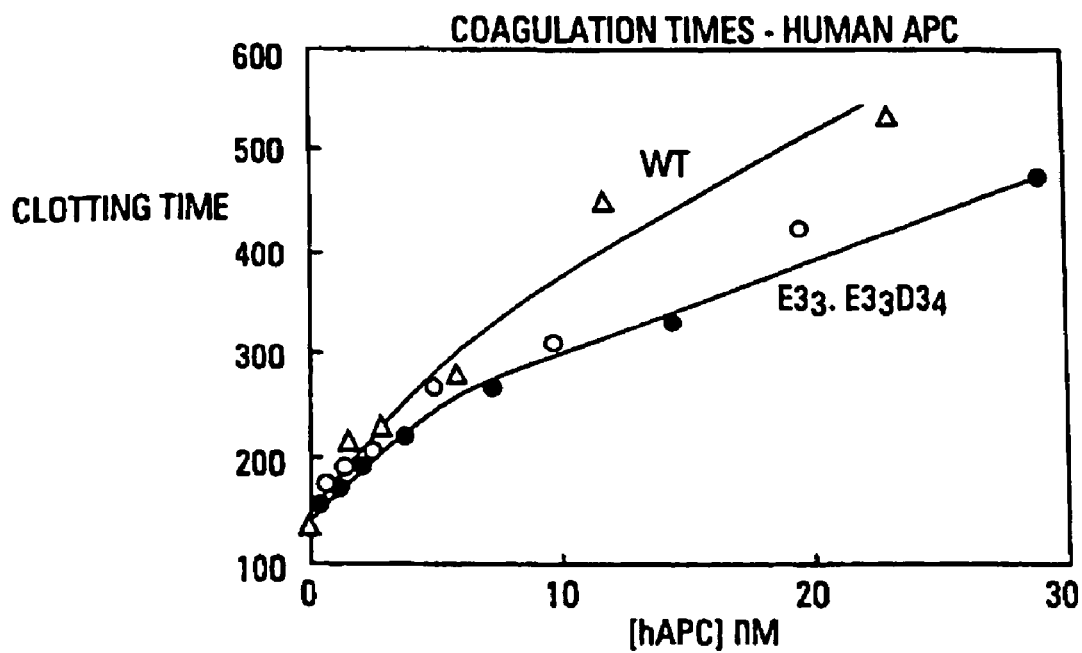

Human protein C mutants containing E33 and E33D34 resulted in a small increase in membrane binding affinity (FIG. 13a). Activity of these mutants was slightly less than the wild-type enzyme (FIG. 13b). Results with mutants of bovine protein C suggest that failure of the E33D34 mutation in the human protein may arise from H11 and/or other unique amino acids in the protein. FIG. 14A shows that the H11 mutant of bovine protein C bound to the membrane with about 10-fold higher affinity than wild type protein, the E33D34 mutant bound with about 70-times the affinity, but that the triple mutant, H11E33D34, was only slightly better than the H11 mutant. This relationship was mirrored in the activity of APC formed from these mutants (FIG. 14B). This result suggested that the presence of H11 reduced the impact of E33D34 on membrane binding affinity.

These results indicated that introduction of E33D34 alone may not be optimal for all proteins. Consequently, other mutations may be desirable to create human protein C that will use E33D34 and have maximum increased membrane affinity. The result with the bovine protein suggested that histidine 11 may be the primary cause of this phenomenon. Consequently, H11 may be altered to glutamine or to another amino acid in human protein C, along with the E33D34 mutation. Another amino acid that may impact the affinity is the serine at position 12, an amino acid that is entirely unique to human protein C. These additional changes should produce proteins with enhanced membrane affinity. Substitution of a glycine residue for serine at position 12 of human activated protein C, in conjunction with E33D34 resulted in 9-fold higher activity than wild-type activated human protein C. Activity of the G12E33D34 mutant was assessed with a dilute thromboplastin assay using a control clotting time of 30 seconds and normal human plasma. The electrostatic archetype also was tested by comparison of human and bovine factor X. The presence of lysine-11 in human factor X suggests that it should have lower affinity than bovine factor X. This prediction was borne out, by the result shown in FIG. 15.

Earlier studies had shown that trinitrobenzenesulfonic acid (TNBS) modification of bovine and human prothrombin fragment 1 had relatively little impact (0 to 5-fold) on membrane affinity. Weber et al., 1992, *J. Biol. Chem.*, 267:4564-4569; Welsch et al., 1988, *Biochemistry.* 27:4933-4938. Conditions used for the reaction resulted in derivatization of the amino terminus, a change that is linked to lowered membrane affinity. Welsch and Nelsestuen, 1988, *Biochemistry,* 27:4939-

4945. Protein modification in the presence of calcium, which protects the amino terminus, resulted in TNBS-modified protein with much higher affinity for the membrane than native fragment 1.

The suggestion that protein Z constitutes the archetype was based on its dissociation rate constant and that a normal association rate would generate a $K_D=10^{-10}$ M. Whether this value can be reached is uncertain. It is possible that the slow association rate of protein Z is caused by improper protein folding, resulting in a low concentration of the membrane-binding conformation. If conditions can be altered to improve protein folding, association rates of protein Z should improve. Indeed, the association rate constant for protein Z was improved by alteration of pH. The basis for this observation may be related to an unusual feature of the prothrombin structure, which is the close placement of the amino terminus (+1 at pH 7.5) to calcium ions 2 and 3. The +1 charge on the amino terminus is responsible for the slight electropositive region just above Ca-1 in FIG. 11. Charge repulsion between Ca and the amino terminal may destabilize protein folding and could be a serious problem for a protein that had low folding stability.

Table 6 provides additional support for the archetype model. It shows the relationship between distance of ionic groups from strontium ions 1 and 8 (corresponding to calcium 1 and an extra divalent metal ion found in the Sr x-ray crystal structure of prothrombin). The pattern suggests that the closer an ionic group is to these metal ions, the higher its impact on membrane affinity. The exception is Arg-16, which contributes to the charge of the electropositive core. Higher affinity is correlated with electronegative charge at all other sites. This correlation also applies to the GLA residues.

Figure 15:
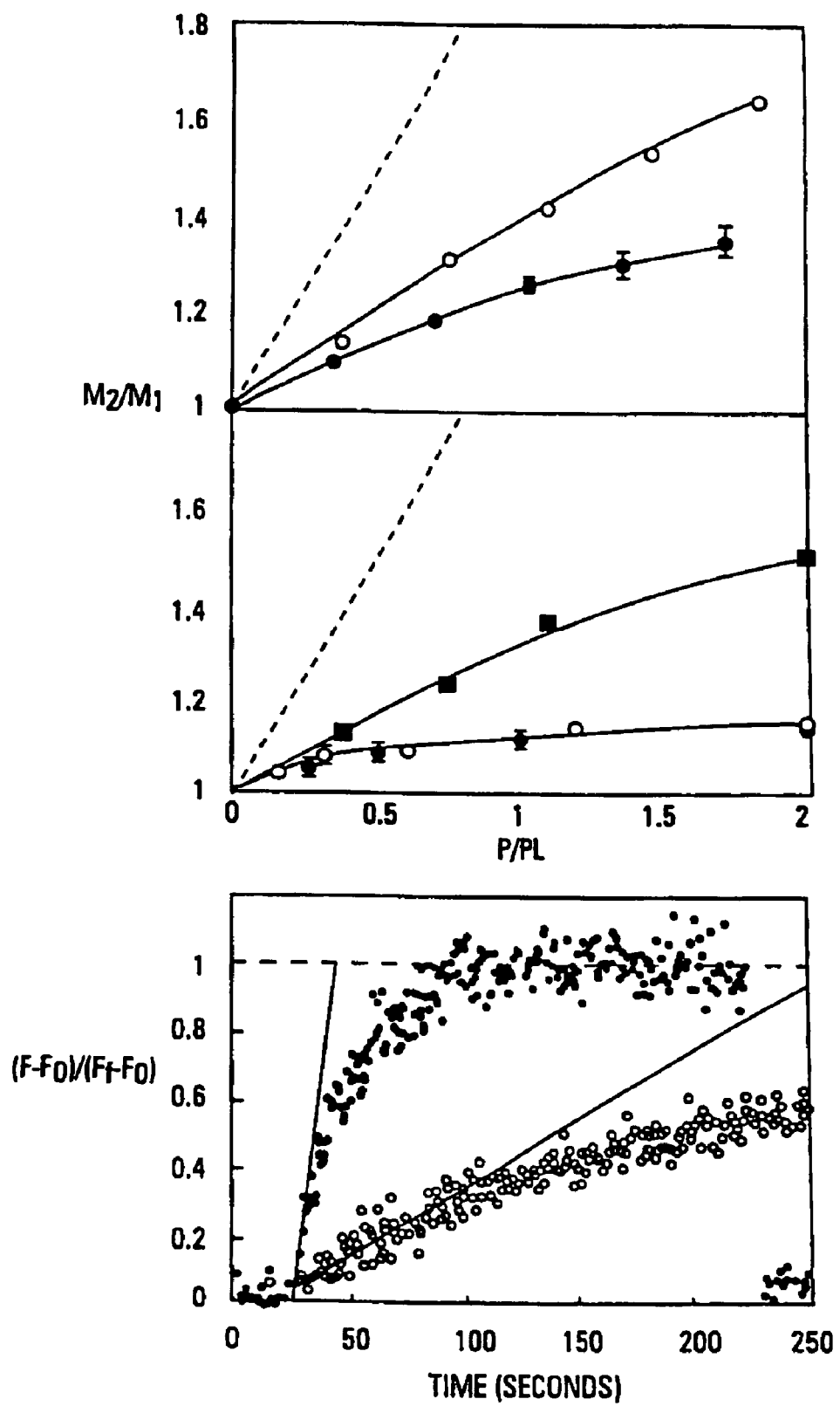
FIG. 15 depicts the membrane interaction properties of different vitamin K-dependent proteins. The top panel compares membrane interaction of human (filled circles) and bovine (open circles) factor X. The middle panel shows membrane interaction by normal bovine prothrombin fragment 1 (open circles), fragment 1 modified with TNBS in the absence of calcium (filled circles) and fragment 1 modified with TNBS in the presence of 25 mM calcium (filled squares). The bottom panel shows the rate of protein Z binding to vesicles at pH 9 (filled circles) and 7.5 (open circles).

The results in the bottom panel of FIG. 15 show that the association rate for protein Z was substantially improved at pH 9, where an amino terminal should be uncharged. The rate constant obtained from these data was about 12-fold higher at pH 9 than at pH 7.5.

TABLE 6

Distance to Sr-1, 8 and Ion Importance

| Atom[a] | | Distance (Å) to: | Impact/ion |
| --- | --- | --- | --- |
| | Sr-1 | Sr-8 | on $K_D(K_M)$ |

Position (A.A-Protein)

| | | | | |
| --- | --- | --- | --- | --- |
| 3(K-PT) | ε-N | 22.1 | 21.7 | Low or Unknown |
| 5(K-IX) | para-C(F) | 20.1 | 20.8 | " |
| 19(K/R-VII) | C5(L) | 20.2 | 17.8 | " |
| 22(K-IX) | C4(P) | 17.0 | 18.5 | " |
| 10(R) | C6(R) | 16.8 | 12.9 | " |
| 25(R-PT) | C6(R) | 11.2 | 13.8 | " |
| 24(X/D-PC) | O(S) | 8.1 | 12.0 | " |
| 11(K-PT, hX, bS; Gla-PZ) | ε-C(K) | 14.7 | 7.4 | 3-10-fold[b] |
| 33(Gla) | γ-C(E) | 11.6 | 7.5 | " |
| 34(D) | O(S) | 15.3 | 12.1 | " |
| 29(R) | para-C(F) | 7.5 | 8.4 | " |
| 16(R) Gla residue[d] | C6(R) | 14.2 | 10.6 | 3-10-fold[c] |

Low importance:

| | | | | |
| --- | --- | --- | --- | --- |
| 7 | | 12.8 | 13.3 | +2 (<2) |
| 15 | | 20 | 16 | <2 (<2) |
| 20 | | 19.4 | 17.8 | <2 (<2) |
| 21 | | 17.2 | 15 | 4(3) |
| 33 | | 11.6 | 7.5 | ?[e](<2) |

TABLE 6-continued

Distance to Sr-1, 8 and Ion Importance

| Atom[a] | | Distance (Å) to: | Impact/ion |
| --- | --- | --- | --- |
| | Sr-1 | Sr-8 | on $K_D(K_M)$ |

High importance:

| | | | |
| --- | --- | --- | --- |
| 8 | 8.7 | 10.9 | ?[e](20) |
| 26 | 3.6 | 9.5 | ?[e](50) |
| 17 | 11.1 | 9.1 | >200(100) |
| 27 | 8.4 | 10.6 | >200(85) |
| 30 | 3.4 | 4.2 | >200(25) |

[a]Distances are from this atom of bovine prothrombin (residue of prothrombin used in measurement is given in parentheses) to strontium 1 and 8 of the Sr-Prothrombin fragment 1 structure. Seshadri et al. 1994, Biochemistry 33: 1087-1092.
[b]For all but 16-R, cations lower affinity and anions increase affinity.
[c]Thariath et al. 1997 Biochem. J. 322: 309-315.
[d]Impact of Glu to Asp mutations, distances are averages for the gamma-carboxyl-carbons. $K_D(K_M)$ data are from Ratcliffe et al. 1993 J. Biol. Chem. 268: 24339-45.
[e]Binding was of lower capacity or caused aggregation, making comparisons less certain.

Example 6

Competition Assay for Assessing Affinity of Modified Factor VII

Clotting activity of wild type and VIIaQ11E33 was assessed using reconstituted tissue factor (Innovin, Dade) and membrane. Saturating amounts of factor VIIa were used (approximately 0.7 μl of Innovin/0.15 ml assay). Factor VIIa and Innovin were added to the plasma-free buffer (6.7 mM CaCl2, 50 mM Tris, pH 7.5, 100 mM NaCl) in 112.5 μl. After 15 minutes, 37.5 μl of factor VII-deficient plasma was added and clotting time was recorded. Tissue factor-dependent activity of VIIaQ11E33 was similar to that of wild-type protein when assayed in this manner. As use of Factor VII-deficient plasma is not representative of in vivo conditions, the relative affinity of modified factor VII for membrane-bound tissue factor was evaluated in the presence of a competing protein. In particular, active site modified factor VIIa was used as the competing protein and was present in abundance (2 nM). The modified factor VII to be assessed was used above the concentration of tissue factor. Under such conditions, free protein concentrations of all proteins were approximately equal to total proteins added. Subtraction of bound protein from total to obtain free protein concentrations represents a small correction. Based on the competition assay, factor VIIaQ11E33 was 41-times more effective than wild type VIIa Example 7

Enhanced Membrane Binding Affinity and Activity of Protein S and other Vitamin K-dependent Polypeptides Protein S (GenBank Accession number M57853 J02917) is a high affinity membrane-binding protein and a cofactor for action of APC. Deficiency in protein S is a strong indicator of thrombosis disease and may be used in patients who have low levels of this protein or who have increased danger of thrombosis. See, for example, Dahlback, *Blood*, 1995, 85:607-614 and U.S. Pat. No. 5,258,288.

Substitutions at amino acids 5 or 9 can enhance membrane binding affinity and activity of Protein S. Residue 9 of Protein S is a threonine residue, while most vitamin K-dependent proteins contain a hydrophobic residue at this position. See, for example, McDonald et al., *Biochemistry*, 1997, 36:5120-5127. Replacement of the analogous residue in human Protein C (a leucine residue) with a glutamine, a hydrophobic to hydrophilic replacement, resulted in a severe loss of activity. See, Christiansen et al., 1995, *Biochemistry*, 34:10376-10382. Thus, there has been confusion about the importance of position 8 in membrane association by vitamin K-dependent proteins.

Human factor VII containing a threonine substitution at amino acid 9 in conjunction with the Q11E33 mutations described above, were prepared by ATG Laboratories, Inc. and provided in an appropriate vector for transfection into human kidney cell line 293, as described above in Example 4.

The vector containing the nucleic acid sequence encoding the mutant factor VII was transfected into human kidney cell line 293, using commercially available kits. The cells were grown and colonies providing high levels of factor VII antigen were selected by dot blot assay, as described for protein C, using commercially available polyclonal antibodies. The amount of factor VII in the conditioned medium also was determined by a coagulation assay, using the competition assay described in Example 6. In general, Factor VII was converted to VIIa by incubation with tissue factor before initiation of coagulation. Identical amounts of VIIa-Q11E33 and VIIa-T9Q11E33 were used in the assays. The factor VII polypeptides were mixed with an appropriate amount of membrane-associated tissue factor (Innovin, Dade). Active site modified VIIa (FFR-VIIa) was added (0 to 3.5 nM) and the reactions were allowed to equilibrate for 60 minutes in 112.5 μL of buffer containing 6.7 mM $CaCl_2$, 50 mM Tris, pH7.5, and 100 m NaCl. Finally, factor VII-deficient plasma was added and time required to form a clot was measured. Efficacy was determined by the clotting time as a function of added inhibitor. Human factor VIIa-T9Q11E33 exhibited a severe loss of competitive binding affinity. Thus, a threonine residue was not optimal at this position. Introduction of a leucine residue into protein 9 of protein S should enhance the membrane affinity and activity of protein S under many conditions.

The basis for high membrane affinity of protein S, despite the presence of substantial sub-optimum residues, may come from other parts of its structure. That is, protein S contains a sequence region known as the 'second disulfide loop' or thrombin sensitive region (residues 46 to 75 of the mature polypeptide). Prothrombin also contains a second disulfide loop in a shorter version. Proteolytic cleavage of the loop in prothrombin results in loss of membrane affinity. See, Schwalbe et al., *J. Biol. Chem.*, 1989, 264:20288-20296. The cleavage may be involved in regulation of protein S activity by providing a negative control to protein S action. The second disulfide loop may serve to produce an optimum membrane binding site such that residues 46-75 fold back onto residues 145 to create an optimum binding site. Isolated residues 1-45 of protein S do not associate with membranes in a calcium-dependent manner, which is unlike residues 1-41 or 1-38 of prothrombin, residues 1-44 of factor X, residues 1-41 of protein C, or residues 1-45 of protein Z that do bind membranes in a calcium-dependent manner. Thus, despite intact protein S having high affinity, results with the isolated 1-45 GLA domain of protein S suggest that the intact protein suffers a substantial loss of affinity in the GLA domain.

Proteolysis prevents proper function of the second disulfide loop in this role, and the resultant protein S shows loss of activity as the membrane affinity declines to that expected by the amino acids in residues 1-45. Thus, enhancement of membrane affinity by introduction of Leu9 and other changes (see below), would create a protein S which is no longer down-regulated by proteolysis and which will be a more effective anticoagulant.

A conserved residue in most vitamin K-dependent proteins is position 5. Leucine is found at this position in both protein S and protein Z. Protein C, factors X and VII, and prothrombin contain phenylalanine, another hydrophobic residue, at the corresponding position. Factor IX contains a lysine at residue 5, a major deviation from other proteins. There appears to be no apparent connection to this unconserved residue and the membrane affinity of factor IX, making the role of position 5 ambiguous.

Substitution of a glutamine residue at position 5 of human protein C resulted in a protein displaying similar affinity for membranes and similar calcium titrations, with reduced clotting activity. Substitution of a leucine for a phenylalanine residue at position 5 of factor VII (which contained the Q11E33 mutations) had much lower activity than the Q11E33 mutant, when assayed by the method of competition with active site modified VIIa (0-3.2 nM) described above. Thus, activity of protein S can be improved by substitution, for example, of a phenylalanine residue at position 5. The P11Q mutation of Factor VII had a positive impact, while the P11E mutant (to make this position like that of protein Z), was without detectable impact. Consequently, the impact of substitutions of individual residues varies with the protein. Appropriate combined substitutions, however, elucidate the universal importance of these residues.

A factor VIIa molecule was produced by procedures outlined above. This mutant contained the Q11E33 mutations and also contained R29F and D34F mutations (Q11F29E33F34 total description). This mutant had 2.5-fold higher activity than the Q11E33 mutant alone when assayed in the competition assay described in Example 6. Thus, the correct combination of amino acid residues at the important sites described, are needed to maximize the function of the important carboxyl groups in the protein. The optimum combination at these sites may include anionic as well as neutral and hydrophobic residues.

Example 8

Insertion of Residue at Amino Acid 4

Factor VII containing a tyrosine residue was prepared by ATG Laboratories, Inc. and assayed by the competition assay described in Example 6. Factor VII was activated by incubation with Innovin (20 ml) in 5 mM calcium. Samples containing sufficient amounts of Innovin to give a minimum clotting time of 28 seconds (about 0.7 μl) were transferred to buffer. Factor VII deficient plasma was added and clotting times were recorded. Samples were assayed at various times until maximum activity was reached (usually ≦30 min.). The amount of Factor VII in the conditioned media needed to generate a clotting time of 30 seconds was determined. This ratio of media/Innovin represents a nearly 1:1 ratio of factor VIIa/Tissue Factor. After activation, samples of the media/Innovin sufficient to give a 19 second clotting time (about 4 μl of Innovin) were diluted to 112.5 μl with buffer containing calcium and BSA (1 g/L). Various amounts of active site modified factor VIIa (DEGR-VIIa) were added and allowed to incubate until equilibrium was reached; typically 60 minutes at 37° C. Human factor VII deficient plasma was added (37.5 μl) and clotting times were measured. Results were compared to similar experiments conducted with media containing wild-type VIIa Based on results from the competitive displacement assay, human factor VII containing a tyrosine residue at position 4 had two-fold higher activity than a similar factor VII molecule lacking this residue.

Example 9

Anticoagulation of human blood by activated protein C (APC)

Figure 16A:
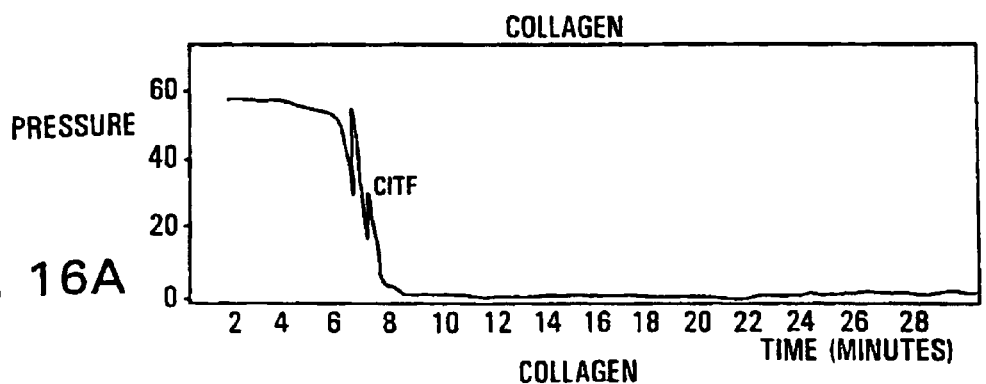
FIGS. 16A-16C are clot signature analyzer reports of collagen induced thrombus formation (CITF) for normal blood (A), for blood containing 30 nM wild type APC (B), and blood containing 6 nM Q11G12E33D34 APC(C).
Figure 16B:
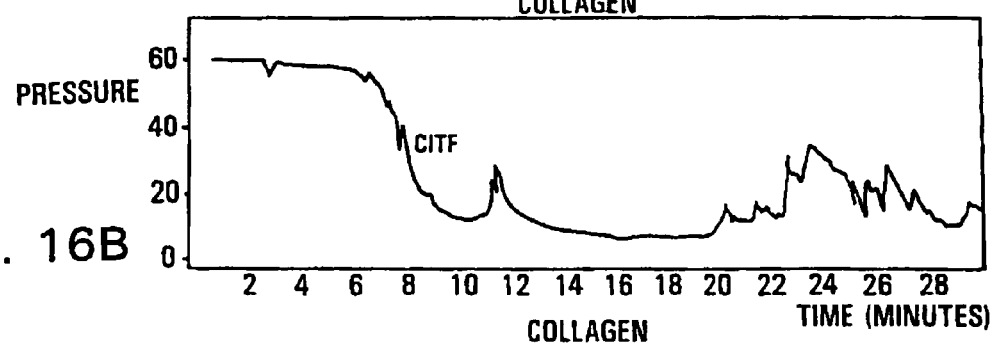
Figure 16C:
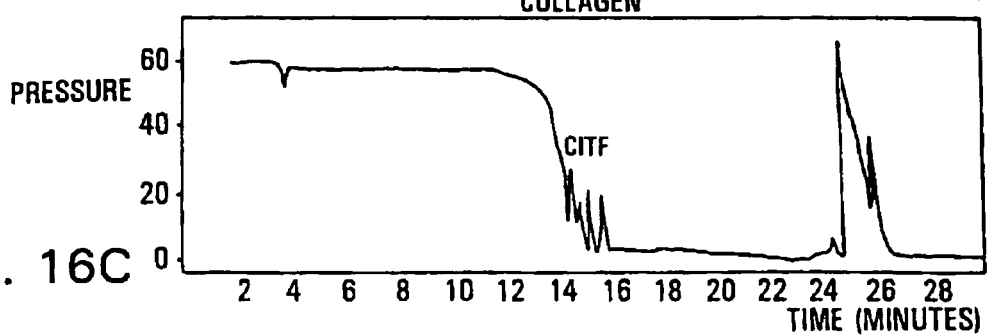

The Clot Signature Analyzer (CSA) apparatus (Xylum Company, Scarsdale, N.Y.) was used to test relative efficacy of wild type APC versus the Q11G12E32D33 mutant. In one assay, this apparatus pumps freshly drawn (<2 min), non-anticoagulated blood through a tube containing a fiber that has a collagen surface. The pressure of blood flow (mm Hg) is similar to that of the circulation system. Platelets in the blood bind to the collagen, become activated and support coagulation. The instrument detects pressure at the outlet of the tube, as shown in FIG. 16. Upon clot formation, pressure at the outlet of the tube declines and the half-reaction point is described as the "Collagen-Induced Thrombus Formation" (CITF) time. Without additives, the CITF time for the human subject was 5.0 minutes (FIG. 16A). Background time is subtracted from the value in FIG. 16 to obtain CITF. With 30 nM wild type APC added to the blood, the average CITF time was 6.5 min (5 determinations) for the same subject (FIG. 16B). The average CITF time was 15.5 min with 6 nM mutant APC (Q11G12E32D33), based on 5 determinations (FIG. 16C), and was 9.5 min with 3 nM of the same mutant APC, based on 5 determinations. Thus, the mutant APC was at least 10-fold more effective than wild type APC for inhibition of clot formation in whole human blood under flow pressure, using activated human platelet membranes as the phospholipid source. In one additional experiment, in which CITF was assessed in a subject that had ingested two aspirins, an even larger difference was observed between mutant and wild type APC. Lower membrane activity may correlate with a larger impact of the mutant.

This result differed from the outcome of an in vitro coagulation test using the hand tilt assay procedure, described earlier in this document. Using the standard conditions and full strength reagents for the APTT test (materials obtained from, and procedures described by the manufacturer, Sigma Chemical Co., St. Louis, Mo., 1998), the mutant protein showed only 1.5-fold higher activity than the wild type protein. The APTT assay, however, contains high levels of phospholipid, a condition that minimizes the difference between mutant and wild type proteins. Once again, these results indicate that assay conditions are important in characterizing the benefit of the mutant proteins produced by this invention and that low phospholipid concentration is characteristic of the biological membrane provided by platelets.

Example 10

Expression and purification of mutant FVII polypeptides

Nucleic acid molecules were prepared that encoded factor VII polypeptides containing a glutamine substitution for proline at position 11 (Q11), a glutamic acid substitution for lysine at position 33 (E33), a glutamic acid or phenylalanine substitution for aspartic acid at position 34 (E34 or F34), a glutamic acid substitution for alanine at position 35 (E35), or a tyrosine insertion at position 4 (Y4), and combinations thereof. Cloning and mutagenesis were performed by ATG Laboratories, Inc. (Eden Prairie, Minn.), following standard procedures (Cormack, 1991, in *Current Protocols in Molecular Biology*, Greene and Wiley Interscience, pp. 8.5.7-8.5.9). Human FVII cDNA was cloned from a human liver cDNA library and then subcloned into the vector pRc-CMV. Mutagenesis was verified by sequencing the entire coding region of all variant FVII proteins including untranslated pre- and pro-peptide segments. Proteins were expressed in fetal human kidney cells (293 cells) that were stably transfected using Lipofectamine™ 2000 (Invitrogen) following the manufacturer's instructions. Following previously outlined procedures (Shen et al., 1997, *Biochemistry*, 36:16025-16031), geneticin resistant colonies were selected and high producing clones were grown to confluence in three layered flasks (Nalge Nunc International Corp., Naperville, Ill.) containing DMEM medium supplemented with 10% FBS, 1.0 mM non-essential amino acids, 50 units/ml penicillin, 50 μg/mL streptomycin, 10 μg/mL vitamin $K_1$, and 100-200 μg/mL geneticin. Confluent cells were rinsed and cultured in serum-free DMEM medium containing 1.0 mM non-essential amino acids, 10 μg/mL vitamin $K_1$ and 0.5 mM benzamidine-hydrochloride. EDTA (pH 7.4) and benzamidine-hydrochloride were added to conditioned medium intended for purification, to concentrations of 5.0 mM and 2.0 mM, respectively. Conditioned medium was vacuum filtered twice through double Whatman (Qualitative #1) filter paper and then through a 0.22 μm polyethersulfone membrane (Corning Inc. Life Sciences, Acton, Mass.). If not immediately purified, filtered medium was stored at −70° C.

Filtered medium was diluted 1:1 with distilled, deionized water containing 4.0 mM EDTA (pH 7.4) and 2.0 mM benzamidine-hydrochloride and then applied to a High Q Marco-Prep (BioRad Inc., Hercules, Calif.) anion exchange column. The column was equilibrated prior to loading and washed extensively with Tris buffer (50 mM Tris, 100 mM NaCl, 0.02% w/w $NaN_3$) pH 7.4 containing 2.0 mM EDTA and 2.0 mM benzamidine-hydrochloride. The column was eluted isocratically with the same buffer containing 400 mM NaCl and no EDTA.

Eluted fractions containing FVII activity were pooled and diluted 1:1 with Tris buffer containing 30 mM $CaCl_2$ and 2 mM benzamidine-hydrochloride. The pooled, diluted fractions were subjected to immunoaffinity chromatography using a calcium-dependent monoclonal antihuman FVII antibody (CaFVII22 provided by Dr. Walter Kisiel, The University of New Mexico Health Sciences Center) coupled to Affi-Prep®Hz (BioRad Corp.) support. Unbound protein was eluted with calcium buffer, and bound protein was eluted with Tris buffer containing 15 mM EDTA and 2.0 mM benzamidine-hydrochloride. Fractions containing FVII activity were pooled and subjected to a final ion exchange column using a Mono Q HR5/5 (Amersham Biosciences Corp., Piscataway, N.J.) anion exchange column. The column was equilibrated and washed extensively with Tris buffer. Proteins were eluted with a linear gradient of increasing NaCl concentration (100 mM to 500 mM over 30 minutes at a flow rate of 1.0 mL/min). Eluted protein was concentrated using centrifugation filtration (Millipore Ultrafree, 10,000 MW cutoff) then stored at −70° C. SDS-PAGE analysis indicated that proteins were highly pure and contained only zymogen FVII or FVIIa in both non-reducing and reducing gels. The percentage of activated FVII ranged from 40% to 95%. Prior to assay for enzyme activity, the proteins were fully activated by a commercially obtained tissue factor (Innovin, Dade Behring, Deerfield, Ill.).

A commercial preparation of FVIIa (NOVOSEVEN®, Novo Nordisk, Princeton, N.J.) was used as the standard for all measurements of FVII protein levels. Protein concentrations were determined by Bradford assay. The amidolytic activity towards the chromogenic substrate S2288 (Chromogenix, Milan, Italy) was also used as a standard of comparison. Previously described plasma clotting assays (Nelsestuen et al., 2001, *J. Biol. Chem.* 276:29825-29831) also were used to determine FVIIa concentration. To ensure that FVIIa was the limiting component, the assay was conducted in the presence of excess tissue factor (TF). TF concentrations in the Innovin preparation were determined from the concentration of NOVOSEVEN® needed to generate maximum activity. The TF concentration in the preparation used in this study was 2.7 nM.

FVII was activated by mixing either crude or purified protein (typically 1.0 µL of solution that resulted in a final concentration of about 0.3 nM FVII) with 20 µl of Innovin solution, followed by incubation at 37° C. until activation was complete. Activation of FVII was monitored by removing 2.65 mL of the activation mixture and adding to 112.5 µL pre-warmed standard Tris buffer (0.05 M, pH 7.4) containing 100 mM NaCl, 1.0 mg/mL bovine serum albumin (BSA), and 6.67 mM $CaCl_2$. To initiate coagulation, 37.5 µL of pre-warmed FVII deficient plasma (Sigma Corp.) was added and clotting time was determined by the hand tilt-test method. Full activation occurred within one hour and concentrations of FVIIa were determined by comparison to NOVOSEVEN® standard. The results for the different assay comparisons gave the same protein concentration within the estimated error of the assays (±20%).

Active site blocked FVIIa (WT-VIIai) was produced as previously described (Nelsestuen et al., 2001, supra) using the active site inhibitor phenylalanylprolylarginyl chloromethylketone (CalBiochem Corp., San Diego, Calif.) and NovoSeven as the source of WT-VIIa. WT-VIIai concentrations were determined using the Bradford assay.

Example 11

Analysis of Protein Carboxylation States by MALDI-TOF Mass Spectrometry

MALDI-TOF mass spectrometry was used to confirm the identity of the FVII variant proteins produced as described in Example 10, and to assess the extent of carboxylation. To release the Gla domains from the intact proteins, purified proteins were incubated at 37° C. for 30 minutes in the presence of either chymotrypsin or trypsin at a ratio of 500 to 1 (w/w) FVII protein to protease. Reaction solutions were dried by vacuum centrifugation and solubilized in a 5:95 acetonitrile:water solution containing 0.1% trifluoroacetic acid. The solutions were desalted using reverse-phase chromatography (ZipTip, Millipore Corp.), mixed 1:1 with a saturated matrix solution (5-methoxysalicyclic acid in 50:50 methanol:water solution), spotted on the spectrometer target, allowed to dry and then subjected to MALDI-TOF mass spectrometry (Bruker Biflex™III). Minimal laser power was used to obtain spectra. Moderate increases in power above this minimum did not result in changes in the distribution of the various carboxylated species observed. The percentage of each carboxylation species was determined by measurement of peak areas using integration software provide by the spectrometer manufacturer.

Figure 17:
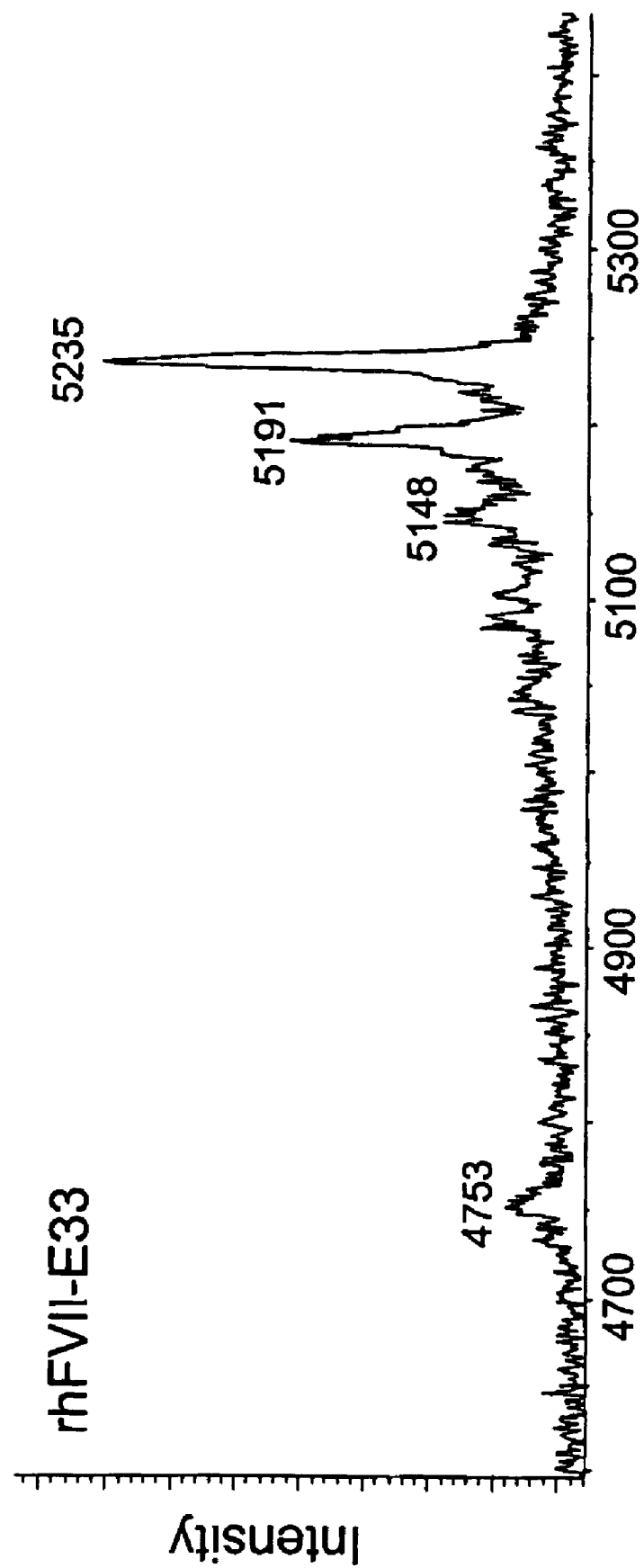
FIG. 17 is a line graph plotting a representative MALDI-TOF mass spectrum for E33-VIIa.

The Gla domains consisted of either amino terminal residues 141 (containing all Gla residues) or amino terminal residues 1-33 (less one carboxylation site at residue 36).In-source decarboxylation of Gla residues occurred during MALDI-TOF analysis and reached quantitative levels when the sinapinic acid matrix was used (Martinez et al., May 27-31, 2001, *Proceedings for the $49^{th}$ conference on Mass Spectrometry and Allied Topics*, Abstract #A011052). However, use of the methoxysalicylic acid matrix and the lowest practical laser power resulted in a low level of undercarboxylated peptide species (FIG. 17). In most cases, the fully carboxylated peptide (theoretical m/z of 5235 for the +1 charge state of E33-VIIa) was the most abundant peak. Undercarboxylation was detected by peaks separated by 44 mass units and a small peak corresponding to the fully decarboxylated peptide (4751 m/z). The quantitative distribution among the different species was very consistent for replicate samples as well as for many plasma-derived vs. recombinant proteins, suggesting that quantitative MALDI-TOF data could be compared to detect relative differences in the carboxylation states of various proteins. Consequently, the somewhat lower yield of the fully carboxylated peptide of recombinant WT-VII (46%; Table 7) suggested undercarboxylation of the parent protein. In fact, undercarboxylation of position 36 in recombinant WT-VIIa is known (Jurlander et al., 2001, *Semin. Thromb. Hemos.*, 27:373-383; and Thim et al., 1988, *Biochem.*, 27:7785-7793). That position 36 of recombinant WT-VII was the major site of undercarboxylation also was suggested by MALDI-TOF analysis of the 1-33 peptide, which gave a normal yield of the fully carboxylated state (70%; Table 7). Undercarboxylation of position 36 of FVII (and a corresponding residue in factor IX (Gillis et al., 1997, *Prot. Sci.*, 6:185-196)) had no detected impact on the activity of the mature proteins.

Total carboxylation levels of WT-VIIa and Q11E33-VIIa, determined by this procedure, were 9.3 (out of 10 theoretical) and 10.4 (out of 11 theoretical) residues per Gla domain, respectively. These estimates were nearly identical to values of 9.6±0.9 and 10.7±0.8 obtained by amino acid analysis after base hydrolysis (Shah et al., 1998, *Proc. Natl. Acad. Sci. USA*, 95:4229-4234).

Comparative analysis by MALDI-TOF was used to estimate the carboxylation states for the FVII mutants produced in this study. Five of the 7 proteins showed greater than 93% of theoretical Gla levels (far right column, Table 7), suggesting a carboxylation state of the parent protein that was similar to commercial FVIIa. Two mutants showed substantially lower levels of carboxylation, 8.9 of 11 theoretical residues for Q11E33-VIIa and 10.9 of 12 theoretical residues for (Y4) Q11E33F34E35-VIIa. The latter mutants contained additional Glu residues beyond position 33. Given that undercarboxylation occurs at position 36 of recombinant WT-VIIa, it was possible that the additional Glu residues at positions 34 and 35 were undercarboxylated as well. If correct, the functional impact of Gla residues at positions 34 and 35 may underestimate the true impact of Gla at these positions.

TABLE 7

Amino acid sequences and yield of different carboxylation states.

| | 1 | 11 | 21 | 31 | 41 | | % Carboxylation | | | |
|---|---|---|---|---|---|---|---|---|---|---|
| | | | | | | | Full | −1 | −2 | Total |
| rhFVII | ANA | FLXXLRPGSLXRXCKXXQCSFXXARXIFKDAXRTKLF | | | | (SEQ ID NO: 22) | 46.1 | 39.6 | 14.3 | 9.32 |
| rhFVII[a] | ANA | FLXXLRPGSLXRXCKXXQCSFXXARXIFKDAXRTKLF | | | | (SEQ ID NO: 22) | 71.6 | 28.4 | 0.0 | 8.72 |
| Q11 | ANA | FLXXLRQGSLXRXCKXXQCSFXXARXIFKDAXRTKLF | | | | (SEQ ID NO: 23) | 54.4 | 28.8 | 16.8 | 9.38 |
| E33 | ANA | FLXXLRPGSLXRXCKXXQCSFXXARXIFEDAXRTKLF | | | | (SEQ ID NO: 24) | 55.2 | 29.3 | 7.7 | 10.52 |
| Q11E33 | ANA | FLXXLRQGSLXRXCKXXQCSFXXARXIFEDAXRTKLF | | | | (SEQ ID NO: 25) | 54.6 | 35.0 | 10.4 | 10.44 |
| Q11E34 | ANA | FLXXLRQGSLXRXCKXXQCSFXXARXIFKEAXRTKLF | | | | (SEQ ID NO: 26) | 5.8 | 52.4 | 31.9 | 8.93 |
| (Y4)Q11E33F34E35 | ANAYFLXXLRQGSLXRXCKXXQCSFXXARXIFEFEXRTKLF | | | | | (SEQ ID NO: 27) | 12.5 | 64.0 | 23.5 | 10.89 |

[a]Digested with trypsin. Chymotrypsin was used in all other cases.
X indicates Gla residues, converted from glutamic acid.

Example 12

Interaction of Purified FVII Variants with Phospholipid Vesicles

Figure 18:
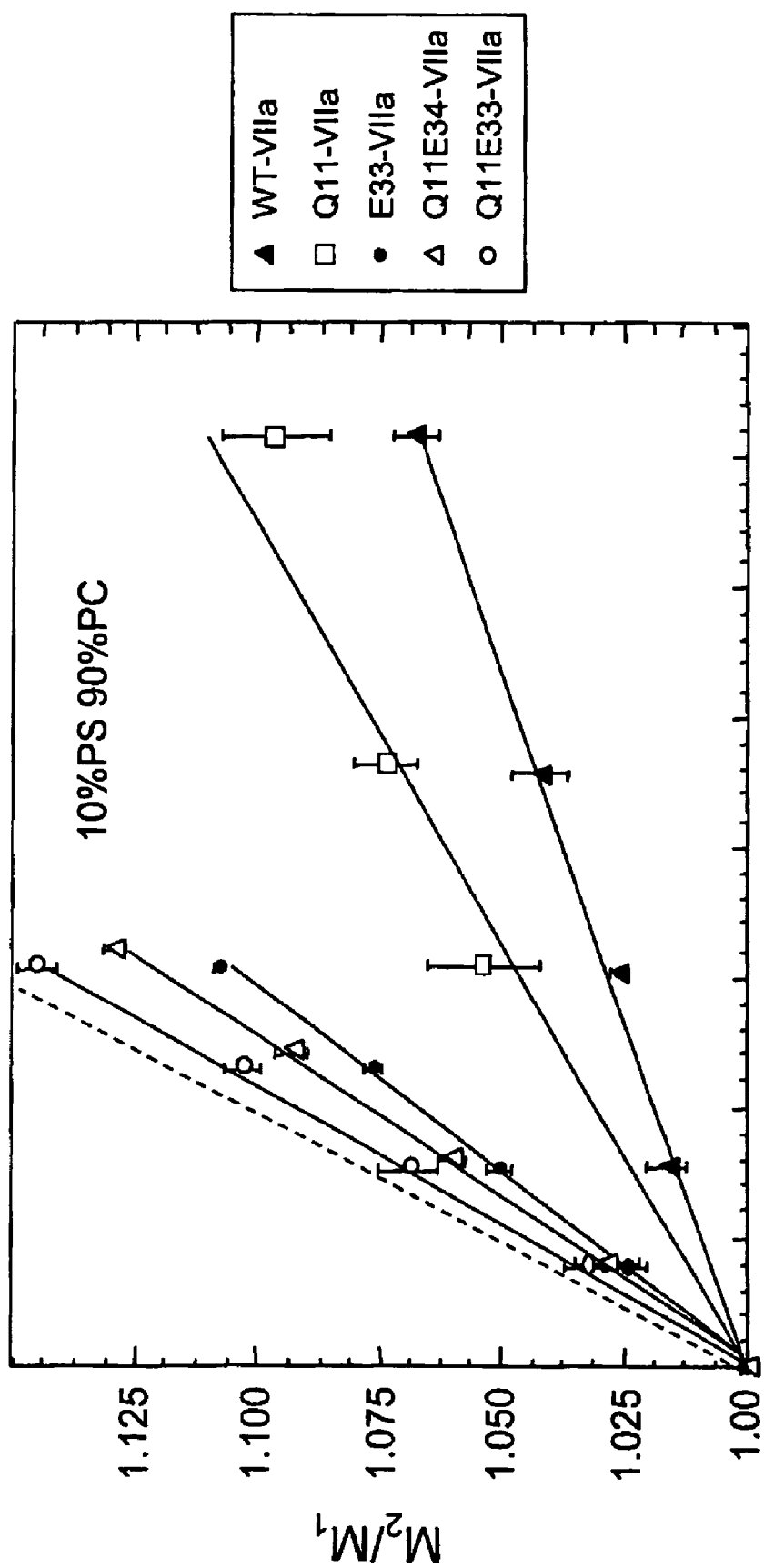
FIG. 18 is a dot plot comparing the binding of variant FVII GLA domains to phospholipid vesicles of PS:PC (10:90). Filled triangles, WT-VIIa; open squares, Q11-VIIa; filled circles, E33-VIIa; open triangles, Q11E34-VIIa; open circles, Q11E33-VIIa.

SUVs were prepared and protein-membrane binding was determined by relative light scattering as described in Example 1. When SUV of PS:PC (25:75) were used to measure protein binding, the protein variants displayed increasing membrane affinity in the order WT-VIIa<Q11-VIIa<E33-VIIa. Mutants with higher affinity bound at the theoretical limit so that equilibrium binding constants could not be estimated. Since binding affinity is dependent on PS content of the membrane, use of a lower PS content (PS:PC, 10:90) provided an equilibrium of bound and free protein for most mutants, demonstrating increasing affinity in the order WT-VIIa<Q11-VIIa<E33-VIIa<Q11E34-VIIa<Q11E33-VIIa (FIG. 18). Dissociation constants estimated from these results are reported in Table 8. The $K_D$ value obtained for Q11E33-VIIa, 0.16±0.08 µM, compared well with the value reported by Shah et al. (supra) (0.22 µM for SUV of PS:PC (10:90)). Even lower PS content was needed in order to estimate the binding constant for the highest affinity mutant (PS:PC 5:95). Estimated $K_D$ values indicated 3-fold enhancement of membrane affinity for the (Y4)Q11E33F34E35-VIIa mutant over the Q11E33-VIIa variant.

TABLE 8

Impact of mutagenesis on FYII activity and membrane affinity

| | Factor X Activation[a] | Clotting Assay[b] | | $K_D$ (µM)[c] | | $\Delta\Delta G_{(e)}$ |
|---|---|---|---|---|---|---|
| | (relative function) | Purified protein | Cond. Media | 10% PS | 5% PS | (kcal/mole) |
| WT-VIIa | 0.8 (1.0) | N.D. (1.0) | N.D. | 5.8 ± 0.6 (1.0) | N.D. | 0.0 |
| Q11-VIIa | 2.4 (3.1) | N.D. | N.D. | 3.2 ± 0.3 (1.8) | N.D. | −0.52 |
| E33-VIIa | 10/3.4 (13) | 0.17 (13.9) | 0.25 | 0.69 ± 0.1 (8.4) | N.D. | −1.28 |
| Q11E33-VIIa | 10.4 (43) | 0.31 (43) | 0.42 (43) | 0.16 ± 0.08 (36) | 1.5 ± 0.3 (36) | −2.06 |
| Q11E34-VIIa | 3.8 (16) | 0.15 (21) | 0.19 | 0.48 ± 0.08 (12) | N.D. | −1.52 |
| (Y4)Q11E33F34E35-VIIa | 35 (149) | 1.2 (166) | 2.9 (296) | N.D. | 0.6 ± 0.08 (95) | −2.8 to −3.5 |

[a]WT-VIIai concentration (nM) at 50% inhibition of 10 nM (standard print) and 3 nM (bold) factor VIIa. Values in parentheses are the functions relative to that of WT-VIIa.
[b]Inhibitor concentration (nM) required to increase clotting time by 58% (log(CT/CTo) = 0.2). Function of the mutants relative to WT-VIIa are in parentheses and are based on a 43-fold improvement of Q11E33 (column 1).
[c]Values represent the average of the $K_D$ values determined from each titration point. Values in parentheses represent the improvement over WT-VIIa.

Example 13

Activation of Factor X by FVIIa

Relative affinities of FVIIa variants were determined by a method outlined previously (Nelsestuen et al., 2001, *J. Biol. Chem.*, 276:39825-39831). Full activation of the FVII was first ensured by incubation with 18 pM TF (Innovin) in 50 µL of Tris buffer containing 5.0 mM $CaCl_2$ and 1.0 mg/mL BSA. The FVII mutant proteins of higher membrane affinity (E33-VIIa, Q11E33-VIIa, Q11E34-VIIa and (Y4)Q11E33F34E35-VIIa) were added to a final concentration of 3.0 nM. WT-VIIa, Q11-VIIa and E33-VIIa were added to a final concentration of 10 nM. Full activation of the FVIIa preparation was achieved after incubation for one hour. A range of WT-VIIai was added and the mixture was allowed to equilibrate for another 2 hours at 37° C. Factor X (Enzyme Research Laboratories) was added to a concentration of 200 nM to initiate the reaction. After 10 minutes the reaction was stopped by addition of excess EDTA (15 mM). Factor Xa concentration was measured as activity toward chromogenic substrate (0.32 mM S-2222, Chromogenix) by monitoring absorbance change at 405 nm in a DU-70 UV/Vis spectrophotometer (Beckman Corp.). The amount of FVIIa bound to tissue factor (TF-VIIa) was estimated from activity observed, relative to that of a standard with no WT-VIIai. The concentration of WT-VIIai bound to TF (WT-VIIai*TF) was estimated from the fraction activity that was lost. Results are presented in a Hill-type plot represented by equation 6.

$$\log([\text{WT-VII}ai*\text{TF}]/[\text{VII}a*\text{TF}]) = \log[\text{WT-VII}ai]/[\text{VII}a] + \log K_{DVIIa}/K_{DVIIai} \quad \text{(eq. 6)}.$$

$K_{D\,VIIai}$ is the dissociation constant for WT-VIIai*TF complex while $K_{DVIIa}$ is the dissociation constant for the FVII*TF concentration. Comparison of a plot of log([WT-VIIai*TF]/[VIIa*TF]) vs. log [WT-VIIai] for two FVIIa variants at identical and constant VIIa concentration will allow estimation of their relative affinities for TF. Equation 6 represents free protein concentrations. Therefore, conditions were selected to ensure that total protein concentration was in large excess over TF so that total protein was approximately equal to free protein.

Functional evaluation of the FVIIa mutants was carried out in a purified system that detected factor X activation. Experiments were performed under equilibrium competition conditions where the FVIIa must displace an inhibitor, WT-VIIai, from TF (described in Nelsestuen et al., 2001, supra, and in Example 6). To allow comparison of results for different proteins, the FVIIa species and WT-VIIai concentrations were maintained in great excess over TF so that the total VIIa and VIIai concentration equaled the respective free concentration. The ability of WT-VIIai to displace 10 nM FVIIa variants from TF showed increasing function in the order WT-VIIa<Q11-VIIa<E33-VIIa. Mutants with higher function were evaluated at 3 nM concentrations and gave increasing affinity in the order: E33-VIIa<Q11E34-VIIa<Q11E33-VIIa<(Y4)Q11E33F34E35-VIIa (FIG. 19).

The WT-VIIai concentrations required to reach 50% inhibition (VIIai-TF/VIIa-TF=1.0) are reported in Table 8. In agreement with the higher affinity of WT-VIIai for TF (Nelsestuen et al., 2001, supra; Sorensen et al., 1997, supra; and Dickinson and Ruf, 1997, *J. Biol. Chem.*, 272, 19875-19879), its concentration at 50% inhibition was lower than that of WT-VIIa.

Figure 19:
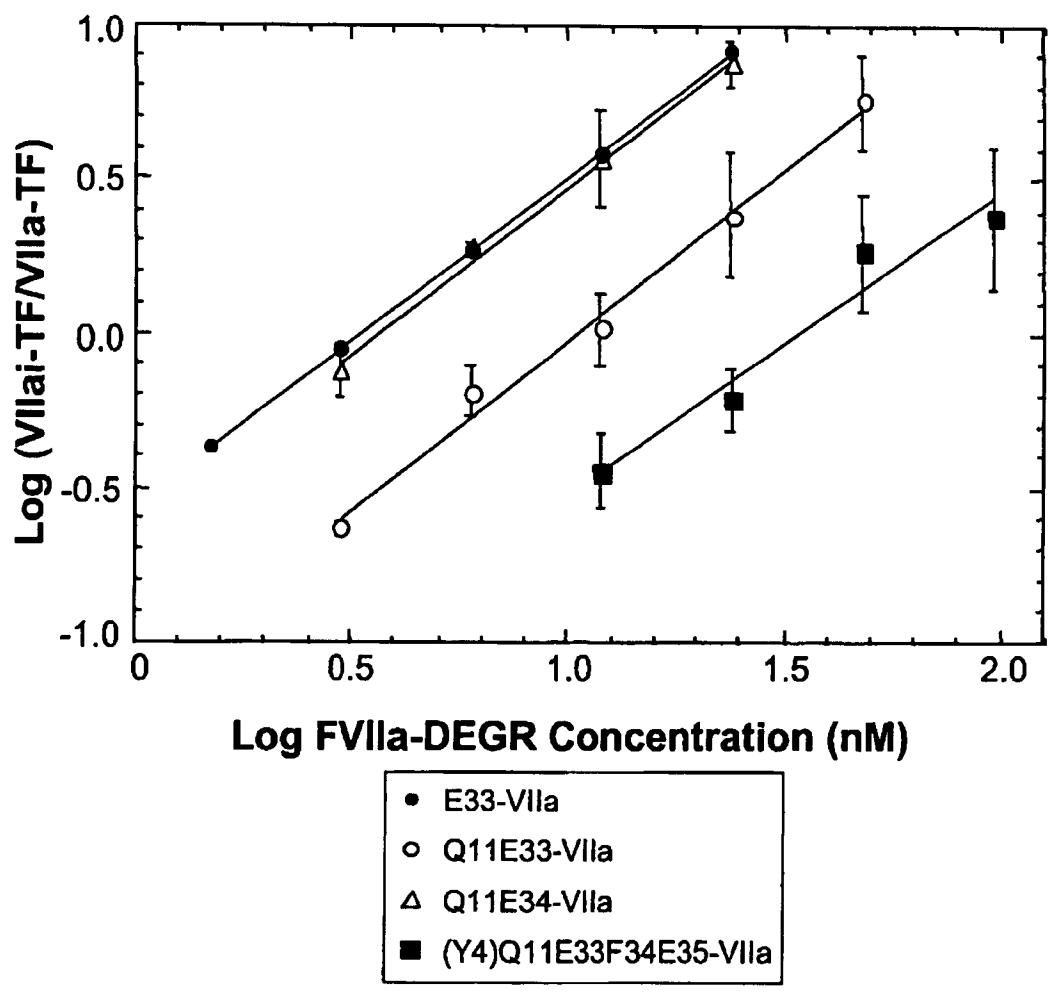

The data in FIG. 19 are presented in as a Hill plot. The plots have slopes of approximately 1.0. The validity of this analysis was supported by titration at different FVIIa levels. For example, a 3.4-fold difference in inhibitor concentration (Table 8) was observed for titration of E33-VIIa at 3 nM vs. 10 nM E33-VIIa. The concentration of WT-VIIai at the midpoint of each titration curve was used to estimate the relative binding affinity of FVIIa variants. The E33-VIIa, Q11E33-VIIa and (Y4)Q11E33F34E35-VIIa mutants displayed 13.8, 45 and 149-fold increases in activity over WT-VIIa, respectively. If the sites make independent contributions to membrane affinity, the 13.8-fold enhancement for E33-VIIa and the 3.1-fold enhancement of the Q11-VIIa mutant would suggest a 42.8 enhancement for the VIIa-Q11E33 mutant. This was very nearly the value that was observed. Thus, this functional assay suggested that the Q11 and E33 modifications functioned in a manner that was independent of each other. The Q11E34-VIIa mutant had a level of activity that was about 40% of the level displayed by the Q11E33-VIIa mutant (Table 8).

Overall, the results of a functional assay in a purified system under conditions where the protein ligands (VIIa and WT-VIIai) are in large excess over TF mirrored the differences in membrane affinity observed in the phospholipid binding studies (FIG. 18). It appeared that all improvements in function arose from changes in the membrane contact site.

Example 14

Clotting Activity by FVII Proteins from Purified and Crude Sources

Pure FVII Preparations or Conditioned Media Containing FVII were added to Innovin (0.1 mL) in an Amount to Generate Approximately 0.3 nM FVII. This concentration of pure FVII provided a final coagulation time of 25 seconds for all samples. Since all FVII variants have the same clotting time in the absence of inhibitor (see pure protein analysis below and Nelsestuen and Lim, supra), use of a constant clotting time allowed the determination of the FVII concentration in an unpurified sample. It was important that TF was maintained in excess over FVII. Activation of FVII was allowed to proceed to completion (60 minutes at 37° C.). Activated FVII solution (containing 2.5 µL of Innovin) plus varying amounts of WT-VIIai were mixed with Tris buffer containing 6.67 mM CaCl$_2$ and 1.0 mg/mL BSA buffer to create 112.5 µL aliquots which were incubated for one hour at 37° C. to achieve equilibrium binding between TF, WT-VIIai and FVIIa. Coagulation was initiated by addition of 37.5 µL of pre-warmed FVII-deficient plasma (Sigma Corp.). Clotting times (CT) were determined and results were evaluated by a plot of log(CT/CTo) vs. log[WT-VIIai] where CTo is the clotting time without inhibitor. Relative function of the different FVIIa variants was estimated by offset of the plots for the two proteins.

Coagulation assays were conducted under conditions where tissue factor was more abundant than FVIIa. To compare the relative function of different FVIIa variants from inhibition by WT-VIIai, it was necessary that the concentration of free VIIai approximate total VIIai. Low affinity variants such as WT-VIIa were displaced at low WT-VIIai where most of the WT-VIIai was bound to TF. Consequently, comparison of protein function by this assay was limited to FVIIa variants with high affinity. This included E33-VIIa and better. These variants are displaced at WT-VIIai concentrations that greatly exceed the TF concentration so that total WT-VIIai approximated free WT-VIIai in the solution.

Figure 20:
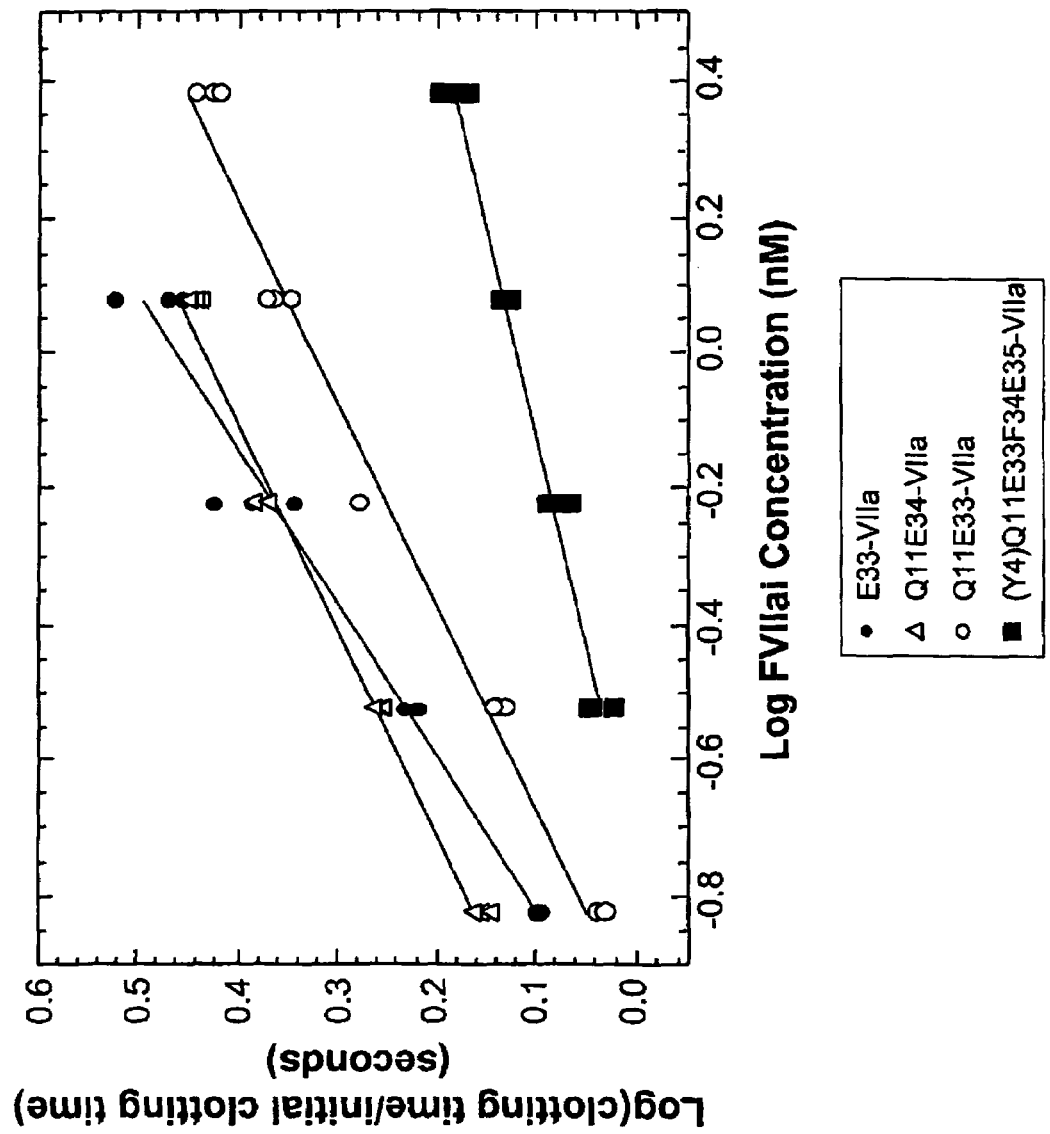
FIG. 20 is a dot plot showing the clotting activity of purified FVII variants. Filled circles, E33-VIIa; open triangles, Q11E34-VIIa; open circles, Q11E33-VIIa; filled squares, (Y4)Q11E33F34E35-VIIa.

The coagulation assay showed the same sequence of function observed by other measurements: E33-VIIa=Q11E34-VIIa<Q11E33-VIIa<(Y4)Q11E33F34E35-VIIa (FIG. 20). Comparison of inhibitor levels needed to increase clotting time by 60% (log(CT/CTo)=0.2) suggested that (Y4) Q11E33F34E35-VIIa had up to 6.9-fold higher function than Q11E33-VIIa. Use of this value and the enhancement of Q11E33-VIIa over WT-VIIa (43-fold) a total enhancement for (Y4)Q11E33F34E35-VIIa was 296-fold (Table 8). In this assay, the Q11E34-VIIa mutant displayed a level of activity that was slightly less than 50% of the level displayed by the Q11E33-VIIa mutant.

This coagulation assay also appeared useful for screening mutants in conditioned media. In fact, results obtained in this crude protein source were very reproducible for different batches of media and were indistinguishable from the results obtained for purified proteins. Screening of FVIIa variants in conditioned media thus was used as a first estimate of protein function in order to identify the best proteins for purification. This assay appeared amenable to high throughput analysis and might be used in future studies to identify beneficial mutants from large libraries of cells expressing proteins with different modifications.

Mutants at positions Y4, F34, and E35 were introduced sequentially into Q11E33-VIIa in order to estimate their individual impacts. These proteins were evaluated only in the preliminary screening test. The result showed that the Y4 insertion conferred a 2-fold functional enhancement that was independent of other changes in the Gla domain. Introduction of F34 also increased function of Q11E33-VIIa by 2-fold. Introduction of E35 into proteins that did not contain E33 had no detected influence on protein function but showed a 1.5-fold increase in function when introduced into Q11E33F34-VIIa. The order of observed enhancements of function generally followed changes in membrane affinity, but appeared to slightly exceed changes in $K_D$ values (Table 8).

It is noted that the Q11E34VIIa mutant had lower membrane binding affinity and lower functional activity than the Q11E33-VIIa mutant. However, membrane binding and functional activity of Q11E34-VIIa were still greatly enhanced as compared to membrane binding and activity of WT-VIIa. The membrane binding and function of Q11E34-VIIa may be improved by production in a cell line that catalyzes full carboxylation of residues beyond position 33. That is, in the 293 cell line used for factor VII, factor VIIa species that lack Gla33 are substantially undercarboxylated at higher positions of the polypeptide (e.g., position 36). Thus, it is likely that function of the Q11E34 mutant can be further improved by selection of a cell line that provides more complete carboxylation.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. An isolated nucleic acid molecule, said nucleic acid molecule comprising a nucleic acid sequence encoding a mutant Factor VII (FVII) or mutant Factor VIIa (FVIIa) polypeptide, said mutant FVII or mutant FVIIa polypeptide comprising a modified γ-carboxyglutamic acid (GLA) domain that enhances membrane binding affinity of said mutant FVII or mutant FVIIa polypeptide relative to a wild type human Factor VII (hFVII) or wild type human Factor VIIa (hFVIIa) polypeptide, wherein said modified GLA domain comprises an amino acid sequence that differs from the amino acid sequence of the GLA domain of hFVII or hFVIIa polypeptide shown in SEQ ID NO:3 in 1 to 5 amino acid substitutions, wherein the proline residue at amino acid position 10 of SEQ ID NO:3 is substituted with a glutamine, aspartic acid or glutamic acid residue in the modified GLA domain, and wherein amino acid positions of the amino acid sequence of the modified GLA domain are numbered according to SEQ ID NO:3.

2. The isolated nucleic acid molecule of claim 1, wherein the proline residue at position 10 of SEQ ID NO:3 is substituted with a glutamine residue in the modified GLA domain.

3. The isolated nucleic acid molecule of claim 1, wherein the arginine residue at position 28 of SEQ ID NO:3 is substituted with a different amino acid residue in the modified GLA domain.

4. The isolated nucleic acid molecule of claim 3, wherein the arginine residue at position 28 of SEQ ID NO:3 is substituted with a phenylalanine residue in the modified GLA domain.

5. The isolated nucleic acid molecule of claim 4, wherein the proline residue at position 10 of SEQ ID NO:3 is substituted with a glutamine residue in the modified GLA domain.

6. The isolated nucleic acid molecule of claim 1, wherein the lysine residue at position 32 of SEQ ID NO:3 is substituted with a different amino acid residue in the modified GLA domain.

7. The isolated nucleic acid molecule of claim 6, wherein the lysine residue at position 32 of SEQ ID NO:3 is substituted with a glutamic acid residue in the modified GLA domain.

8. The isolated nucleic acid molecule of claim 6, wherein the lysine residue at position 32 of SEQ ID NO:3 is substituted with an aspartic acid residue in the modified GLA domain.

9. The isolated nucleic acid molecule of claim 7, wherein the proline residue at position 10 of SEQ ID NO:3 is substituted with a glutamine residue in the modified GLA domain.

10. The isolated nucleic acid molecule of claim 8, wherein the proline residue at position 10 of SEQ ID NO:3 is substituted with a glutamine residue in the modified GLA domain.

11. The isolated nucleic acid molecule of claim 1, wherein the glycine residue at position 11 of SEQ ID NO:3 is substituted with a different amino acid residue in the modified GLA domain.

12. The isolated nucleic acid molecule of claim 11, wherein the proline residue at position 10 of SEQ ID NO:3 is substituted with a glutamine residue in the modified GLA domain.

13. An isolated nucleic acid molecule comprising a nucleic acid sequence encoding a mutant FVII or mutant FVIIa polypeptide having clotting activity, said mutant FVII or FVIIa polypeptide comprising a modified GLA domain that enhances membrane binding affinity of said mutant FVII or mutant FVIIa polypeptide relative to a wild type hFVII or wild type hFVIIa polypeptide, wherein said modified GLA domain comprises an amino acid sequence that differs from the amino acid sequence of the GLA domain of wild type hFVII or wild type hFVIIa polypeptide shown in SEQ ID NO:3 in two amino acid substitutions, wherein a glutamine residue is substituted for the proline residue at amino acid position 10 of SEQ ID NO:3 and a glutamic residue is substituted for the lysine residue at position 32 of SEQ ID NO:3 in the modified GLA domain, and wherein amino acid positions of the amino acid sequence of the modified GLA domain are numbered according to SEQ ID NO:3.

14. An expression vector comprising the isolated nucleic acid molecule of claim 1.

15. An expression vector comprising the isolated nucleic acid molecule of claim 13.

16. An isolated mammalian host cell comprising the isolated nucleic acid molecule of claim 1.

17. An isolated mammalian host cell comprising the isolated nucleic acid molecule of claim 13.

18. A method for producing a mutant FVII or mutant FVIIa polypeptide having clotting activity, the method comprising: (a) providing a culture of the mammalian host cell of claim 16 in a culture medium, (b) culturing the culture under conditions that permit expression of the mutant FVII or mutant FVIIa polypeptide, and (c) isolating the mutant FVII or mutant FVIIa polypeptide from the culture medium.

19. A method for producing a mutant FVII or mutant FVIIa polypeptide having clotting activity, the method comprising: (a) providing a culture of the mammalian host cell of claim 17. in a culture medium, (b) culturing the culture under conditions that permit expression of the mutant FVII or mutant FVIIa polypeptide, and (c) isolating the mutant FVII or mutant FVIIa polypeptide from the culture medium.

* * * * *

UNITED STATES PATENT AND TRADEMARK OFFICE
CERTIFICATE OF CORRECTION

PATENT NO.          : 7,479,551 B2                                        Page 1 of 1
APPLICATION NO.     : 11/539439
DATED               : January 20, 2009
INVENTOR(S)         : Gary L. Nelsestuen It is certified that error appears in the above-identified patent and that said Letters Patent is hereby corrected as shown below:

Column 58, line 26 (Claim 19), please delete "17." and insert --17-- therefor.

Signed and Sealed this

Seventh Day of July, 2009

JOHN DOLL
*Acting Director of the United States Patent and Trademark Office*